(12) United States Patent
Szeto

(10) Patent No.: US 8,618,061 B2
(45) Date of Patent: *Dec. 31, 2013

(54) METHODS FOR REDUCING OXIDATIVE DAMAGE

(75) Inventor: Hazel Szeto, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 186 days.

This patent is subject to a terminal disclaimer.

(21) Appl. No.: 12/843,333

(22) Filed: Jul. 26, 2010

(65) Prior Publication Data

US 2010/0311664 A1    Dec. 9, 2010

Related U.S. Application Data

(63) Continuation of application No. 11/428,188, filed on Jun. 30, 2006, now Pat. No. 7,781,405, which is a continuation of application No. 11/040,242, filed on Jan. 21, 2005, now Pat. No. 7,550,439.

(60) Provisional application No. 60/538,841, filed on Jan. 23, 2004.

(51) Int. Cl.
*A61K 38/07* (2006.01)

(52) U.S. Cl.
USPC ........................................ 514/17.7; 514/21.9

(58) Field of Classification Search
None
See application file for complete search history.

(56) References Cited

U.S. PATENT DOCUMENTS

| 4,522,811 A | 6/1985 | Eppstein et al. |
|---|---|---|
| 5,312,899 A | 5/1994 | Schiller |
| 5,602,100 A | 2/1997 | Brown et al. |
| 5,652,122 A | 7/1997 | Frankel et al. |
| 5,674,534 A | 10/1997 | Zale et al. |
| 5,716,644 A | 2/1998 | Zale et al. |

(Continued)

FOREIGN PATENT DOCUMENTS

| CA | 23/61364 | 9/2000 |
|---|---|---|
| CN | 1328417 A | 12/2001 |

(Continued)

OTHER PUBLICATIONS

Sullivan et al. "Neurotrophic factors for the treatment of Parkinson's disease." Cytokine & Growth Factor Reviews, vol. 22, Issue 3, Jun. 2011, pp. 157-165.*

(Continued)

*Primary Examiner* — Jeffrey E Russel
(74) *Attorney, Agent, or Firm* — Foley & Lardner LLP

(57) ABSTRACT

The invention provides a method for reducing oxidative damage in a mammal, a removed organ, or a cell in need thereof. The method comprises administering an effective amount of an aromatic cationic peptide. The aromatic cationic peptide has (a) at least one net positive charge; (b) a minimum of three amino acids; (c) a maximum of about twenty amino acids, (d) a relationship between the minimum number of net positive charges ($p_m$) and the total number of amino acid residues (r) wherein 3 $p_m$ is the largest number that is less than or equal to r+1; (e) a relationship between the minimum number of aromatic groups (a) and the total number of net positive charges ($p_t$) wherein 3a or 2a is the largest number that is less than or equal to $p_t$+1, except that when a is 1, $p_t$ may also be 1; and (f) at least one tyrosine or tryptophan amino acid.

8 Claims, 52 Drawing Sheets

(56) References Cited

U.S. PATENT DOCUMENTS

| | | | |
|---|---|---|---|
| 5,885,958 A | 3/1999 | Zadina et al. |
| 5,993,848 A | 11/1999 | Suzuki et al. |
| 5,994,372 A | 11/1999 | Yaksh |
| 6,156,748 A | 12/2000 | Panetta et al. |
| 6,221,355 B1 | 4/2001 | Dowdy |
| 6,268,398 B1 | 7/2001 | Ghosh et al. |
| 6,468,798 B1 | 10/2002 | Debs et al. |
| 6,503,713 B1 | 1/2003 | Rana |
| 6,703,483 B1 | 3/2004 | Schiller |
| 6,759,520 B1 | 7/2004 | Carr et al. |
| 6,900,178 B2 | 5/2005 | Oeltgen et al. |
| 7,498,297 B2 | 3/2009 | Szeto et al. |
| 7,550,439 B2 | 6/2009 | Szeto |
| 7,576,061 B2 | 8/2009 | Szeto et al. |
| 7,718,620 B2 | 5/2010 | Szeto et al. |
| 7,732,398 B2 | 6/2010 | Szeto et al. |
| 7,781,405 B2 | 8/2010 | Szeto |
| 2004/0248808 A1 | 12/2004 | Szeto et al. |
| 2005/0096333 A1 | 5/2005 | Dugar et al. |
| 2005/0158373 A1 | 7/2005 | Szeto et al. |
| 2005/0192215 A1 | 9/2005 | Ghosh et al. |
| 2006/0084606 A1 | 4/2006 | Szeto |
| 2007/0027070 A1 | 2/2007 | Szeto et al. |
| 2007/0027087 A1 | 2/2007 | Szeto et al. |
| 2007/0129306 A1 | 6/2007 | Szeto et al. |

FOREIGN PATENT DOCUMENTS

| | | |
|---|---|---|
| WO | WO 95/22557 | 8/1995 |
| WO | WO-96/40073 | 12/1996 |
| WO | WO-99/15154 | 4/1999 |
| WO | WO-00/38651 | 7/2000 |
| WO | WO 00/55189 | 9/2000 |
| WO | WO 02/05748 | 1/2002 |
| WO | WO-02/44126 | 6/2002 |
| WO | WO-02/059080 | 8/2002 |
| WO | WO-02/061105 | 8/2002 |

OTHER PUBLICATIONS

Arias-Carrion et al. "Neurogenesis in Substantia Nigra of Parkinsonian Brains?" in: Birth, Life and Death of Dopaminergic Neurons in the Substantia Nigra. Journal of Neural Transmission. Supplementa, 2009, vol. 73, Part 4, 279-285.*

Second Office Action on Chinese Patent Application 200810177056,9, mailed Nov. 9, 2011 (English translation included), 7 pages.

Berezowska et al. "Highly potent fluorescent analogues of the opioid peptide [Dmt1] DALDA." Peptides, Elsevier, Amsterdam 24: 1195-1200 (2003).

Censura et al. "The Voltage-dependent Anion Channel is the Target for a New Class of Inhibitors of the Mitochondrial Permeability Transition Pore." J Biol Chem 278(50) 49812-49818 (2003).

Futaki S et al., "Arginine-Rich Peptides—an Abundant Source of Membrane-Permeable Peptides Having Potential as Carriers for Intracellular Protein Delivery," J. Biol. Chem. 276, 5836-5840 (2001).

Rigobello MP et al. "Effect of polycation petides on mitochondrial permeability transition." Biochem Biophys Res Comm. 217(1) 144-149 (1995).

Schultz, et al., "Opioids and cardioprotection," Pharmacol Ther., vol. 89, No. 2, pp. 123-137 (2001).

Tsao L.I. et al.,"Hibernation-induction peptide and cell death: [D-Ala2,D-Leu5]enkephalin blocks Bax-related apoptotic processes," Eur. J. Pharmacol, vol. 428, No. 1, pp. 149-151 (2001).

Vives E et al., "Lipophilic pro-oligonucleotides are rapidly and efficiently internalized in HeLa cells," Nucleic Acids Research, 27(20): 4071-4076 (1999).

Zhao, Kesheng, et al., Transcellular transport of a highly polar 3+ net charge opioid tetrapeptide, Journal of Pharmacology and Experimental Therapeutics, 304(1):425-432, 2003.

Crompton, Martin. "The mitochondrial permeability transition pore and its role in cell death." Biochem. J. (1999) 341, pp. 233-249.

Friberg et al., "Cyclosporin A, But Not FK 506, Protects Mitochondria and Neurons against Hypoglycemic Damage and Implicates the Mitochondrial Permeability Transition in Cell Death." The Journal of Neuroscience, Jul. 15, 1998, 18(14); pp. 5151-5159.

Lee et al., "The Mechanisms of Neuronal Death Produced by Mitochondrial Toxin 3-Nitropropionic Acid: The roles of N-Methyl-D-Aspartate Glutamate Receptors and Mitochondrial Calcium Overload." Neuroscience vol. 112, No. 3, pp. 707-716, 2002.

LeMasters et al., "Mitochondrial Dysfunction in the Pathogenesis of Necrotic and Apoptotic Cell Death." Journal of Bioenergetics and Biomembranes, vol. 31, No. 4, 1999, pp. 305-319.

Non-final Office Action received for U.S. Appl. No. 13/247,648 dated Dec. 1, 2011.

Bickel et al., Synthesis and bioactivity of monobiotinylated DALDA: a Mu-specific opioid peptide designed for targeted brain delivery, J Pharmacol and Exp Therapeutics, 268(2): 791-796 (1994).

Corpeleijn et al. Direct association of a promoter polymorphism in the CD36/FAT fatty acid transporter gene with Type 2 diabetes mellitus and insulin resistance, Diabet Med., 23(8):907-911 (2006).

International Search Report and Written Opinion in International Application No. PCT/US2009/33440, dated Apr. 30, 2009.

Notification of Non-Substantial Defects Prior to Notification Prior to Allowance of Israeli Patent Application No. 177030 (093873-0115) Dtd Dec. 20, 2011. [document incorrectly dated Dec. 20, 2012].

Communication from the European Patent Office for EP Application 04707809.2, mailed Jul. 25, 2011 (4 pages).

Anderson et al.; "Mitochondrial H2O2 emission and cellular redox state link excess fat intake to insulin resistance in rodents and humans"; J. Clin. Invest. (2009); vol. 119(3), pp. 573-581.

Anderson et al.; "Mitochondrial production of reactive oxygen species contributes to the β adrenergic stimulation of mouse cardiomyocytes"; J. Physiol. (2011); vol. 589(7); pp. 1791-1801.

Calkins et al.; "Impaired mitochondrial biogenesis, defective axonal transport of mitochondria, abnormal mitochondrial dynamics and synaptic degeneration in a mouse model of Alzheimer's disease"; Hum. Mol. Genet. (2011); vol. 20(23); pp. 4515-4529.

Cao et al.; "Mitochondria-targeted antioxidant attenuates high glucose-induced P38 MAPK pathway activation in human neuroblastoma cells"; Mol. Med. Report. (2012); vol. 5(4); pp. 929-934.

Carter et al.; "Evaluation of the antioxidant peptide SS31 for treatment of burn-induced insulin resistance"; Int. J. Mol. Med. (2011); vol. 28(4); pp. 589-594.

Chen et al.; "Mitochondria-targeted peptide MTP-131 alleviates mitochondrial dysfunction and oxidative damage in human trabecular meshwork cells"; Invest. Ophthalmol. Vis. Sci. (2011); vol. 52(10); pp. 7027-7031.

Cho et al.; "A novel cell-permeable antioxidant peptide, SS31, attenuates ischemic brain injury by down-regulating CD36"; J. Biol. Chem. (2007); vol. 282(7); pp. 4634-4642.

Cho et al.; "Potent mitochondria-targeted peptides reduce myocardial infarction in rats"; Coron. Artery Dis. (2007); vol. 18(3); pp. 215-220.

Dai et al.; "Mitochondrial targeted antioxidant peptide ameliorates hypertensive cardiomyopathy"; J. Am. Coll. Cardiol. (2011); vol. 58(1); pp. 73-82.

Eirin et al.; "A mitochondrial permeability transition pore inhibitor improves renal outcomes after revascularization in experimental atherosclerotic renal artery stenosis" J. Am. Heart Assoc. (2012) (manuscript) 35 pages.

Gilliam et al.; "Doxorubicin acts via mitochondrial ROS to stimulate catabolism in C2C12 Myotubes"; Am. J. Physiol. Cell Physiol. (2012); vol. 302(1); pp. C195-C202.

Han et al.; "Mitochondria-derived reactive oxygen species mediate Heme Oxygenase-1 expression in sheared endothelial cells"; J. Pharmacol. Exp. Ther. (2009); vol. 329(1); pp. 94-101.

Kloner et al.; "Reduction of ischemia/reperfusion injury With Bendavia, a mitochondria-targeting cytoprotective peptide"; J. Am. Heart Assoc. (2012) (proof) 15 pages.

(56) References Cited

OTHER PUBLICATIONS

Lee et al.; "Novel mitochondria-targeted antioxidant peptide ameliorates burn-induced apoptosis and endoplasmic reticulum stress in the skeletal muscle of mice"; Shock (2011); vol. 36(6); pp. 580-585.
Li et al.; "Mitochondria-targeted antioxidant peptide SS31 attenuates high glucose-induced injury on human retinal endothelial cells"; Biochem. Biophys. Res. Commun. (2011); vol. 404(1); pp. 349-356.
Ma et al.; "Superoxide flashes: early mitochondrial signals for oxidative stress-induced apoptosis"; J. Biol. Chem. (2011); vol. 286(31); pp. 27573-27581.
Manczak et al.; "Mitochondria-targeted antioxidants protect against amyloid-β toxicity in Alzheimer's Disease neurons"; J. Alzheimer's Dis. (2010); vol. 20(2); pp. S609-S631.
Min et al.; "Mitochondrial-targeted antioxidants protect skeletal muscle against immobilization-induced muscle atrophy"; J. Appl. Physiol. (2011); vol. 111(5); pp. 1459-1466.
Mizuguchi et al.; "A novel cell-permeable antioxidant peptide decreases renal tubular apoptosis and damage in unilateral ureteral obstruction"; Am. J. Physiol. Renal Physiol. (2008); vol. 295(5); pp. F1545-F1553.
Nieborowska-Skorska et al.; "Rac2-MRC-cIII—generated ROS cause genomic instability in chronic myeloid leukemia stem cells and primitive progenitors"; Blood (2012); vol. 119(18); pp. 4253-4563.
Petri et al.; "Cell-permeable peptide antioxidants as a novel therapeutic approach in a mouse model of amyotrophic lateral sclerosis"; J. Neurochem. (2006); vol. 98(4); pp. 1141-1148.
Powers et al.; "Mitochondria-targeted antioxidants protect against mechanic-alventilation-induced diaphragm weakness"; Crit. Care Med. (2011); vol. 39(7); pp. 1749-1759.
Reddy et al.; "Toxicity of neurons treated with herbicides and neuroprotection by mitochondria-targeted antioxidant SS31"; Int. J. Environ. Res. Public Health. (2011); vol. 8(1); pp. 203-221.
Sharma et al.; "Mitochondrial respiratory complex I dysfunction promotes tumorigenesis through ROS alteration and AKT activation"; Hum. Mol. Genet. (2011); vol. 20(23); pp. 4605-4616.
Sloan et al.; "Mitochondrial permeability transition in the diabetic heart: Contributions of thiol redox state and mitochondrial calcium to augmented reperfusion injury"; J. Mol. Cell. Cardiol. (2012); vol. 52(5); pp. 1009-1018.
Szeto, H.; "Cell-permeable, mitochondrial-targeted, peptide antioxidants"; AAPS J. (2006); vol. 8(2); pp. E277-E283.
Szeto, H.; "Development of mitochondria-targeted aromatic-cationic peptides for neurodegenerative diseases"; Ann. N.Y. Acad. Sci. (2008); vol. 1147:112-21.
Szeto, H.; "Mitochondria-targeted cytoprotective peptides for ischemia-reperfusion injury"; Antioxid. Redox Signal. (2008); vol. 10(3); pp. 601-619.
Szeto et al.; "Mitochondria-targeted peptide accelerates ATP recovery and reduces ischemic kidney injury"; J. Am. Soc. Nephrol. (2011); vol. 22(6); pp. 1041-1052.
Szeto, H.; "Mitochondria-targeted peptide antioxidants: Novel neuroprotective agents"; AAPS J. (2006); vol. 8(3); pp. E521-E531.
Szeto, H. & Schiller, P.; "Novel therapies targeting inner mitochondrial membrane—from discovery to clinical development"; Pharm. Res. (2011); vol. 28(11); pp. 2669-2679.
Thomas et al.; "Mitochondrial targeting with antioxidant peptide SS-31 prevents mitochondrial depolarization, reduces islet cell apoptosis, increases islet cell yield, and improves posttransplantation function"; J. Am. Soc. Nephrol. (2007); vol. 18(1); pp. 213-222.
Wang et al.; "Elevated mitochondrial reactive oxygen species generation affects the immune response via hypoxia-inducible factor-1 α in long-lived Mclk1+/− mouse mutants"; J. Immunol. (2010); vol. 184(2); pp. 582-590.
Whiteman et al.; "Do mitochondriotropic antioxidants prevent chlorinative stress-induced mitochondrial and cellular injury?"; Antioxid. Redox Signal. (2008); vol. 10(3); pp. 641-650.
Yang et al.; "Mitochondria targeted peptides protect against 1-methyl-4-phenyl-1,2,3,6-tetrahydropyridine neurotoxicity"; Antioxid Redox Signal.(2009); vol. 11(9); pp. 2095-2104.
Zhao et al.; "Cell-permeable peptide antioxidants targeted to inner mitochondrial membrane inhibit mitochondrial swelling, oxidative cell death, and reperfusion injury"; J. Biol. Chem. (2004); vol. 279(33); pp. 34682-34690.
Zhao et al.; "Mitochondria-targeted peptide prevents mitochondrial depolarization and apoptosis induced by tert-butyl hydroperoxide in neuronal cell lines"; Biochem. Pharmacol. (2005); vol. 70(12); pp. 1796-1806.
Zhu et al.; "Histone deacetylase-3 activation promotes tumor necrosis factor-alpha (TNF-α) expression in cardiomyocytes during lipopolysaccharide stimulation"; J. Biol. Chem. (2010); vol. 285(13); pp. 9429-9436.
Zhu et al.; "MicroRNA-195 promotes palmitate-induced apoptosis in cardiomyocytes by down-regulating Sirt1"; Cardiovasc. Res. (2011); vol. 92(1); pp. 75-84.
Azzouz, Mimoun, "Gene Therapy for ALS: Progress and Prospects," *Biochemical et Biophysica* Acta, 2006, vol. 1762, pp. 112-1127.
Berendsen, Herman, "A Glimpse of the Holy Grail?," *Science*, Oct. 23, 1998, vol. 282, pp. 642-643.
Bork, "Powers and Pitfalls in Sequence Analysis: The 70% Hurdle," 2000, *Genome Research*, vol. 10, pp. 398-400.
Bork, et al.,"Go Hunting in Sequence Databases But Watch Out for the Traps," *Trends in Genetics*, 1996, vol. 12, pp. 425-427.
Bradley, et al.,"Limits of Cooperativity in a Structurally Modular Protein: Response of the Notch Ankyrin Domain to Analogous Alanine Substitutions in Each Repeat," *J. Mol. Biol.*, 2002, vol. 324, pp. 373-386.
Brenner, "Errors in Genome Annotation," *Trends in Genetics*, 1999, vol. 15, pp. 132-133.
Broekemeier, et al., "Inhibition of the Mitochondrial Permeability Transition by Cyclosporin a During Long Time Frame Experiments: Relationship Between Pore Opening and the Activity of mitochondrial Phospholipases," *Biochemistry*, 1995, vol. 34, pp. 16440-16449.
Citron, Martin, "Alzheimer's Disease: Treatments in Discovery and Development," *Nature Neuroscience Supplement*, Nov. 2002, vol. 5, pp. 1055-1057.
Clapp III, et al., "Cardiovascular and Metabolic Responses to Two Receptor-Selective Opioid Agonists in Pregnant Sheep," *American Journal of Obstetrics and Gynecology*, vol. 178, No. 2, Feb. 1998, pp. 397-401.
Demas, et al., "Anaesthesia for Heart Transplantation," *Br J Anaesth.*, 1986, vol. 58, pp. 1357-1564.
Dimaio, et al., "Synthesis and Pharmacological Characterization in Vitro of Cyclic Enkephalin Analogues: Effect of Conformational Constraints on Opiate Receptor Selectivity," *J. Med. Chem.*, 1982, vol. 25, pp. 1432-1438.
Doerks, et al., "Protein Annotation: Detective Work for Function Prediction," *Trends in Genetics*, 1998, vol. 14, pp. 248-250.
Dooley, C T, et al., "Selective Ligands for the Mu, Delta and Kappa Opioid Receptors Identified from a Single Mixture Based Tetrapepide Positional Scanning Combinatinal Library," *Journal of Biological Chemistry, American Society of Biochemistry and Molecular Biology*, Jul. 24, 1998, Birmingham, US, vol. 273, No. 30, pp. 18848-18856, XP002100725.
Drin, et al., "Studies on the Internalization Mechanism of Cationic Cell-penetrating Peptides," *Journal of Biological Chemistry*, 2003, vol. 278, No. 33, pp. 31192-31201.
File Medline on STN An No. 2005478947. Simmons, Zachary. "Management Strategies for Patients with Amyotrophic Lateral Sclerosis from Diagnosis Through Death." *The Neurologist*, Sep. 2005, vol. 11, No. 5, pp. 257-270. Abstract only.
Fuhrman, et al., "Oxidative Stress Increases the CD36 Scavenger Receptor and the Cellular Uptake of Oxidized Low-density Lipoprotein in Macrophages from Atherosclerotic Mice: Protective Role of Antioxidants and of Paraoxonase," *Atherosclerosis*, Mar. 7, 2002, vol. 161, Issue 2, pp. 307-316.
Guerrini, et al., "Opioid Receptor Selectivity Alteration by Single Residue Replacement: Synthesis and Activity Profile of [Dmt] Deltorphin B," *European Journal of Pharmacology*, 1996, vol. 302, pp. 37-42. Abstract only.

(56) References Cited

OTHER PUBLICATIONS

Herve, et al.,"On the Immunogenic Properties of Retro-Inverso Peptides: Total Retro-Inversion of T-Cell Epitopes Causes a Loss of Binding to MHC II Molecules," Molecular Immunology, 1997, vol. 34, No. 2, pp. 157-163.

Holsey, et al., "Cardiovascular Effects of a µ-Selective Opioid Agonist (Tyrosine-D-Arginine-Phenylalanine-Lysine-NH2) in Fetal Sheep: Sites and Mechanisms of Action," *American Journal of Obstetrics and Gynecology*, vol. 180, No. 5, May 1999, pp. 1127-1130.

Kett, et al., "Baroreflex-Mediated Bradycardia But Not Tachycardia is Blunted Peripherally by Intravenous µ-opioid Agonists," *American Journal of Obstetrics and Gynecology*, vol. 178, No. 5, May 1998, pp. 950-955.

Korczyn, et al., "Emerging Therapies in the Pharmacological Treatment of Parkinson's Disease," *Drugs*, 2002, vol. 62, No. 5, pp. 775-786.

Lasukova, et al., "Activation of Mu-Opioid Receptors and Cardiomyocyte Resistance to Free Radical Damage," *Patol Fiziol Eksp Ter.*, 2001, vol. 2: Abstract Only; article in Russian.

Lishmanov, et al., "Ligands for Opioid and σ-Receptors Improve Cardiac Electrical Stability in Rat Models of Post-Infarction Cardiosclerosis and Stress," *Life Sciences*, 1999, vol. 65, PL pp. 13-17.

Majer, et al., "Synthesis of Methylated Phenylalanines Via Hydrogenolysis of Corresponding 1, 2, 3, 4 Tetrahydroisoquinoline-3-Caraboxylic Acids," *Int. Journal of Peptide & Protein Research*, 1994, vol. 43, pp. 62-68.

Margolis, et al., "Diagnosis of Huntington Disease," *Clinical Chemistry*, 2003, vol. 49, No. 10, pp. 1726-1732.

Moosmann, Bernd and Behl, Christian, Secretory Peptide Hormones Are Biochemical Antioxifants: Structure-Activity Relationship, *Molecular Pharmacology*, vol. 61, No. 2, 2001, pp. 260-268.

Neilan, et al.,"Pharmacological Characterization of the Dermorphin Analog [Dmt1]DALDA, a Highly Potent and Selective µ-Opioid Peptide," *European Journal of Pharmacology*, vol. 419, Issue 1, 2001, pp. 15-23.

Ngo, et al., "Computational Complexity, Protein Structure Prediction, and the Levinthal Paradox," *The Protein Folding Problem and Tertiary Structure Prediction*, K. Merz, Jr. and S. Le Grand, Editors, Birkhauser Boston, 1994.

Omoniyi, et al., "A Peripheral Site of Action for the Attenuation of Baroreflex-Mediated Bradycardia by Intravenous µ-Opioid Agonists," *Journal of Cardiovascular Pharmacology TM*, vol. 35, No. 2, 2000, pp. 269-274.

Pages, et al.,"Cystamine and Cysteamine Increase Brain Levels of BDNF in Huntington Disease Via HSJ1b and Transglutaminase," *Journal of Clinical Investigation*, May 2006, vol. 116, No. 5, pp. 1410-1424.

Patel, et al.,"Pharmacotherapy of Cognitive Impairment in Alzheimer's Disease: A Review," *J. Geriatr. Psychiatry Neurol.*, 1995, vol. 8, pp. 81-95.

Richard, et al., "Cell-penetrating Peptides," *Journal of Biological Chemistry*, 2003, vol. 278, No. 1, pp. 585-590.

Rudinger, J., "Peptide Hormones," 1976, *Ed. J. A. Parson*, University Park Press, Baltimore, pp. 1-7.

Schiller, et al., "Dermorphin Analogues Carrying an Increased Positive Net Charge in Their "Message" Domain Display Extremely High µ-Opioid Receptor Selectivity," *Journal of Medicinal Chemistry*, vol. 32, No. 3, 1989, pp. 698-703.

Schiller, et al., "Opioid peptide analogs with novel activity profiles as potential therapeutic agents for use in analgesia," *Peptide Science-Present and Future, Proc. Int. Pept. Symp.*, 1st, Y. Shimonishi (ed), 1999, pp. 665-669.

Schiller, et al., "Opioid Peptide Analogs With Novel Activity Profiles as Potential Therapeutic Agents for Use in Analgesia," *First International Peptide Symposium, Program & Abstracts*, Nov. 30-Dec. 5, 1997, Kyoto, Japan, 0-36, p. 77.

Schiller, et al., "Synthesis and in Vitro Opioid Activity Profiles of DALDA Analogues," European Journal of Medicinal Chemistry, vol. 35, Issue 10, Oct. 2000, pp. 895-901.

Schiller, et al., "TIPP: A Highly Potent and Stable Pseudopeptide σ Opioid Receptor Antagonist with Extraordinary σ Selectivity," *J. Med. Chem.*, 1993, vol. 36, pp. 3182-3187.

Schiller, et al., "Unsulfated C-Terminal 7-Peptide of Cholecystokinin: A New Ligand of the Opiate Receptor," *Biochemical and Biophysical Research Communications*, 1978, vol. 85, pp. 1332-1338.

Schiller, P.W., et al., "Opioid Peptide Analogs With Novel Activity Profiles as Potential Therapeutic Agents for Use in Analgesia," STN CAPLUS, 1997, No. 132, p. 102403, XP002933635.

Schwarze, Steven R., et al., "In vivo Protein Transduction: Intracellular Delivery of Biologically Active Proteins, Compounds and DNA," *Trends in Pharmacological Sciences*, 2001, vol. 21, pp. 45-48.

Shimoyama, et al., "Antinociceptive and Respiratory Effects of Intrathecal H-Tyr-D-Arg-Phe-Lys-NH2 (DALDA) and [Dmt1] DALDA," *The Journal of Pharmacology and Experimental Therapeutics*, vol. 297, No. 1, Apr. 2001, pp. 364-374.

Shroff, et al., "Effects of Intrathecal Opioid on Extubation Time, Analgesia, and Intensive Care Unit Stay Following Coronary Artery Bypass Grafting," *Journal of Clinical Anesthesia*, 1997, vol. 9, pp. 415-419.

Skolnick, et al., "From Genes to Protein Structure and Function: Novel Applications of Computational Approaches in the Genomic Era," *Trends in Biotech*, 2000, vol. 18, No. 1, pp. 34-39.

Smith, et al., "The Challenges of Genome Sequence Annotation or 'The devil is in the details,'" *Nature Biotechnology*, 1997, vol. 15, pp. 1222-1223.

Song, et al., "A Potent Opiate Agonist Protects Against Myocardial Stunning During Myocardial Ischemia and Reperfusion in Rats," *Coronary Artery Disease*, 2005, vol. 16, pp. 407-410.

Spetea, Mariana, et al., "Interaction of Agonist Peptide (3H) Tyr-D-Ala-Phe-NH2 With Mu-Opioid Receptor in Rat Brain and CHO-mu/1 Cell Line," Peptides (New York), 1998, vol. 19, No. 6, pp. 1091-1098, XP002410285.

Sriram, et al.,"Experimental Allergic Encephalomyelitis: A Misleading Model of Multiple Sclerosis," *Ann. Neurol.*, 2005, vol. 58, pp. 939-945.

Steinman, et al.,"How to Successfully Apply Animal Studies in Experimental Allergic Encephalomyelitis to Research on Multiple Sclerosis," *Ann Neurol.*, 2006, vol. 60, pp. 12-21.

Stoessl, Jon A., Potential Therapeutic Targets for Parkinson's Disease., *Expert Opin. Ther. Targets*, 2008, vol. 12, No. 4, pp. 425-436.

Szeto, et al., "In Vivo Disposition of Dermorphin Analog (DALDA) in Nonpregnant and Pregnant Sheep," *The Journal of Pharmacology and Experimental Therapeutics*, vol. 284, No. 1, 1998, pp. 61-65.

Szeto, et al., "In Vivo Pharmacokinetics of Selective µ-Opioid Peptide Agonists," *The Journal of Pharmacology and Experimental Therapeutics*, vol. 298, No. 1, Jul. 2001, pp. 57-61.

Szeto, et al., "Mu-Opioid Receptor Densensitization and Resensitization in Vivo," *International Narcotics Research Conference*, Poster Abstracts, Monday, 1999, Mon19, p. 5.

Szeto, et al., "Respiratory Depression After Intravenous Administration of σ-Selective Opioid Peptide Analogs," *Peptides*, vol. 20, 1999, pp. 101-105.

Wells, James A., "Additivity of Mutational Effects in Proteins," *Biochemistry, American Chemical Society*, Sep. 18, 1990, vol. 29, No. 37.

Wu, et al.,"Myocardial Protective Effect of Mu Opioid Agonists," *International Narcotics Research Conference*, Poster Abstracts, Sunday, 1999, Sun59, p. 15.

Wu, et al., "A Highly Potent Peptide Analgesic the Protects Against Ischemia-reperfusion-induced Myocardial Stunning," *American Journal of Physiol Heart Circ Physiol*, 2002, pp. 283:H783-H791.

Zadina J., et al., "A Potent and Selective Endogeneous Agonist for the MU-Opiate Receptor," *Nature*, Nature Publishing Group, London, GB, Apr. 3, 1997, vol. 386, pp. 499-502, XP002072008.

Zhang, et al., "Oxidative Stress and Genetics in the Pathogenesis of Parkinson's Disease," *Neurobiology of Disease*, Aug. 2000, vol. 7, Issue 4, pp. 240-250.

(56) References Cited

OTHER PUBLICATIONS

Zhao, et al., "Profound Spinal Tolerance After Repeated Exposure to a Highly Selective μ-Opioid Peptide Agonist: Role of σ-Opioid Receptors," *J. Pharma. Exper. Thera.*, vol. 302, No. 1, 2002, pp. 188-196.
Zhao, Kesheng, et al., "Transcellular Transport of a Highly Polar 3+ Net Charge Opioid Tetrapepdide," *Journal of Pharmacology and Experimental Therapeutics*, vol. 304, No. 1, 2003, pp. 425-432.
Zhao, Kesheng, et al., "Translocation of a 3+ Net Charge Tetrapeptide Across Plasma Membrane of Mammalian Cells." Abstract published on-line May 1, 2002 for the World Congress of Pharmacology meeting held Jul. 7, 2002.
Australian Examiners First Report on application 2005208821 dated Mar. 17, 2010, 3 pages.
Canadian Examiners Report issued on Application 2,554,166 dated Jul. 12, 2011, 3 pages.
English Translation of Office Action issued on Japanese Application 2006-503317 dated Apr. 25, 2010, 5 pages.
English Translation of Office Action issued on Japanese Application 2006-551350 dated Dec. 6, 2010, 3 pages.
US Notice of Allowance on U.S. Appl. No. 10/771,232 dated Februrary 3, 2009, 4 pages.
US Notice of Allowance on U.S. Appl. No. 10/771,232 dated Jan. 10, 2008, 4 pages.
US Notice of Allowance on U.S. Appl. No. 11/040,242 on Dec. 12, 2008, 6 pages.
US Notice of Allowance on U.S. Appl. No. 11/427,804 dated Dec. 29, 2009, 4 pages.
US Notice of Allowance on U.S. Appl. No. 11/428,188 dated Apr. 16, 2010, 4 pages.
Alam, N.M. et al., "A Novel Peptide (MTP-131) that Improves Mitochondrial Function Reverses Visual Decline in Mouse Models of Metabolic Dysfunction Leading to Diabetes," American Diabetes Association, (2012), Poster Presentation (1 page).
Alam, N.M. et al., "Reducing Mitochondrial Oxidative Stress to Treat Diabetes and Age-related Visual Decline," Society of Neuroscience, (2011), Poster Presentation (1 page).
Alam, Nazia et al., "A novel Peptide that Improves Mitochondrial Function Reverses Diabetes- and Age-Related Visual Decline," American Aging Association, (2012), Abstract (1 page).
Brown, David A. et al., "Bendavia, a mitochondria-targeting peptide, reduces reperfusion injury and reactive oxygen species levels through a mechanism independent of direct oxygen radical scavenging: a multicenter study," American Heart Association, (2012), Abstract (1 page).
Brown, David A., Ph.D., "Mitochondrial Derived Cardioprotection in Exercised Hearts: Role of Cardiac Glutathione," American College of Sports Medicine, (2012), DB Lab Presentation (28 pages).
Chonn, Arcadio et al., "Recent Advances in Liposomal Drug-Delivery Systems," Current Opinion in Biotechnology, (1995), vol. 6, pp. 698-708.
Eirin, Alfonso et. al., "Chronic Treatment with Bendavia Preserves the Stenotic Kidney in Swine Atherosclerotic Renovascular Disease (ARVD)," American Society of Nephrology, (2012), Abstract & figures (2 pages).
Eirin, Alfonso et. al., "Mitochondrial Targeted Peptides Attenuate Myocardial Damage after Renal Revascularization in Experimental Atherosclerotic Renovascular Hypertension," American Society of Nephrology, (2012), Abstract & figures (2 pages).
Eirin, Alfonso, et. al., "MTP-131 reduces renal injury after percutaneous transluminal renal angioplasty (PTRA) in swine atherosclerotic renal artery stenosis (ARAS)," American Society of Nephrology, (2011), Poster Presentation (1 page).
Gregoriadis, Gregory, "Engineering Liposomes for Drug Delivery: Progress and Problems," Tibtech, (Dec. 1995), vol. 13, pp. 527-537.
Hale, Sharon L. et. al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, (2011), Poster Presentation (1 page).
Kloner, Robert A., et. al., "Bendavia, A Novel Mitochondrial-Targeted Cytoprotective Compound Reduces Ischemia/Reperfusion Injury: Experience in 3 Independent Laboratories," American Heart Association, (2011), Abstract (2 pages).
Liang, XL., et. al., "SS31 protects human RPE cells from oxidative damage and reduces laser-induced choroidal neovascularization," Association for Research in Vision and Opthamology, (2010), Poster Presentation (1 page).
Lichtenberg, Dov et al., "Liposomes: Preparation, Characterization and Preservation," Methods of Biochemical Analysis, (1988), vol. 33, pp. 337-462.
Liu, Shaoyi et. al., "Boosting mitochondrial function to minimize ischemia-reperfusion injury," Experimental Biology, (2011), Poster Presentation (1 page).
Liu, Shaoyi et. al., "Mitochondria-targeting peptide (SS-31) promotes rapid repair of actin cytoskeleton following ischemia and protects tubular epithelial cell architecture," American Society of Nephrology, (2012), Abstract (2), (1 page).
Marcinek, David J., et al., "Acute pharmacological intervention reverses mitochondrial deficits and improves function in aged skeletal muscle," American Aging Association, (2012), Abstract (1 page).
Min, Kisuk et. al., "Mitochondrial-targeted antioxidants attenuate immobilization-induced skeletal muscle atrophy," Experimental Biology, (2011), Abstract (1 page).
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.
Putney, Scott D., "Encapsulation of proteins for improved delivery," Current Opinion in Chemical Biology, (1998), vol. 2, No. 4, pp. 548-552.
Rabinovitch, Peter, "Mitochondrial Oxidative Stress and Cardiac Aging," Basic Cardiovascular Sciences, (2011), Presentation (19 pages).
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, (2010), Abstract (1 page).
Sabbah, Hani N. et al., "Acute Intravenous Infusion of Bendavia (MTP-131), A Novel Mitochondria-Targeting Peptide, Improves Left Ventricular Systolic Function in Dogs With Advanced Heart Failure," American Heart Association, (2012), Abstract (1 page).
Szeto, Hazel H. et. al., "Mitochondria-targeting peptide (SS-31, Bendavia®) prevents microvascular rarafaction, inflammation, and fibrosis caused by ischemia-reperfusion injury," American Society of Nephrology, (2012), Abstract (1 page).
Szeto, Hazel H., "Mitochondrial Protection as Strategy to treat Ischemia-Reperfusion Injury," American Society of Nephrology, (2010), Presentation (17 pages).
Szeto, Hazel H., "The development of a therapeutic peptide for mitochondrial protection—from bench to bedside," Experimental Biology, (2011), Poster Presentation (1 page).
Szeto, Hazel H., et. al., "Rapid Restoration of ATP by SS-31, an Inhibitor of Mitochondrial Permeability Transition, Prevents Tubular Cytoskeletal Rearrangement in Renal Ischemia-Reperfusion Injury," American Society of Nephrology, (2010), Poster Presentation (1 page).
Tiganis, Tony, "Reactive Oxygen Species & NAPDH Oxidases in Insulin Signalling," NOX Gordon Research Conference, (Jun. 3-8, 2012), Presentation (44 pages).
US Notice of Allowance on U.S. Appl. No. 13/247,648 Dtd Nov. 23, 2012 (13 pages).
US Notice of Allowance on U.S. Appl. No. 13/247,648 Dtd Aug. 16, 2012 (5 pages).
Weiner, Alan L., "Liposomes for Protein Delivery: Selecting Manufacture and Development Processes," Immunomethods, (1994), vol. 4., pp. 201-209.
English Translation of Office Action issued on Korean Application 2006-7016975 dated Jul. 25, 2011, 3 pages.

(56) References Cited

OTHER PUBLICATIONS

English Translation of Search Report and First Office Action issued on Chinese Application 201210021864.2 dated Jun. 3, 2013 (4 pages).
Indian First Examination Report on Application 2390/KOLNP/2005 dated Apr. 13, 2010, 2 pages.
Israeli Office Action for application 177030 dated Jun. 9, 2009, English Translation, 2 pages.
Israeli Office Action issued on Application 177030 dated Aug. 26, 2010, 2 pages.
Li Guichang, et al., "Mitochondrial Permeability Transition and Cells Death", Carcinomatosis, Aberrance, and Mutation, vol. 14, Issue 2, Apr. 30, 2002, pp. 127-130. English translation not provided.
Non-Final Office Action on U.S. Appl. No. 13/778,994 dated Jul. 12, 2013, (7 pages).
US Nonfinal Office Action on U.S. Appl. No. 11/428,188 dated Dec. 10, 2009, 12 pages.
US Final Office Action on U.S. Appl. No. 12/753,403 dated Mar. 30, 2011, 20 pages.
US Nonfinal Office Action on U.S. Appl. No. 10/771,232 dated Jun. 12, 2008, 7 pages.
US Nonfinal Office Action on U.S. Appl. No. 11/040,242 dated Jan. 15, 2008, 21 pages.
US Nonfinal Office Action on U.S. Appl. No. 11/427,804 dated Jun. 22, 2009, 5 pages.
US Nonfinal Office Action on U.S. Appl. No. 11/428,188 dated Mar. 27, 2009, 9 pages.

\* cited by examiner

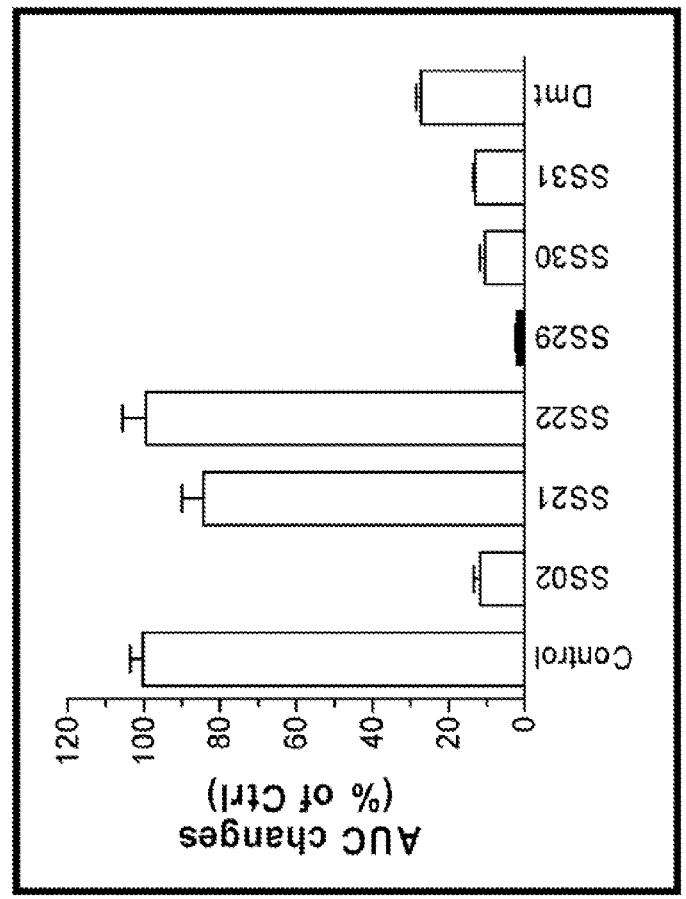
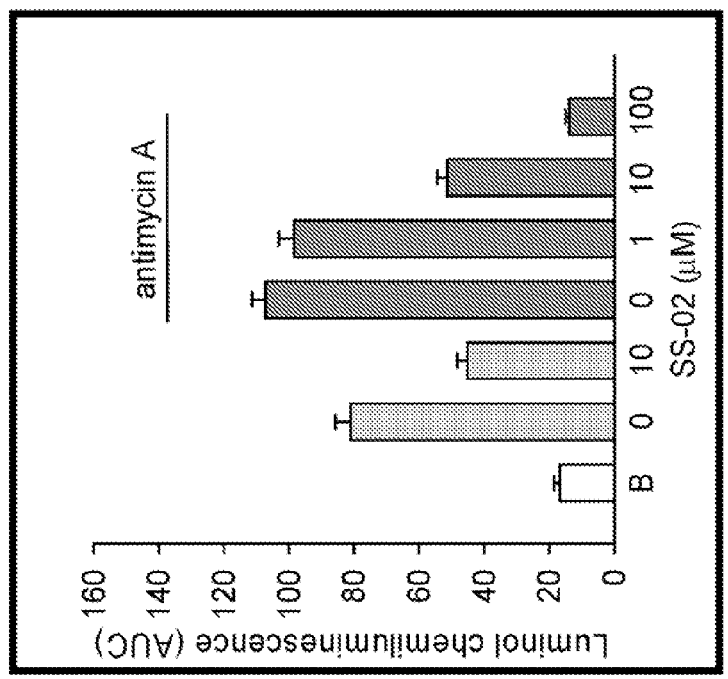
Fig. 4A
Fig. 4B

Antimycin-induced ROS production

Spontaneous ROS production

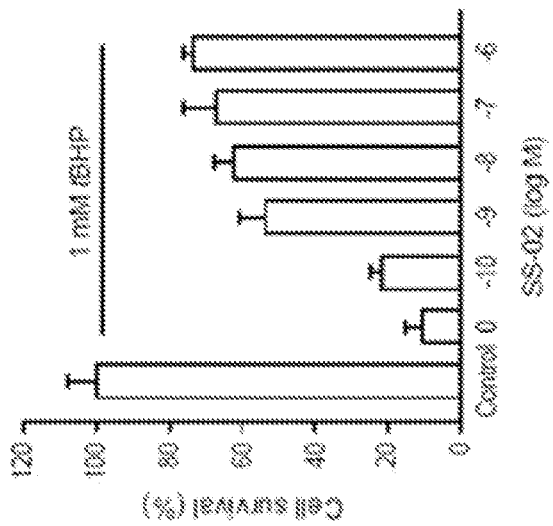
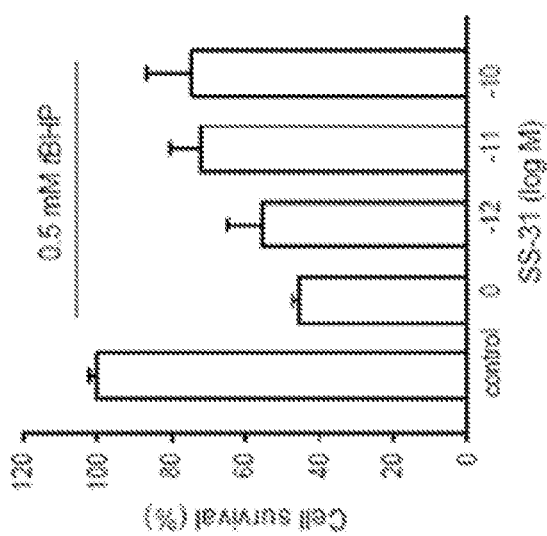
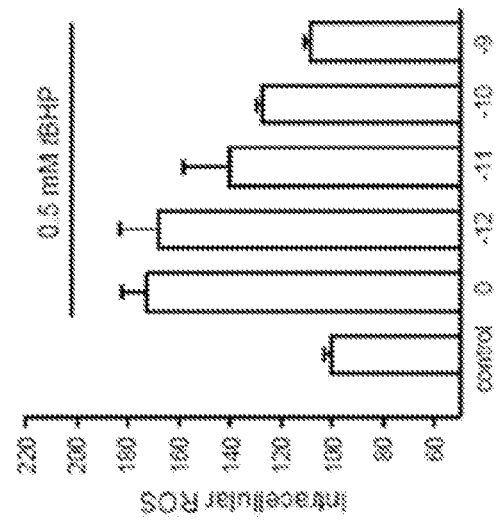

Fig. 12A1
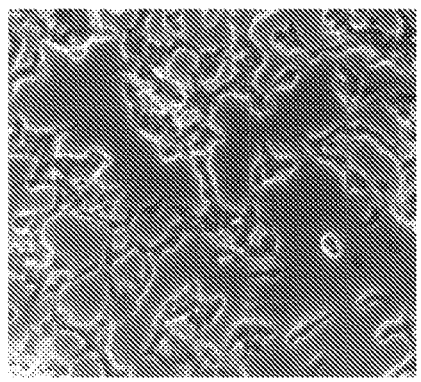
Fig. 12A2
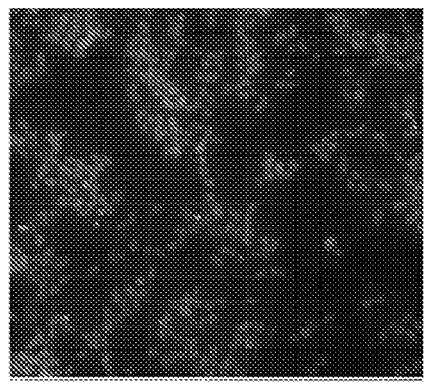
Fig. 12B1
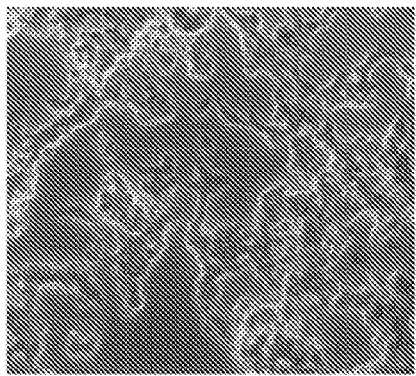
Fig. 12B2
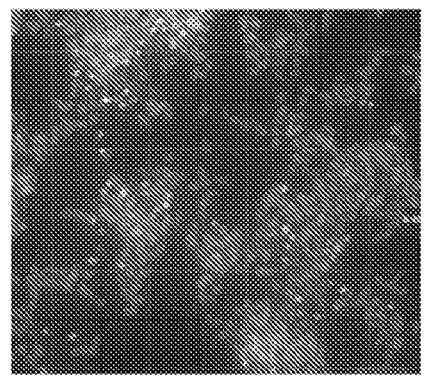
Fig. 12C1
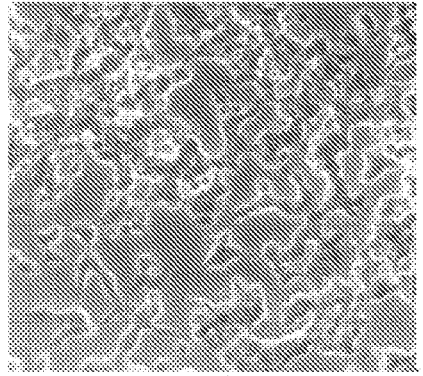
Fig. 12C2
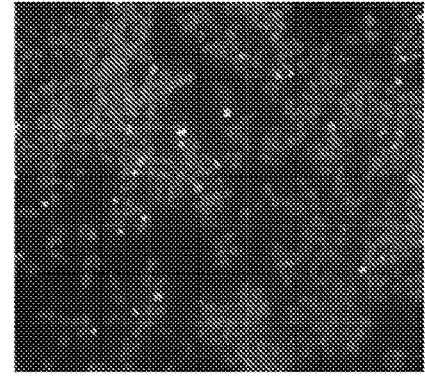

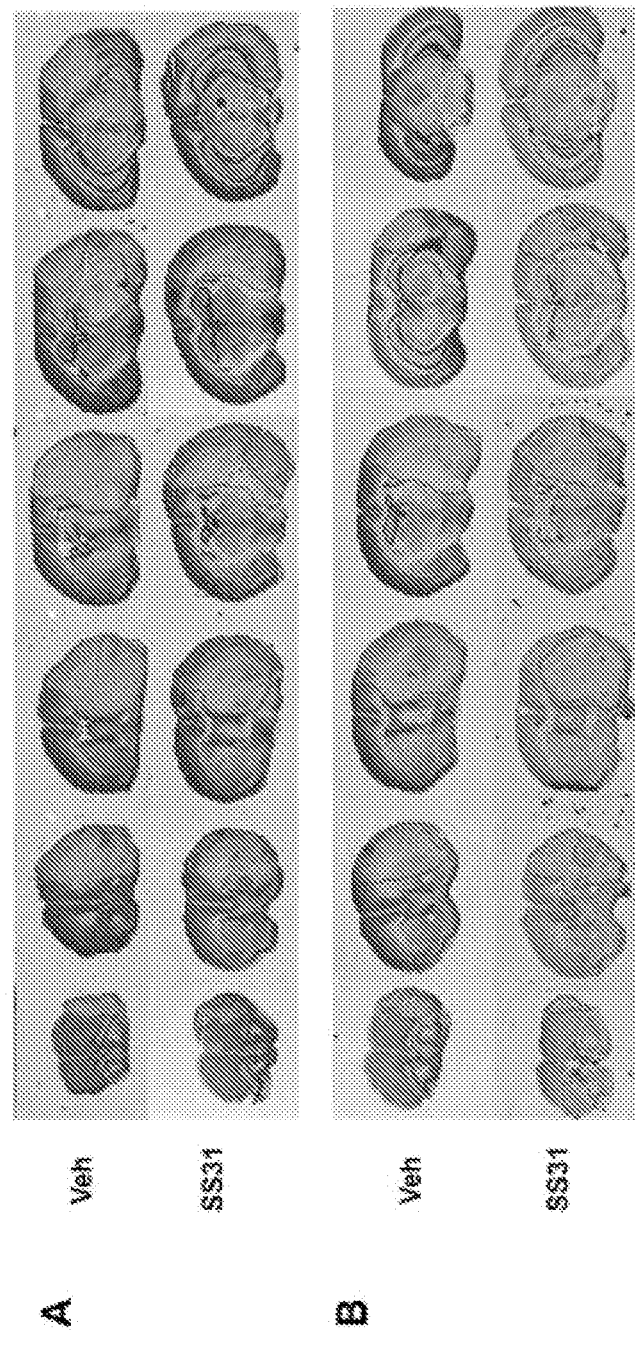
Figures 32 A and B

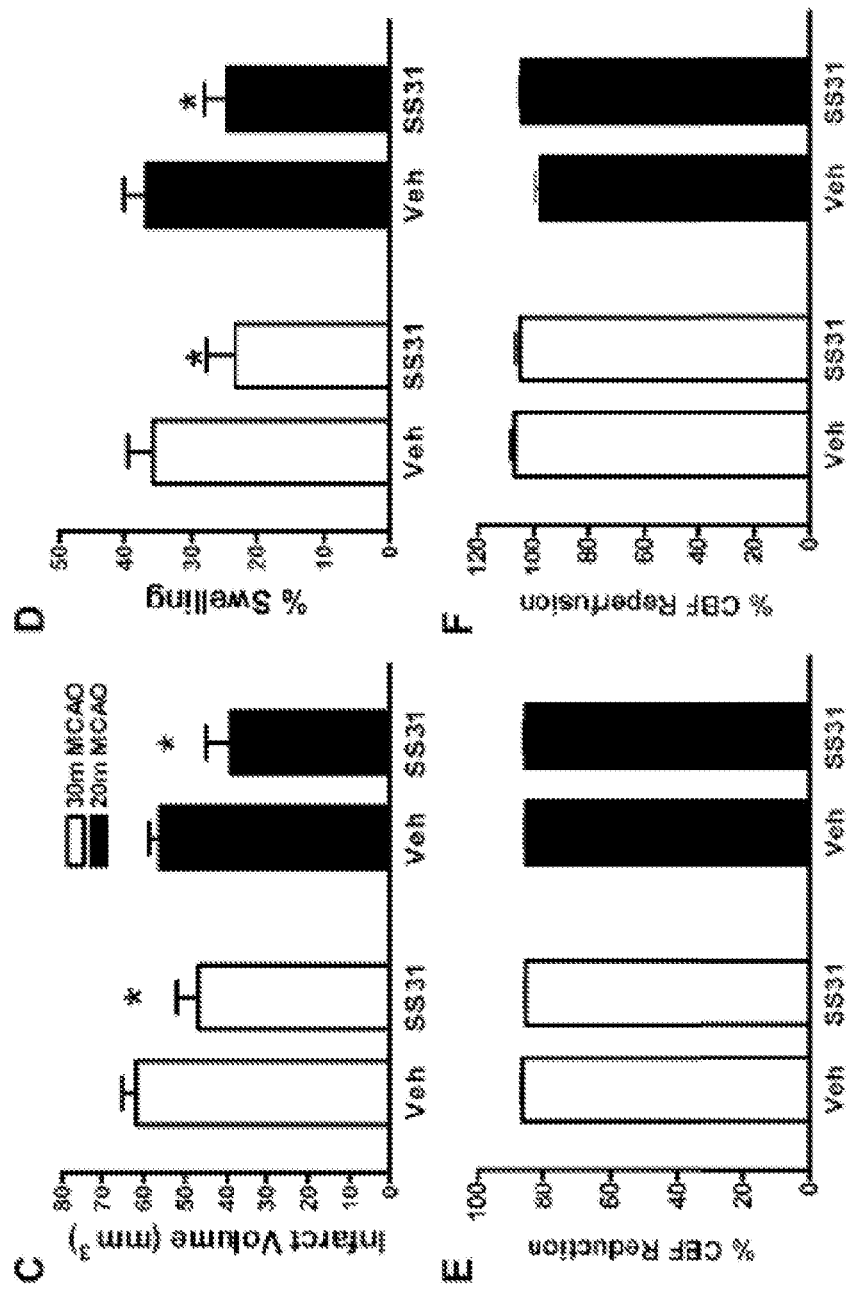
Figures 32 C, D, E and F

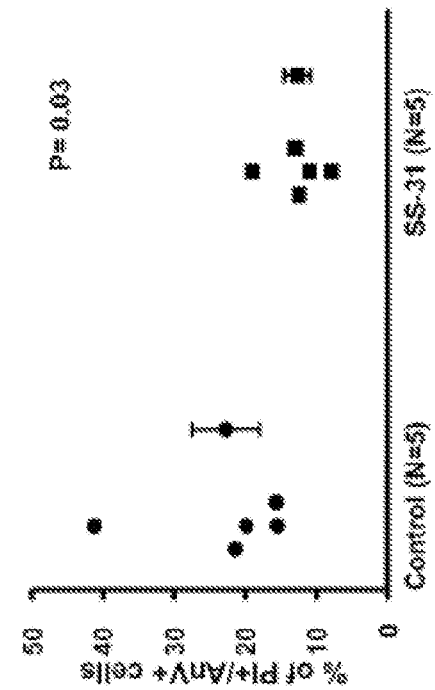
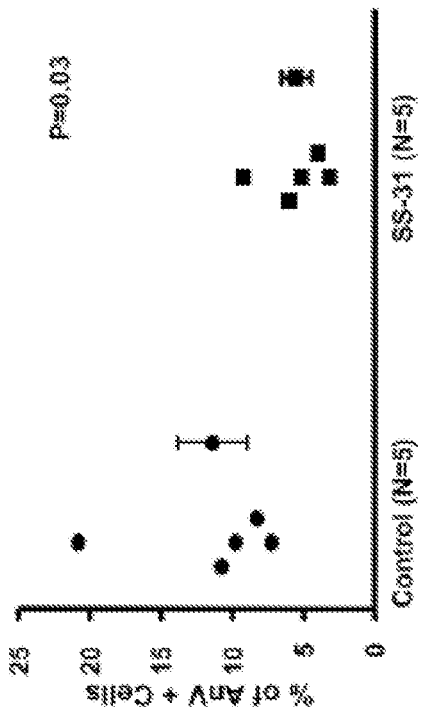
Figure 34A
Figure 34B

Figure 35C

| Treatment Group | Post-Transplantation | | | | |
|---|---|---|---|---|---|
| | Day 1 | Day 3 | Day 5 | Day 10 | Day 14 |
| Control (N=8 mice) | 7/8 | 0/8 | 0/8 | 1/8 | 0/8 |
| SS-31 Tx (N=10 mice) | 8/10 | 5/10 | 6/10 | 5/10 | 5/10 |
| P value | NS | 0.02 | 0.007 | 0.09 | 0.02 |

METHODS FOR REDUCING OXIDATIVE DAMAGE

CROSS-REFERENCE TO RELATED PATENT APPLICATIONS

This application is a continuation application of U.S. application Ser. No. 11/428,188, filed Jun. 30, 2006, which is a continuation application of U.S. application Ser. No. 11/040,242 filed on Jan. 21, 2005, now U.S. Pat. No. 7,550,439, which claims priority to U.S. Provisional Application No. 60/538,841 filed on Jan. 23, 2004. The specifications of U.S. application Ser. Nos. 11/428,188, 11/040,242 and 60/538,841 are hereby incorporated by reference in their entirety.

GOVERNMENT INTEREST

This invention was made with government support from the National Institute on Drug Abuse under Grant No. PO1 DA08924. The U.S. government has certain rights in this invention.

BACKGROUND OF THE INVENTION

Mitochondria are essential to cell survival as the main producers of ATP via oxidative phosphorylation. However, the mitochondria respirator chain is also a major source of oxidative free radicals. For example, radical production can occur as a result of the reaction of mitochondrial electron carriers, such as ubiquinol, with oxygen to form a superoxide. Superoxides react by dismutation to hydrogen peroxide, which can decompose to hydroxyl radical. In addition, superoxides react with nitric oxide to form peroxynitrite and other reactive oxidants.

Aging is associated not only with increased reactive oxygen species (ROS) production, but also a decrease in the endogenous antioxidant defense mechanisms. Mitochondria are particularly vulnerable to oxidative stress because they are continuously exposed to ROS. As a consequence, mitochondria decay is often associated with aging.

Free radicals, including ROS, and reactive nitrogen species (RNS) produce diverse non-specific damage to biological molecules, including lipids, proteins, RNA and DNA. Such damage of these molecules has been implicated in numerous clinical disorders, such as atherosclerosis, preeclampsia, Alzheimer's disease, Parkinson's disease and arthritis.

Antioxidant therapy can potentially delay the aging process, and be beneficial in a host of human diseases and conditions such as those described above. However, the development of specific mitochondrial therapies has been hampered by the difficulty of delivering antioxidant molecules to mitochondria in vivo. For example, the molecule must first be taken up across the plasma membrane into the cytoplasm, and then targeted selectively to mitochondria.

None of the currently available antioxidant compounds specifically target mitochondria. The endogenous antioxidants, superoxide dismutase and catalase, are poorly absorbed orally, have short half-lives, and do not cross the blood-brain barrier. The natural antioxidants (e.g., Vitamin E, coenzyme Q, polyphenols) are not water-soluble and tend to accumulate in cell membranes and only cross the blood-brain barrier slowly.

Therefore, there is a need for improved methods of reducing oxidative damage with antioxidative compounds that cross cell membranes. In addition, it would also be beneficial for the antioxidative compounds to specifically target mitochondria.

SUMMARY OF THE INVENTION

These and other objectives have been met by the present invention which provide a method for reducing oxidative damage in a mammal in need thereof. The method comprises administering to the mammal an effective amount of an aromatic cationic peptide. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 3a is the largest number that is less than or equal to $p_t+1$, except that when a is 1, $p_t$ may also be 1; and (f) at least one tyrosine or tryptophan amino acid.

In another embodiment, the invention also provides a method of reducing oxidative damage in a removed organ of a mammal. The method comprises administering to the removed organ an effective amount of an aromatic-cationic peptide. The aromatic-cationic peptide have (a) at least one net positive charge; (b) a minimum of four amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 2a is the largest number that is less than or equal to $p_t+1$, except that when a is 1, $p_t$ may also be 1; and (f) at least one tyrosine or tryptophan amino acid.

In a further embodiment, the invention provides a method of reducing oxidative damage in a mammal in need thereof. The method comprises administering) to the mammal an effective amount of an aromatic-cationic peptide. The aromatic-cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 2a is the largest number that is less than or equal to $p_t+1$, except that when a is 1, $p_t$ may also be 1, and (f) at least one tyrosine or tryptophan amino acid.

In yet a further embodiment the invention provides a method of reducing oxidative damage in a removed organ of a mammal. The method comprises administering to the removed organ an effective amount of an aromatic-cationic peptide. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 3a is the largest number that is less than or equal to $p_t+1$, except that when a is 1, $p_t$ may also be 1, and (f) at least one tyrosine or tryptophan amino acid.

In yet another embodiment, the invention provides a method of reducing, oxidative damage in a cell in need thereof. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein a is the largest number that is less than or equal to $p_t$+1, except that when a is 1, $p_t$ may also be 1, and (f) at least one tyrosine or tryptophan amino acid.

In an additional embodiment, the invention provides a method of reducing oxidative damage in a cell in need thereof. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 2a is the largest number that is less than or equal to $p_t$+1, except that when a is 1, $p_t$ may also be 1, and (f) at least one tyrosine or tryptophan amino acid.

BRIEF DESCRIPTION OF THE FIGURES

FIG. 4. (A) SS-02 inhibits mitochondrial production of hydrogen peroxide as measured by luminol chemiluminescence under basal conditions and upon stimulation by antimycin. (B) SS-02, SS-29, SS-30 and SS-31 reduced spontaneous generation of hydrogen peroxide generated by isolated mitochondria.

FIG. 6. SS-31 dose-dependently decreased intracellular ROS (reactive oxygen species) (A) and increased cell survival (B) in $N_2A$ cells exposed to a high dose of the pro-oxidant t-butyl hydroperoxide (t-BHP; 0.5 mM), (C) SS-02 also dose-dependently increased cell survival when N2A cells were exposed to 1 mM t-BHP.

FIG. 32. Effect of SS-31 peptide on ischemia-induced infarct size and swelling in C57BL/6 mice. Shown are representative serial sections (1.2 mm apart) stained with Cresyl Violet from mice subjected to 30 min (A) and 20 min (B) MCAO and treated with vehicle (Veh) or SS-31 (2 mg/kg body weight) immediately after reperfusion, 6 h, 24 h, and 48 h. Infarct volumes ((C) and swelling (D) were estimated at 72 h postischemia from 12 serial sections (600 Bm apart) per animal. Mean % cerebral blood flow (CBF) reduction during MCAO (E) and % reperfusion at 10 min postischemia (F) shows no difference between two groups. Error bars indicate SEM (n=11 animals per group). *p<0.05 from vehicle treated group (Veh), one-way ANOVA with post hoc Fisher's PLSD test.

DETAILED DESCRIPTION OF THE INVENTION

Figure 1A:
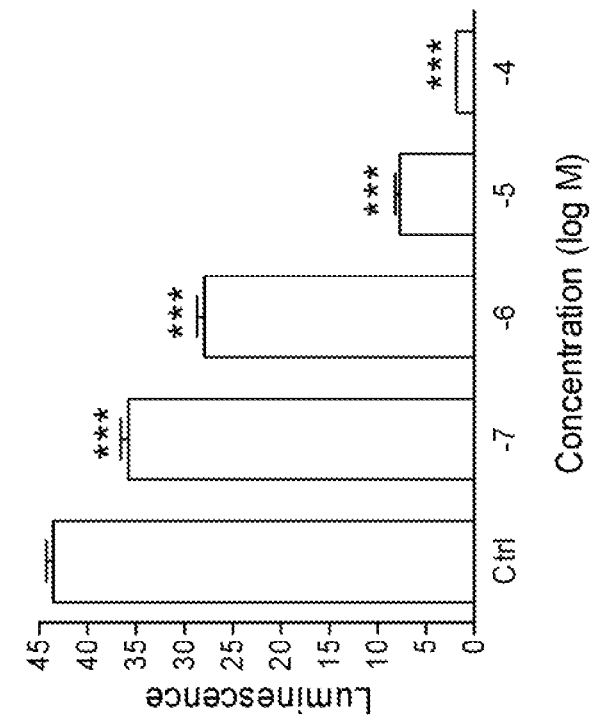
FIG. 1. (A) SS-02 and (B) SS-05 dose-dependently scavenge $H_2O_2$.

The invention is based on the surprising discovery by the inventors that certain aromatic-cationic peptides reduce oxidative damage. Reducing oxidative damage is important since free radicals, such as ROS and RNS, produce diverse non-specific damage to lipids, proteins. RNA, and DNA oxidative damage caused by free radicals is associated with several diseases and conditions in mammals.

Peptides

The aromatic-cationic peptides useful in the present invention are water-soluble and highly polar. Despite these properties, the peptides can readily penetrate cell membranes.

The aromatic-cationic peptides useful in the present invention include a minimum of three amino acids, and preferably include a minimum of four amino acids, covalently joined by peptide bonds.

The maximum number of amino acids present in the aromatic-cationic peptides of the present invention is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides useful in the present invention can be any amino acid. As used herein the term "amino acid" is used to refer to any organic molecule that contains at least one amino group and at least one carboxyl group. Preferably, at least one amino group is at the a position relative to the carboxyl group.

The amino acids may be naturally occurring. Naturally occurring amino acids include, for example, the twenty most common levorotatory (L) amino acids normally found in mammalian proteins, i.e., alanine (Ala), arginine (Arg), asparagine (Asn) aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), trypotophan, (Trp), tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea.

The peptides useful in the present invention can contain one or more non-naturally occurring amino acids. The non-naturally occurring amino acids may be L-, dextrorotatory (D), or mixtures thereof. Optimally, the peptide has no amino acids that are naturally occurring.

Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenyleacetic acid, and γ-phenyl -β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6' or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-naturally occurring amino acids. The D-amino acids do normally occur in proteins although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides useful in the methods of the invention should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids.

If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

It is important that at least one of the amino acids present in the aromatic-cationic peptide is a tyrosine or tryptophan residue, or a derivative thereof.

It is also important that the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r).

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH.

In one embodiment of the present invention, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment the relationship between the minimum number of net positive charges ($p_m$) ad the total number of amino acid residues (r) is as follows:

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine For example, the hexapeptide Lys-Gln-Tyr-Arg-Phe-Trp has a net positive charge of two (contributed by the lysine and arginine residues) and three aromatic groups (contributed by tyrosine, phenylalanine and tryptophan residues).

In one embodiment of the present invention, the aromatic-cationic peptides useful in the methods of the present invention have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

| (p+) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

| (p+) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are preferably amidated with, for example, ammonia to form the C-terminal amide, Alternatively, the terminal carboxyl group of the C-terminal amino acid may be amidated with any primary or secondary amine.

The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylyamido, N,N-diethylamido, N-methyl-N-ethylamido N-phenylamido or N-phenyl-N-ethylamido group.

The free carboxylate groups of the asparagine glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

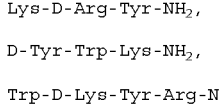

Lys-D-Arg-Tyr-NH$_2$,

D-Tyr-Trp-Lys-NH$_2$,

Trp-D-Lys-Tyr-Arg-NH$_2$,

-continued

Tyr-His-D-Gly-Met,

Tyr-D-Arg-Phe-Lys-Glu-NH₂,

Met-Tyr-D-Arg-Phe-Arg,

D-His-Glu-Lys-Tyr-D-Phe-Arg,

Lys-D-Gln-Tyr-Arg-D-Phe-Trp-NH₂,

Phe-D-Arg-Lys-Trp-Tyr-D-Arg-His,

Gly-D-Phe-Lys-His-D-Arg-Tyr-NH2,

Val-D-Lys-His-Tyr-D-Phe-Ser-Tyr-Arg-NH₂,

Trp-Lys-Phe-D-Asp-Arg-Tyr-D-His-Lys,

Lys-Trp-D-Tyr-Arg-Asn-Phe-Tyr-D-His-NH₂,

Thr-Gly-Tyr-Arg-D-His-Phe-Trp-D-His-Lys,

Asp-D-Trp-Lys-Tyr-D-His-Phe-Arg-D-Gly-Lys-NH₂,

D-His-Lys-Tyr-D-Phe-Glu-D-Asp-D-Asp-D-His-D-Lys-Arg-Trp-NH₂,

Ala-D-Phe-D-Arg-Tyr-Lys-D-Trp-His-D-Tyr-Gly-Phe,

Tyr-D-His-Phe-D-Arg-Asp-Lys-D-Arg-His-Trp-D-His-Phe,

Phe-Phe-D-Tyr-Arg-Glu-Asp-D-Lys-Arg-D-Arg-His-Phe-NH₂,

Phe-Tyr-Lys-D-Arg-Trp-His-D-Lys-D-Lys-Glu-Arg-D-Tyr-Thr,

Tyr-Asp-D-Lys-Tyr-Phe-D-Lys-D-Arg-Phe-Pro-D-Tyr-His-Lys,

Glu-Arg-D-Lys-Tyr-D-Val-Phe-D-His-Trp-Arg-D-Gly-Tyr-Arg-D-Met-NH₂,

Arg-D-Leu-D-Tyr-Phe-Lys-Glu-D-Lys-Arg-D-Trp-Lys-D-Phe-Tyr-D-Arg-Gly,

D-Glu-Asp-Lys-D-Arg-D-His-Phe-Phe-D-Val-Tyr-Arg-Tyr-D-Tyr-Arg-His-Phe-NH₂,

Asp-Arg-D-Phe-Cys-Phe-D-Arg-D-Lys-Tyr-Arg-D-Tyr-Trp-D-His-Tyr-D-Phe-Lys-Phe,

His-Tyr-D-Arg-Trp-Lys-Phe-D-Asp-Ala-Arg-Cys-D-Tyr-His-Phe-D-Lys-Tyr-His-Ser-NH₂,

Gly-Ala-Lys-Phe-D-Lys-Glu-Arg-Tyr-His-D-Arg-D-Arg-Asp-Tyr-Trp-D-His-Trp-His-D-Lys-Asp,
and Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH₂.

In one embodiment, the peptides useful in the methods of the present invention have mu-opioid receptor agonist activity (i.e., activate the mu-opioid receptor). Activation of the mu-opioid receptor typically elicits an analgesic effect.

In certain instances, an aromatic-cationic peptide having mu-opioid receptor activity is preferred. For example, during short-term treatment, such as in an acute disease or condition, it may be beneficial to use an aromatic-cationic peptide that activates the mu-opioid receptor. For example, the acute diseases and conditions can be associated with moderate or severe pain. In these instances, the analgesic effect of the aromatic-cationic peptide may be beneficial in the treatment regiment of the patient or other mammal, although an aromatic-cationic peptide which does not activate the mu-opioid receptor may also be used with or without an analgesic according to clinical requirements.

Alternatively, in other instances, an aromatic-cationic peptide that does not have mu-opioid receptor activity is preferred. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patients or other mammal.

Potential adverse effects may include sedation, constipation, nervous system depression and respiratory depression. In such instances aromatic-cationic peptide that does not activate the mu-opioid receptor may be an appropriate treatment.

Examples of acute conditions include heart attack, stroke and traumatic injury. Traumatic injury may include traumatic brain and spinal cord injury.

Examples of chronic diseases or conditions include coronary artery disease and any neurodegenerative disorders, such as those described below.

Peptides useful in the methods of the present invention which have mu-opioid receptor activity are typically those peptides which have a trysine residue or a tyrosine derivative at the N-terminus (i.e., the first amino acid position). Preferred derivatives of tyrosine include 2'-methyltyrosine (Mmt); 2',6'-dimethlyltyrosine (2',6'Dmt), 3',5'-dimethyltryosine (3'5'Dmt); N,2',6'-trimethyltyrosine (Tmt); and 2'-hydroxy-6'-methyltryrosine (Hmt).

In a particular preferred embodiment, a peptide that has mu-opioid receptor activity has the formula Tyr-D-Arg-Phe-Lys-NH₂ (for convenience represented by the acronym: DALDA, which is referred to herein as SS-01. DALDA has a net positive charge of three, contributed by the amino acids tyrosine, arginine, and lysine and has two aromatic groups contributed by the amino acids phenylalanine and tyrosine. The tyrosine of DALDA can be a modified derivative of tyrosine such as in 2',6'-dimethyltyrosine to produce the compound having the formula 2',6'-Dmt-Arg-Phe-Lys-NH₂ (i.e., Dmt¹-DALDA, which is referred to herein as SS-02).

Peptides that do not have mu-opioid receptor activity generally do not have a tyrosine residue or a derivative of tyrosine at the N-terminus (i.e., amino acid position one). The amino acid at the N-terminus can be any naturally occurring or non-naturally occurring amino acid other than tyrosine.

In one embodiment, the amino acid at the N-terminus is phenylalanine or its derivative. Preferred derivatives of phenylalanine include 2'-methylphenylalanine (Mmp), 2',6'-dimethylphenylalanine (Dmp), N,2',6'-trimethylphenylalanine (Tmp) and 2'-hydroxy-6'-methylphenylalanine (Hmp). In another preferred embodiment, the amino acid residue at the N-terminus is arginine. An example of such a peptide is D-Arg-2'6'-Dmt-Lys-Phe-NH₂ (referred to in this specification as SS-31).

Another aromatic-cationic peptide that does not have mu-opioid receptor activity has the formula Phe-D-Arg-Dmt-Lys-NH₂. Alternatively, the N-terminal phenylalanine can be a derivative of phenylalanine such as 2',6'-dimethylphenylalanine (2'6'Dmp). DALDA containing 2',6'-dimethylphenylalanine at amino acid position one has the formula 2',6'-Dmp-D-Arg-Dmt-Lys-NH$_2$.

In a preferred embodiment, the amino acid sequence of Dmt$^1$-DALDA (SS-02) is rearranged such that Dmt is not at the N-terminus. An example of such an aromatic-cationic peptide that does not have mu-opioid receptor activity has the formula D-Arg-2'6'Dmt-Lys-Phe-NH$_2$ (SS-31).

DALDA, SS-31, and their derivatives can further include functional analogs. A peptide is considered a functional analog of DALDA or SS-31 if the analog has the same function as DALDA or SS-31. The analog may, for example, be a substitution variant of DALDA or SS-31, wherein one or more amino acid is substituted by another amino acid.

Suitable substitution variants of DALDA or SS-31 include conservative amino acid substitutions. Amino acids may be grouped according to their physicochemical characteristics as follows:

(a) Non-polar amino acids: Ala(A) Ser(S) Thr(T) Pro(P) Gly(G);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val(V); and
(e) Aromatic amino acids: Phe(F) Tyr(Y) Trp(W) His(H).

Substitutions of an amino acid link peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of analogs useful in the practice of the present invention that activate mu-opioid receptors include, but are not limited to, the aromatic-cationic peptides shown in Table 1.

TABLE 1

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | NH$_2$ |
| Tyr | D-Arg | Phe | Orn | | NH$_2$ |
| Tyr | D-Arg | Phe | Dab | | NH$_2$ |
| Tyr | D-Arg | Phe | Dap | | NH$_2$ |
| 2'6'Dmt | D-Arg | Phe | Lys | | NH$_2$ |
| 2'6'Dmt | D-Arg | Phe | Lys | Cys | NH$_2$ |
| 2'6'Dmt | D-Arg | Phe | Lys-NH(CH$_2$)$_2$—NH-dns | | NH$_2$ |
| 2'6'Dmt | D-Arg | Phe | Lys-NH(CH$_2$)$_2$—NH-atn | | NH$_2$ |
| 2'6'Dmt | D-Arg | Phe | dnsLys | | NH$_2$ |
| 2'6'Dmt | D-Cit | Phe | Lys | | NH$_2$ |
| 2'6'Dmt | D-Cit | Phe | Ahp | | NH$_2$ |
| 2'6'Dmt | D-Arg | Phe | Orn | | NH$_2$ |
| 2'6'Dmt | D-Arg | Phe | Dab | | NH$_2$ |
| 2'6'Dmt | D-Arg | Phe | Dap | | NH$_2$ |
| 2'6'Dmt | D-Arg | Phe | Ahp(2-aminoheptanoic acid) | | NH$_2$ |
| Bio-2'6'Dmt | D-Arg | Phe | Lys | | NH$_2$ |
| 3'5'Dmt | D-Arg | Phe | Lys | | NH$_2$ |
| 3'5'Dmt | D-Arg | Phe | Orn | | NH$_2$ |
| 3'5'Dmt | D-Arg | Phe | Dab | | NH$_2$ |
| 3'5'Dmt | D-Arg | Phe | Dap | | NH$_2$ |
| 3'5'Dmt | D-Arg | Tyr | Lys | | NH$_2$ |
| Tyr | D-Arg | Tyr | Orn | | NH$_2$ |
| Tyr | D-Arg | Tyr | Dab | | NH$_2$ |
| Tyr | D-Arg | Tyr | Dap | | NH$_2$ |
| 2'6'Dmt | D-Arg | Tyr | Lys | | NH$_2$ |
| 2'6'Dmt | D-Arg | Tyr | Orn | | NH$_2$ |
| 2'6'Dmt | D-Arg | Tyr | Dab | | NH$_2$ |
| 2'6'Dmt | D-Arg | Tyr | Dap | | NH$_2$ |
| 2'6'Dmt | D-Arg | 2'6'Dmt | Lys | | NH$_2$ |
| 2'6'Dmt | D-Arg | 2'6'Dmt | Orn | | NH$_2$ |
| 2'6'Dmt | D-Arg | 2'6'Dmt | Dab | | NH$_2$ |
| 2'6'Dmt | D-Arg | 2'6'Dmt | Dap | | NH$_2$ |
| 3'5'Dmt | D-Arg | 3'5'Dmt | Arg | | NH$_2$ |
| 3'5'Dmt | D-Arg | 3'5'Dmt | Lys | | NH$_2$ |
| 3'5'Dmt | D-Arg | 3'5'Dmt | Orn | | NH$_2$ |
| 3'5'Dmt | D-Arg | 3'5'Dmt | Dab | | NH$_2$ |
| Tyr | D-Lys | Phe | Dap | | NH$_2$ |
| Tyr | D-Lys | Phe | Arg | | NH$_2$ |
| Tyr | D-Lys | Phe | Lys | | NH$_2$ |
| Tyr | D-Lys | Phe | Orn | | NH$_2$ |
| 2'6'Dmt | D-Lys | Phe | Dab | | NH$_2$ |
| 2'6'Dmt | D-Lys | Phe | Dap | | NH$_2$ |
| 2'6'Dmt | D-Lys | Phe | Arg | | NH$_2$ |
| 2'6'Dmt | D-Lys | Phe | Lys | | NH$_2$ |
| 2'6'Dmt | D-Lys | Phe | Orn | | NH$_2$ |
| 2'6'Dmt | D-Lys | Phe | Dab | | NH$_2$ |
| 2'6'Dmt | D-Lys | Phe | Dap | | NH$_2$ |
| 2'6'Dmt | D-Lys | Phe | Arg | | NH$_2$ |
| 3'5'Dmt | D-Lys | Phe | Orn | | NH$_2$ |
| 3'5'Dmt | D-Lys | Phe | Dab | | NH$_2$ |
| 3'5'Dmt | D-Lys | Phe | Dap | | NH$_2$ |
| 3'5'Dmt | D-Lys | Phe | Arg | | NH$_2$ |
| Tyr | D-Lys | Tyr | Lys | | NH$_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Lys | Tyr | Orn | | NH$_2$ |
| Tyr | D-Lys | Tyr | Dab | | NH$_2$ |
| Tyr | D-Lys | Tyr | Dap | | NH$_2$ |
| 2'6'Dmt | D-Lys | Tyr | Lys | | NH$_2$ |
| 2'6'Dmt | D-Lys | Tyr | Orn | | NH$_2$ |
| 2'6'Dmt | D-Lys | Tyr | Dab | | NH$_2$ |
| 2'6'Dmt | D-Lys | Tyr | Dap | | NH$_2$ |
| 2'6'Dmt | D-Lys | 2'6'Dmt | Lys | | NH$_2$ |
| 2'6'Dmt | D-Lys | 2'6'Dmt | Orn | | NH$_2$ |
| 2'6'Dmt | D-Lys | 2'6'Dmt | Dab | | NH$_2$ |
| 2'6'Dmt | D-Lys | 2'6'Dmt | Dap | | NH$_2$ |
| 2'6'Dmt | D-Arg | Phe | dnsDap | | NH$_2$ |
| 2'6'Dmt | D-Arg | Phe | atnDap | | NH$_2$ |
| 3'5'Dmt | D-Lys | 3'5'Dmt | Lys | | NH$_2$ |
| 3'5'Dmt | D-Lys | 3'5'Dmt | Orn | | NH$_2$ |
| 3'5'Dmt | D-Lys | 3'5'Dmt | Dab | | NH$_2$ |
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dab | Phe | Arg | | NH$_2$ |
| Tyr | D-Dap | Phe | Arg | | NH$_2$ |
| 2'6'Dmt | D-Arg | Phe | Arg | | NH$_2$ |
| 2'6'Dmt | D-Lys | Phe | Arg | | NH$_2$ |
| 2'6'Dmt | D-Orn | Phe | Arg | | NH$_2$ |
| 2'6'Dmt | D-Dab | Phe | Arg | | NH$_2$ |
| 3'5'Dmt | D-Dap | Phe | Arg | | NH$_2$ |
| 3'5'Dmt | D-Arg | Phe | Arg | | NH$_2$ |
| 3'5'Dmt | D-Lys | Phe | Arg | | NH$_2$ |
| 3'5'Dmt | D-Orn | Phe | Arg | | NH$_2$ |
| Tyr | D-Lys | Tyr | Arg | | NH$_2$ |
| Tyr | D-Orn | Tyr | Arg | | NH$_2$ |
| Tyr | D-Dab | Tyr | Arg | | NH$_2$ |
| Tyr | D-Dap | Tyr | Arg | | NH$_2$ |
| 2'6'Dmt | D-Arg | 2'6'Dmt | Arg | | NH$_2$ |
| 2'6'Dmt | D-Lys | 2'6'Dmt | Arg | | NH$_2$ |
| 2'6'Dmt | D-Orn | 2'6'Dmt | Arg | | NH$_2$ |
| 2'6'Dmt | D-Dab | 2'6'Dmt | Arg | | NH$_2$ |
| 3'5'Dmt | D-Dap | 3'5'Dmt | Arg | | NH$_2$ |
| 3'5'Dmt | D-Arg | 3'5'Dmt | Arg | | NH$_2$ |
| 3'5'Dmt | D-Lys | 3'5'Dmt | Arg | | NH$_2$ |
| 3'5'Dmt | D-Orn | 3'5'Dmt | Arg | | NH$_2$ |
| Mmt | D-Arg | Phe | Lys | | NH$_2$ |
| Mmt | D-Arg | Phe | Orn | | NH$_2$ |
| Mmt | D-Arg | Phe | Dab | | NH$_2$ |
| Mmt | D-Arg | Phe | Dap | | NH$_2$ |
| Tmt | D-Arg | Phe | Lys | | NH$_2$ |
| Tmt | D-Arg | Phe | Orn | | NH$_2$ |
| Tmt | D-Arg | Phe | Dab | | NH$_2$ |
| Tmt | D-Arg | Phe | Dap | | NH$_2$ |
| Hmt | D-Arg | Phe | Lys | | NH$_2$ |
| Hmt | D-Arg | Phe | Orn | | NH$_2$ |
| Hmt | D-Arg | Phe | Dab | | NH$_2$ |
| Hmt | D-Arg | Phe | Dap | | NH$_2$ |
| Mmt | D-Lys | Phe | Lys | | NH$_2$ |
| Mmt | D-Lys | Phe | Orn | | NH$_2$ |
| Mmt | D-Lys | Phe | Dab | | NH$_2$ |
| Mmt | D-Lys | Phe | Dap | | NH$_2$ |
| Mmt | D-Lys | Phe | Arg | | NH$_2$ |
| Tmt | D-Lys | Phe | Lys | | NH$_2$ |
| Tmt | D-Lys | Phe | Orn | | NH$_2$ |
| Tmt | D-Lys | Phe | Dab | | NH$_2$ |
| Tmt | D-Lys | Phe | Dap | | NH$_2$ |
| Tmt | D-Lys | Phe | Arg | | NH$_2$ |
| Hmt | D-Lys | Phe | Lys | | NH$_2$ |
| Hmt | D-Lys | Phe | Orn | | NH$_2$ |
| Hmt | D-Lys | Phe | Dab | | NH$_2$ |
| Hmt | D-Lys | Phe | Dap | | NH$_2$ |
| Hmt | D-Lys | Phe | Arg | | NH$_2$ |
| Mmt | D-Lys | Phe | Arg | | NH$_2$ |
| Mmt | D-Orn | Phe | Arg | | NH$_2$ |
| Mmt | D-Dab | Phe | Arg | | NH$_2$ |
| Mmt | D-Dap | Phe | Arg | | NH$_2$ |
| Mmt | D-Arg | Phe | Arg | | NH$_2$ |
| Tmt | D-Lys | Phe | Arg | | NH$_2$ |
| Tmt | D-Orn | Phe | Arg | | NH$_2$ |
| Tmt | D-Dab | Phe | Arg | | NH$_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tmt | D-Dap | Phe | Arg | | $NH_2$ |
| Tmt | D-Arg | Phe | Arg | | $NH_2$ |
| Hmt | D-Lys | Phe | Arg | | $NH_2$ |
| Hmt | D-Orn | Phe | Arg | | $NH_2$ |
| Hmt | D-Dab | Phe | Arg | | $NH_2$ |
| Hmt | D-Dap | Phe | Arg | | $NH_2$ |
| Hmt | D-Arg | Phe | Arg | | $NH_2$ |

Dab = diaminobutyric acid
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of analogs useful in the practice of the present invention that do not activate mu-opioid receptors include, but are not limited to, the aromatic-cationic peptides shown in Table 2.

TABLE 2

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| D-Arg | Dmt | Lys | Phe | | $NH_2$ |
| D-Arg | Dmt | Phe | Lys | | $NH_2$ |
| D-Arg | Phe | Lys | Dmt | | $NH_2$ |
| D-Arg | Phe | Dmt | Lys | | $NH_2$ |
| D-Arg | Lys | Dmt | Phe | | $NH_2$ |
| D-Arg | Lys | Phe | Dmt | | $NH_2$ |
| Phe | Lys | Dmt | D-Arg | | $NH_2$ |
| Phe | Lys | D-Arg | Dmt | | $NH_2$ |
| Phe | D-Arg | Dmt | Lys | | $NH_2$ |
| Phe | D-Arg | Lys | Dmt | | $NH_2$ |
| Phe | Dmt | D-Arg | Lys | | $NH_2$ |
| Phe | Dmt | Lys | D-Arg | | $NH_2$ |
| Lys | Phe | D-Arg | Dmt | | $NH_2$ |
| Lys | Phe | Dmt | D-Arg | | $NH_2$ |
| Lys | Dmt | D-Arg | Phe | | $NH_2$ |
| Lys | Dmt | Phe | D-Arg | | $NH_2$ |
| Lys | D-Arg | Phe | Dmt | | $NH_2$ |
| Lys | D-Arg | Dmt | Phe | | $NH_2$ |
| D-Arg | Dmt | D-Arg | Phe | | $NH_2$ |
| D-Arg | Dmt | D-Arg | Dmt | | $NH_2$ |
| D-Arg | Dmt | D-Arg | Tyr | | $NH_2$ |
| D-Arg | Dmt | D-Arg | Trp | | $NH_2$ |
| Trp | D-Arg | Phe | Lys | | $NH_2$ |
| Trp | D-Arg | Tyr | Lys | | $NH_2$ |
| Trp | D-Arg | Trp | Lys | | $NH_2$ |
| Trp | D-Arg | Dmt | Lys | | $NH_2$ |
| D-Arg | Trp | Lys | Phe | | $NH_2$ |
| D-Arg | Trp | Phe | Lys | | $NH_2$ |
| D-Arg | Trp | Lys | Dmt | | $NH_2$ |
| D-Arg | Trp | Dmt | Lys | | $NH_2$ |
| D-Arg | Lys | Trp | Phe | | $NH_2$ |
| D-Arg | Lys | Trp | Dmt | | $NH_2$ |
| | | | | | $NH_2$ |

The amino acids of the peptides shown in table 1 and 2 may be in either the L- or the D-configuration.

Methods of Reducing Oxidative Damage

The peptides described above are useful in reducing oxidative damage in a mammal in need thereof. Mammals in need of reducing oxidative damage are those mammals suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO), superoxide anion radical ($O_2^-$) nitric oxide (NO) hydrogen peroxide ($H_2O_2$), hypochlorous acid (HOCl) and peroxynitrite anion. ($ONOO^-$).

In one embodiment, a mammal in need thereof may be a mammal undergoing a treatment associated with oxidative damage. For example, the mammal may be undergoing reperfusion. Reperfusion refers to the restoration of blood flow to any organ or tissue in which the flow of blood is decreased or blocked. The restoration of blood flow during reperfusion leads to respiratory burst and formation of free radicals.

Decreased or blocked blood flow may be due to hypoxia or ischemia. The loss or severe reduction in blood supply during hypoxia or ischemia may, for example, be due to thromboembolic stroke, coronary atherosclerosis, or peripheral vascular disease.

Numerous organs and tissues are subject to ischemia or hypoxia. Examples of such organs include brain, heart, kidney, intestine and prostate. The tissue affected is typically muscle, such as cardiac, skeletal, or smooth muscle. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages.

The restoration of blood flow (reperfusion) can occur by any method known to those in the art. For instance, reperfusion of ischemic cardiac tissues may arise from angioplasty, coronary artery bypass graft, or the use of thrombolytic drugs. Reducing oxidative damage associated with ischemia/hypoxia and reperfusion is important because the tissue damage associated with ischemia/hypoxia and reperfusion is associated with, for example, myocardial infarction, stroke and hemorrhagic shock.

In another embodiment, a mammal in need thereof can be a mammal with a disease or condition associated with oxidative damage. The oxidative damage can occur in any cell, tissue or organ of the mammal. Examples of cells, tissues or organs include, but are not limited to, endothelial cells, epithelial cells, nervous system cells, skin, heart, lung, kidney and liver. For example, lipid peroxidation and an inflammatory process are associated with oxidative damage for a disease or condition.

Lipid peroxidation refers to oxidative modification of lipids. The lipids can be present in the membrane of a cell. This modification of membrane lipids typically results in change and/or damage to the membrane function of a cell. In addition, lipid peroxidation can also occur in lipids or lipoproteins exogenous of a cell. For example, low-density lipoproteins are susceptible to lipid per-oxidation. An example of a condition associated with lipid peroxidation is atherosclerosis. Reducing oxidative damage associated with atherosclerosis is important since atherosclerosis is implicated in, for example, heart attacks and coronary artery disease.

Inflammatory process refers to the activation of the immune system. Typically, the immune system is activated by an antigenic substance. The antigenic substance can be any substance recognized by the immune system, and include self-derived particles and foreign-derived particles. Examples of diseases or conditions occurring from an inflammatory process to self-derived particles include arthritis and multiple sclerosis. Examples of foreign particles include viruses and bacteria.

The virus can be any virus which activates an inflammatory process, and associated with oxidative damage. Examples of viruses include, hepatitis A, B or C virus, human immunodeficiency virus, influenza virus, and bovine diarrhea virus. For example, hepatitis virus can elicit an inflammatory process and formation of free radicals, thereby damaging the liver.

The bacteria can be any bacteria, and include gram-negative or gram-positive bacteria. Gram-negative bacteria contain lipopolysaccharide in the bacteria wall. Examples of gram-negative bacterial include *Escherichia coli, Klebsiella pneumoniae, Proteus* species, *Pseudomonas aeruginosa, Serratia*, and *Bacteroides*. Examples of gram-positive bacteria include pneumococci and streptococci.

An example of an inflammatory process associated with oxidative stress caused by a bacteria is sepsis. Typically, sepsis occurs when gram-negative bacteria enter the bloodstream.

Liver damage caused by a toxic agent is another condition associated with an inflammatory process and oxidative stress. The toxic agent can be any agent which causes damage to the liver. For example, the toxic agent can cause apoptosis and/or necrosis of liver cells. Examples of such agents include alcohol, and medication, such as prescription and non-prescription drugs taken to treat a disease or condition.

The methods of the present invention can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes and microglia.

The neurodegenerative condition can be an acute condition, such as a stroke or a traumatic brain or spinal cord injury. In another embodiment, the neurodegenerative disease or condition can be a chronic neurodegenerative condition. In a chronic neurodegenerative condition, the free radicals can, for example, cause damage to a protein. An example of such a protein is amyloid β-protein. Examples of chronic neurodegenerative diseases associated with damage by free radicals include Parkinson's disease, Alzheimer's disease, Huntington's disease and Amyotrophic Lateral Sclerosis (also known as Lou Gherig's disease).

Other conditions which can be treated in accordance with the present invention include preeclampsia, diabetes, and symptoms of and conditions associated with aging, such as macular degeneration, wrinkles.

In another embodiment, the peptides useful in the present invention may also be used in reducing oxidative damage in an organ of a mammal prior to transplantation. For example, a removed organ, when subjected to reperfusion after transplantation can be susceptible to oxidative damage. Therefore, the peptides can be used to reduce oxidative damage from reperfusion of the transplanted organ.

The removed organ can be any organ suitable for transplantation. Examples of such organs include, the heart, liver, kidney, lung, and pancreatic islets. The removed organ is placed in a suitable medium, such as in a standard buffered solution commonly used in the art.

For example, a removed heart can be placed in a cardioplegic solution containing the peptides described above. The concentration of peptides in the standard buffered solution can be easily determined by those skilled in the art. Such concentrations may be, for example, between about 0.01 nM to about 10 µM, preferably about 0.1 nM to about 10 µM, more preferably about 1 µM to about 5 µM, and even more preferably about 1 nM to about 100 nM.

In yet another embodiment, the invention provides a method for reducing oxidative damage in a cell in need thereof. Cells in need of reducing oxidative damage are generally those cells in which the cell membrane or DNA of the cell has been damaged by free radicals, for example, ROS and/or RNS. Examples of cells capable of being subjected to oxidative damage include the cells described herein. Suitable examples of cells include pancreatic islet cells, myocytes, endothelial cells, neuronal cells, stem cells, etc.

The cells can be tissue culture cells. Alternatively the cells may be obtained from a mammal. In one instance, the cells can be damaged by oxidative damage as a result of an insult. Such insults include, for example, a disease or condition (e.g., diabetes, etc.) or ultraviolet radiation (e.g., sun, etc.). For example pancreatic islet cells damaged by oxidative damage as a result of diabetes can be obtained from a mammal.

The peptides described above can be administered to the cells by any method known to those skilled in the art. For example, the peptides can be incubated with the cells under suitable conditions. Stick conditions can be readily determined by those skilled in the art.

Due to reduction of oxidative damage, the treated cells may be capable of regenerating. Such regenerated cells may be administered back into the mammal as a therapeutic treatment for a disease or condition. As mentioned above, one such condition is diabetes.

Oxidative damage is considered to be "reduced" if the amount of oxidative damage in a mammal, a removed organ, or a cell is decreased after administration of an effective amount of the aromatic cationic peptides described above. Typically, the oxidative damage is considered to be reduced if the oxidative damage is decreased by at least about 10%, preferably at least about 25%, more preferably at least about 50%, even more preferably at least about 75%, and most preferably at least about 90%.

Synthesis of the Peptides

The peptides useful in the methods of the present invention may be chemically synthesized by any of the methods well known in the art. Suitable methods for synthesizing the protein include, for example those described by Stuart and Young in "Solid Phase Peptide Synthesis," Second Edition, Pierce Chemical Company (1984), and in "Solid Phase Peptide Synthesis," *Methods Enzymol.* 289, Academic Press, Inc, New York (1997).

Modes of Administration

The peptide useful in the methods of the present invention is administered to a mammal in an amount effective in reducing oxidative damage. The effective amount is determined during pre-clinical trials and clinical trials by methods familiar to physicians and clinicians.

An effective amount of a peptide useful in the methods of the present invention, preferably in a pharmaceutical composition, may be administered to a mammal in need thereof by any of a number of well-known methods for administering pharmaceutical compounds.

The peptide may be administered systemically or locally. In one embodiment, the peptide is administered intravenously. For example, the aromatic-cationic peptides useful in the methods of the present invention may be administered via rapid intravenous bolus injection. Preferably, however, the peptide is administered as a constant rate intravenous infusion.

The peptide can be injected directly into coronary artery during for example, angioplasty of or coronary bypass surgery, or applied onto coronary stents.

The peptide may also be administered orally, topically, intranasally, intramuscularly, subcutaneously, or transdermally. In a preferred embodiment, transdermal administration of the aromatic-cationic peptides by methods of the present invention is by iontophoresis, in which the charged peptide is delivered across the skin by an electric current.

Other routes of administration include intracerebroventricularly or intrathecally. intracerebroventiculatly refers to administration into the ventricular system of the brain. Intrathecally refers to administration into the space under the arachnoid membrane of the spinal cord. This intracerebroventicular or intrathecal administration may be preferred for those diseases and conditions which affect the organs or tissues of the central nervous system. In a preferred embodiment, intrathecal administration is used for traumatic spinal cord injury.

The peptides useful in the methods of the invention may also be administered to mammals by sustained release as is known in the art. Sustained release administration is a method of drug delivery to achieve a certain level of the drug over a particular period of time. The level typically is measured by serum or plasma concentration.

A description of methods for delivering a compound by controlled release can be found in PCT Application No. WO 02/083106. The PCT application is incorporated herein by reference in its entirety.

Any formulation known in the art of pharmacy is suitable for administration of the aromatic-cationic peptides useful in the methods of the present invention. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the aromatic-cationic peptides useful in the methods of the present invent oils may utilize conventional diluents, carriers, or excipients etc., such as are known in the art can be employed to deliver the peptides. For example, the formulations may comprise one or more of the following: a stabilizing a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the peptide.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buttering agent may be any salt or buffering agent such as for example, sodium chloride, or sodium/potassium phosphate, respectively. Preferably, the buttering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the peptides useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal treated in accordance with the invention can be any mammal, including, for example, farm animals, such as sheep, pigs, cows, and horses pet animals such as dogs and cats, laboratory animals, such as rats, mice and rabbits. In a preferred embodiment, the mammal is a human.

EXAMPLES

Example 1

[Dmt$^1$]DALDA Penetrates Cell Membrane

The cellular uptake of [$^3$H][Dmt$^1$]DALDA was studied using a human intestinal epithelial cell line (Caco-2), and confirmed with SH-SY5Y (human neuroblastoma cell), HEK293 (human embryonic kidney cell) and CRFK cells (kidney epithelial cell). Monolayers of cells were grown on 12-well plates (5×10$^5$ cells/well) coated with collagen for 3 days. On day 4, cells were washed twice with pre-warmed HBSS, and then incubated with 0.2 ml of HBSS containing either 250 nM [$^3$H][Dmt$^1$]DALDA at 37° C. for 4° C. for various times up to 1 h.

[$^3$H][Dmt$^1$]DALDA was observed in cell lysate as early as 5 min, and steady state levels were achieved by 30 min. The total amount of [$^3$H][Dmt$^1$]DALDA recovered in the cell lysate after 1 h incubation represented about 1% of the total drug. The uptake of [$^3$H][Dmt$^1$]DALDA was slower at 4° C. compared to 37° C., but reached 76.5% by 45 min and 86.3% by 1 h. The internalization of [$^3$H][Dmt$^1$]DALDA was not limited to Caco-2 cells, but was also observed in SH-SY5Y, HEK293 and CRFK cells. The intracellular concentration of [Dmt$^1$]DALDA was estimated to be approximately 50 times higher than extracellular concentration.

In a separate experiment, cells were incubated with a range of [Dmt$^1$]DALDA concentrations (1 µM-3 mM) for 1 h at 37° C. At the end of the incubation period, cells were washed 4 times with HBSS, and 0.2 ml of 0.1N NaOH with 1% SDS was added to each well. The cell contents were then transferred to scintillation vials and radioactivity counted. To distinguish between internalized radioactivity from surface-associated radioactivity, an acid-wash step was included. Prior to cell lysis, cells were incubated with 0.2 ml of 0.2 M acetic acid/0.05 M NaCl for 5 min on ice.

The uptake of [Dmt$^1$]DALDA into Caco-2 cells was confirmed by confocal laser scanning microscopy (CLSM) using a fluorescent analog of [Dmt$^1$]DALDA (Dmt-D-Arg-Phe-dnsDap-NH$_2$; where dnsDap=β-dansyl-1-α,β-diaminopropionic acid). Cells were grown as described above and were plated on (35 mm) glass bottom dishes (MatTek Corp., Ashland, Mass.) for 2 days. The medium was then removed and cells were incubated with 1 ml of HBSS containing 0.1 µM to 1.0 µM of the fluorescent peptide analog at 37° C. for 1 h. Cells were then washed three times with ice-cold HBSS and covered with 200 µl of PBS, and microscopy was performed within 10 min at room temperature using a Nikon confocal laser scanning microscope with a C-Apochromat 63x/1.2W corr objective. Excitation was performed at 340 nm by means of a UV laser, and emission was measured at 520 nm. For optical sectioning in z-direction, 5-10 frames with 2.0 µm were made.

CLSM confirmed the uptake of fluorescent Dmt-D-Arg-Phe-dnsDap-NH$_2$ into Caco-2 cells after incubation with 0.1 µM [Dmt$^1$,DnsDap$^4$]DALDA for 1 h at 37° C. The uptake of the fluorescent peptide was similar at 37° C. and 4° C. The fluorescence appeared diffuse throughout the cytoplasm but was completely excluded from the nucleus.

Example 2

Targeting of [Dmt$^1$]DALDA to Mitochondria

To examine the subcellular distribution of [Dmt$^1$]DALDA, the fluorescent analog, [Dmt$^1$, AtnDap$^4$]DALDA (Dmt-D-Arg-Phe-atnDap-NH$_2$; where atn=β-anthraniloyl-1-α,β-diamino-propionic acid) was prepared. The analog contained β-anthraniloyl-1-α,β-diaminopropionic acid in place of the lysine reside at position 4. The cells were grown as described in Example 1 and were plated on (35 mm) glass bottom dishes (MatTek Corp., Ashland, Mass.) for 2 days. The medium was then removed and cells were incubated with 1 ml of HBSS containing 0.1 µM of [Dmt$^1$,AtnDap$^4$]DALDA at 37° C. for 15 min to 1 h.

Cells were also incubated with tetramethylrhodamine methyl ester (TMRM, 25 nM), a dye for staining mitochondria, for 15 min at 37° C. Cells were then washed three times with ice-cold HBSS and covered with 200 µl of PBS, and microscopy was performed within 10 min at room temperature using a Nikon confocal laser scanning microscope with a C-Apochromat 63x/1.2W corr objective.

For [Dmt$^1$,AtnDap$^4$]DALDA, excitation was performed at 350 nm by means of a UV laser, and emission was measured at 520 nm. For TMRM, excitation was performed at 356 nm, and emission was measured at 560 nm.

CLSM showed the uptake of fluorescent [Dmt$^1$,AtnDap$^4$]DALDA into Caco-2 cells after incubation for as little as 15 min at 37° C. The uptake of dye was completely excluded from the nucleus, but the blue dye showed a streaky distribution within the cytoplasm. Mitochondria were labeled red with TMRM. The distribution of [Dmt$^1$,AtnDap$^4$]DALDA to mitochondria was demonstrated by the overlap of the [Dmt$^1$, AtnDap$^4$]DALDA distribution and the TMRM distribution.

Example 3

Figure 1B:
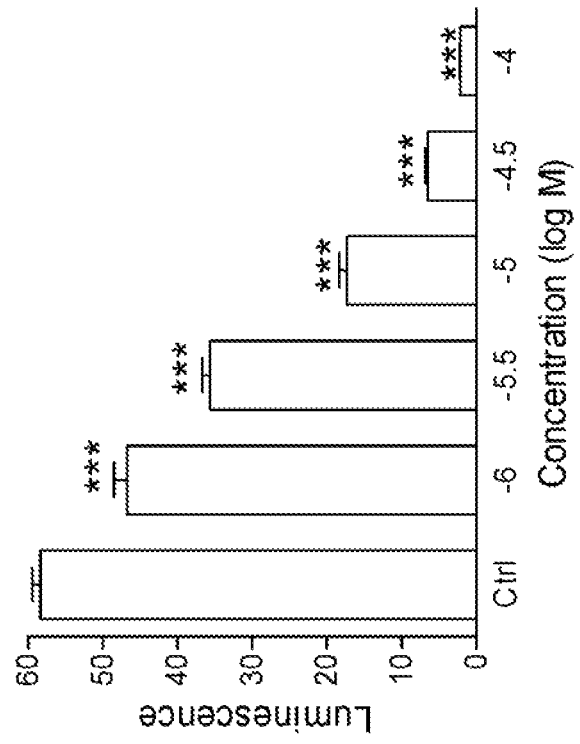

Scavenging of Hydrogen Peroxide by SS-02 and SS-05 (FIG. 1)

Effect of SS-02 and SS-05 (Dmt-D-Arg-Phe Orn-NH$_2$) on H$_2$O$_2$ as measured by luminol-induced chemiluminescence, 25 µM luminol and 0.7 IU horseradish peroxidase were added to the solution of H$_2$O$_2$ (4.4 nmol) and peptide, and chemiluminescence was monitored with a Chronolog Model 560 aggregometer (Havertown, Pa.) for 20 min at 37° C.

Results show that SS-02 and SS-05 dose-dependently inhibited the luminol response suggesting that these peptides can scavenge H$_2$O$_2$.

Example 4

Figure 2A:
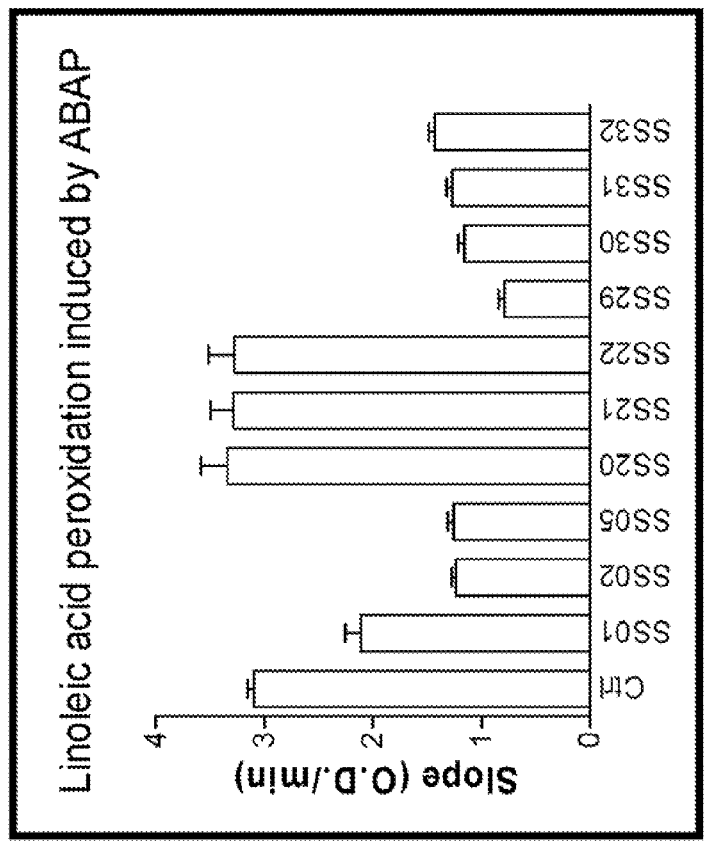
FIG. 2. (A) SS-02 dose-dependently inhibits linoleic acid peroxidation induced by ABAP and (B) SS-02 SS-05, SS-29, SS-30, SS-31, SS-32 and Dmt reduced the rate of linoleic acid peroxidation induced by ABAP.
Figure 2B:
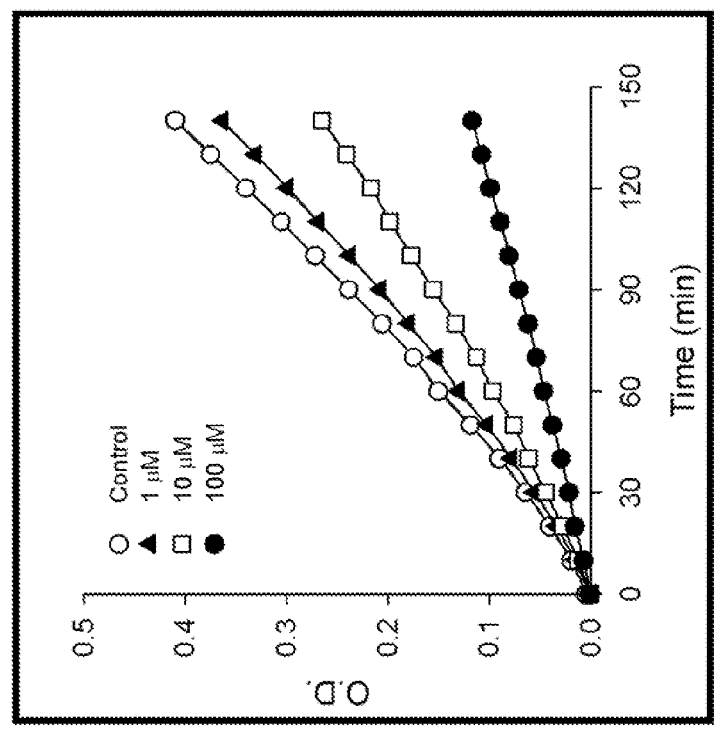

Inhibition of Lipid Peroxidation (FIG. 2)

Linoleic acid peroxidation was induced by a water-soluble initiator. ABAP (2,2'-azobis(2-amidinopropane)), and lipid peroxidation was detected by the formation of conjugated dienes, monitored spectrophotometrically at 236 nm (B. Longoni, W. A. Pryor, P. Marchiafava, *Biochem. Biophys. Res. Commun.* 233, 778-780 (1997)).

5 ml of 0.5 M ABAP and varying concentrations of SS-02 were incubated in 2.4 ml linoleic acid suspension until autoxidation rate became constant. Results show that SS-02 dose-dependently inhibited the peroxidation of linoleic acid.

Various peptides were added in concentration of 100 μM. The data are presented as the slope of diene formation. With the exception of SS-20 (Phe-D-Arg-Phe-Lys-NH$_2$), SS-21 (Cyclohexyl-D-Arg-Phe-Lys-NH$_2$) and SS-22 (Ala-D-Arg-Phe-Lys-NH$_2$), all other SS peptides reduced the rate of linoleic acid peroxidation. Note that SS-20, SS-21 and SS-22 do not contain either tyrosine or dimethyltyrosine residues. SS-01, which contains Tyr rather than Dmt is not as effective in preventing linoleic acid peroxidation. SS-29 is Dmt-D-Cit-Phe Lys-NH$_2$. SS-30 is Phe-D-Arg-Dmt-Lys-NH$_2$, SS-32 is Dmt-D-Arg-Phe-Ahp(2-aminoheptanoic acid)-NH$_2$.

Example 5

Figure 3B:
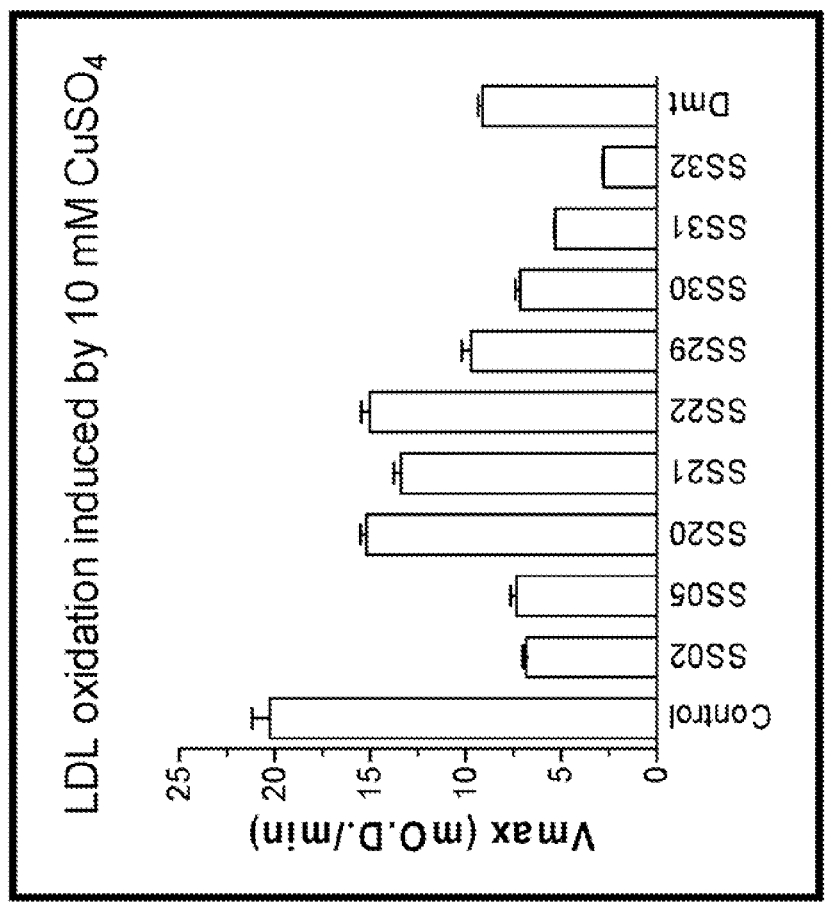
FIG. 3. (A) SS-02 dose-dependently inhibits LDL oxidation induced by 10 mM $CuSO_4$ and (B) SS-02, SS-05, SS-29, SS-30, SS-31, SS-32 and Dmt reduced rate of LDL oxidation.
Figure 3A:
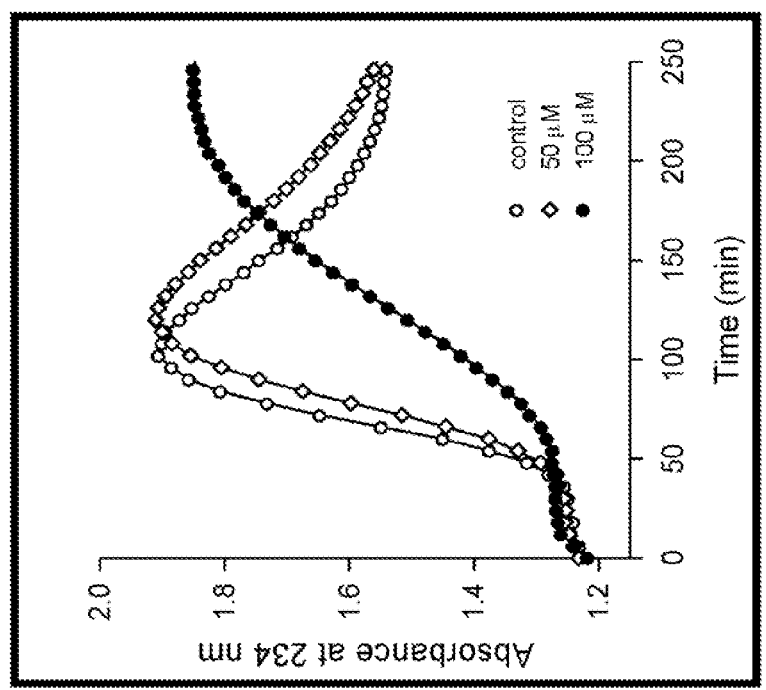

Inhibition of LDL Oxidation (FIG. 3)

Human LDL (low density lipoprotein) was prepared fresh from stored plasma. LDL oxidation was induced catalytically by the addition of 10 mM CuSO$_4$, and the formation of conjugated dienes was monitored at 24 nm for 5 h at 37° C. (B. Moosmann and C. Behl, *Mol Pharmacol.*, 61, 260-268 (2002)).

(A) Results show that SS-02 dose-dependently inhibited the rate of LDL oxidation.

(B) Various peptides were added in concentration of 100 μM. With the exception of SS-20 (Phe-D-Arg-Phe-Lys NH$_2$) SS-21. (Cyclohexyl-D-Arg-Phe-Lys-NH$_2$) and SS-22 (Ala-D-Arg-Phe-Lys-NH$_2$), all other SS peptides reduced the rate of linoleic acid peroxidation (reduced rate of formation of conjugated dienes). Note that SS-20, SS-21 and SS-22 do not contain either tyrosine or dimethyltyrosine residues. SS-29 is Dmt-D-Cit-Phe-Lys-NH$_2$, SS-30 is Phe-D-Arg-Dmt-Lys-NH$_2$, SS-32 is Dmt-D-Arg-Phe-Ahp(2-aminoheptanoic acid)-NH$_2$.

Example 6

Hydrogen Peroxide Production by Isolated Mouse Liver Mitochondria (FIG. 4)

Because mitochondria are a major source of ROS production, the effect of SS-02 on H$_2$O$_2$ formation in isolated mitochondria under basal conditions as well as after treatment with antimycin, a complex III inhibitor was examined. Livers were harvested from mice and homogenized in ice-cold buffer and centrifuged at 13800×g for 10 m. The pellet was washed once and then re-suspended in 0.3 ml of wash butter and placed on ice until use H$_2$O$_2$ was measured using luminol chemiluminescence as described previously (Y. Li, H. Zhu, M. A. Trush, *Biochim. Biophys. Acta* 1428, 1-12 (1999)). 0.1 mg mitochondrial protein was added to 0.5 ml potassium phosphate buffer (100 mM, pH 8.0) in the absence or presence of SS peptides (100 μM). 25 mM luminol and 0.7 IU horseradish peroxidase were added, and chemilumunescence was monitored with a Chronolog Model 560 aggregometer (Havertown, Pa.) for 20 min at 37° C. The amount of H$_2$O$_2$ produced was quantified as the area under the curve (AUC) over 20 min, and all data were normalized to AUC produced by mitochondria alone.

(A) The amount of H$_2$O$_2$ production was significantly reduced in the presence of 10 μM SS-02. Addition of antimycin (1 μM) significantly increased H$_2$O$_2$ production by isolated mitochondria, and the increase was completely blocked by 1.0 μM Dmt$^1$-DALDA (also referred to as dDALDA in the specification).

(B) The amount of H$_2$O$_2$ generated was significantly reduced by peptides SS-02, SS-29, SS-30 and SS-31. SS-21 and SS-22 had no effect on H$_2$O$_2$ production. Note that SS-21 and SS-22 do not contain a tyrosine or dimethyltryosine residue. The amino acid Dmt dimethyltyrosine) alone also inhibited H$_2$O$_2$ generated.

Example 7

Figure 5B:
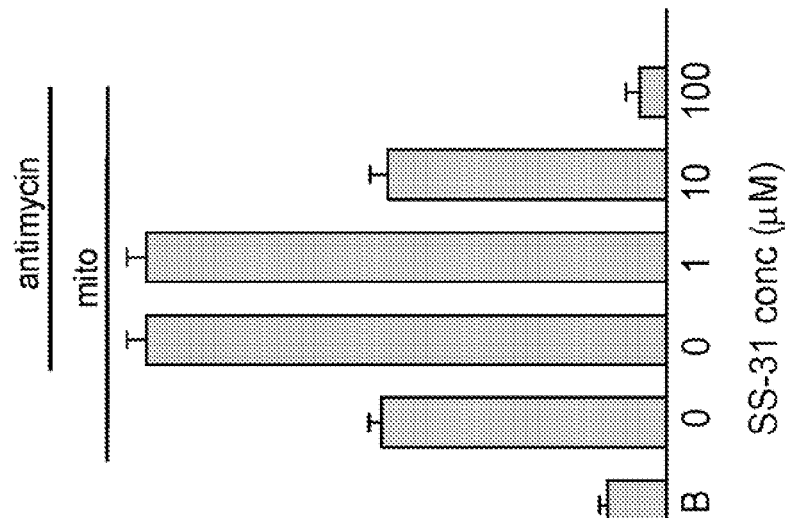
FIG. 5. (A) SS-31 inhibits spontaneous production of hydrogen hydroperoxide by isolated mitochondria and (B) SS-31 inhibits hydrogen peroxide production stimulated by antimycin.
Figure 5A:
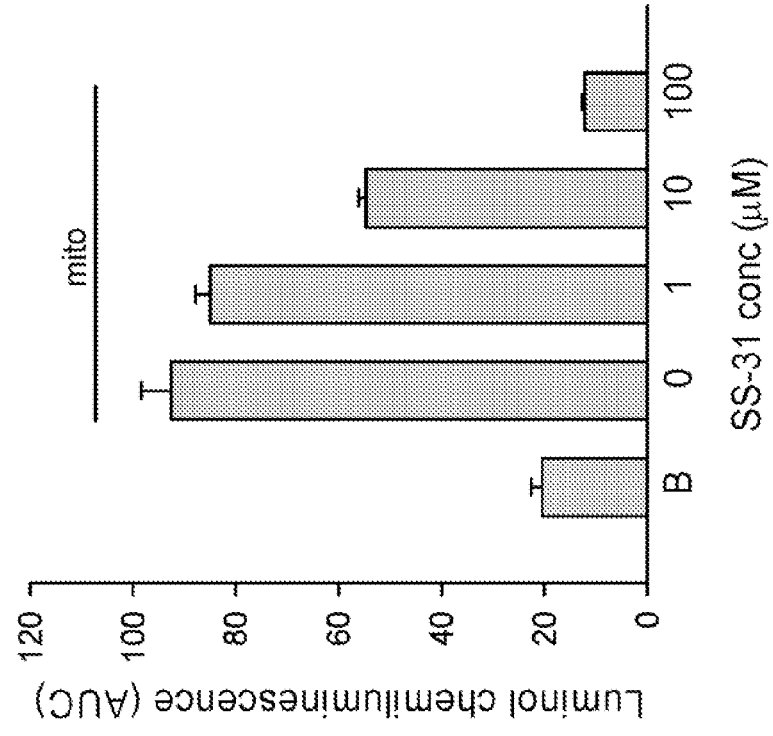

SS-31 inhibits H$_2$O$_2$ Generation by Isolated Mitochondria (FIG. 5)

H$_2$O$_2$ was measured using luminol chemiluminescence as described previously (Y, Li, H. Zhu, M. A. Trush, *Biochim. Biophys. Acta* 1428, 1-12 (1999)). 0.1 mg mitochondrial protein was added to 0.5 ml potassium phosphate buffer (100 mM, pH 8.0) in the absence or presence of SS-31. 25 mM luminol and 0.7 IU horseradish peroxidase were added, and chemilumunescence was monitored with a Chronolog Model 560 aggregometer (Havertown, Pa.) for 20 min at 37° C. The amount of H$_2$O$_2$ produced was quantified as the area under the curve (AUC) over 20 min, and all data were normalized to AUC produced by mitochondria alone.

(A) SS-31 dose-dependently reduced the spontaneous production of H$_2$O$_2$ by isolated mitochondria.

(B) SS-31 dose-dependently reduced the production of H$_2$O$_2$ induced by antimycin in isolated mitochondria.

Example 8

SS-02 and SS-31 Reduced Intracellular ROS and Increased Cell Survival (FIG. 6)

To show that the claimed peptides are effective when applied to whole cells, neuronal N$_2$A cells were plated in 96-well plates at a density of 1×10$^4$/well and allowed to grow for 2 days before treatment with tBHP (0.5 or 1 mM) for 40 min. Cells were washed twice and replaced with medium alone or medium containing varying concentrations of SS—O$_2$ or SS-31 for 4 hr. Intracellular ROS was measured by carboxy-H2DCFDA (Molecular Probes, Portland, Oreg.). Cell death was assessed by a cell proliferation assay (MTS assay, Promega, Madison, Wis.).

Incubation with tBHP resulted in dose-dependent increase in intracellular ROS (A) and decrease in cell viability, (B and C). Incubation of these cells with either SS-31 or SS-02 dose-dependently reduced intracellular ROS (A) and increased cell survival (B and C), with EC50 in the nM range.

Example 9

Figure 7A:
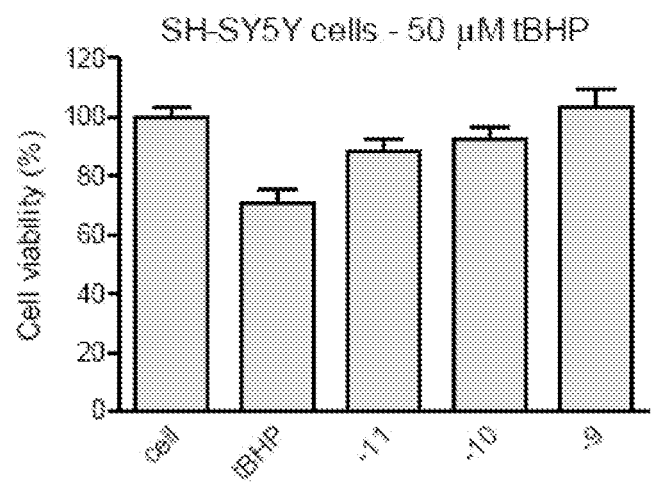
FIG. 7. SS-31 dose-dependently prevented loss of cell viability caused by low doses of t-BHP (0.05-0.1 mM) in neuronal (A) SH-SY5Y and (B) $N_2A$ cells.
Figure 7B:
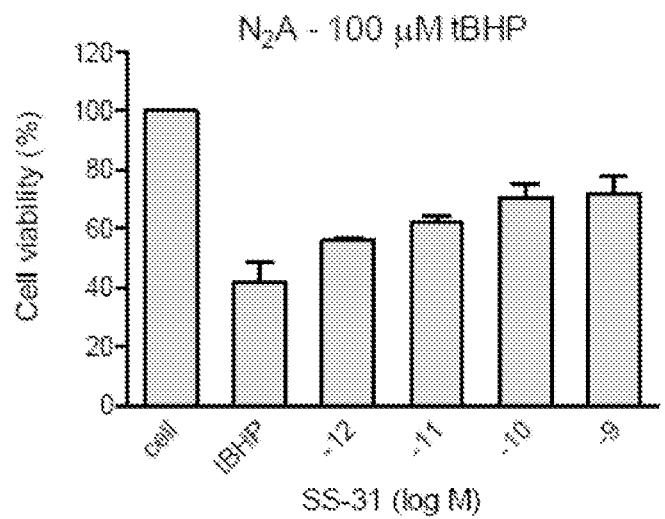

SS-31 Prevented Loss of Cell Viability (FIG. 7)

Neuronal N$_2$A and SH-SY5Y cells were plated in 96-well plate at a density of 1×10$^4$/well and allowed to grow for 2 days before treatment with t-butyl hydroperoxide (tBHP) (0.05-0.1 mM) with or without SS-31 (10$^{-12}$ M to 10$^{-9}$ M for 24 h. Cell death was assessed by a cell proliferation assay (MTS assay, Promega, Madison, Wis.).

Treatment of N$_2$A and SH-SY5Y cells with low doses of t-BHP (0.05-0.1 mM) for 24 h resulted in a decrease in cell viability. (A) 0.05 mM t-BHP induced 50% loss of cell viability in N$_2$A cells and 30% in SH-SY5Y cells. (B) 0.1 mM t-BHP resulted in a greater reduction in cell viability in SH-SY5Y cells. Concurrent treatment of cells with SS-31 resulted in a dose-dependent reduction of t-BHP-induced cytotoxicity. Complete protection against t-BHP was achieved by 1 nM SS-31.

Example 10

Figure 8:
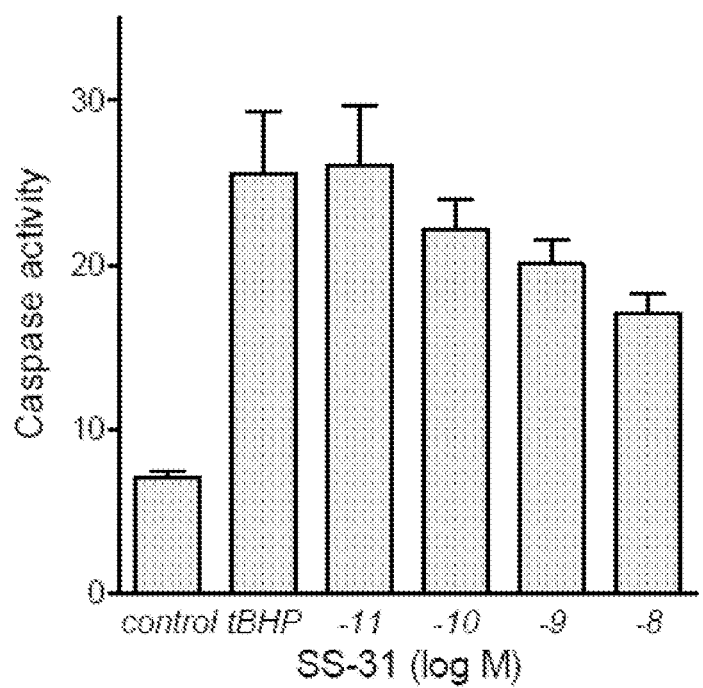
FIG. 8. SS-31 dose-dependently decreased the percent of cells showing increased caspase activity after treatment with a low dose of t-BHP for 12 h in $N_2A$ cells.

SS-31 Decreased Capase Activity (FIG. 8)

$N_2A$ cells were grown on 96-well plates, treated with t-BHP (0.05 mM) in the absence or presence of SS-31 ($10^{-11}$ M-$10^{-8}$ M) at 37° C. for 12-24 h. All treatments were carried out in quadriplicates. $N_2A$ cells were incubated with t-BHP (50 mM) with or without SS-31 at 37° C. for 12 h. Cells were gently lifted from the plates with a cell detachment solution (Accutase, Innovative Cell Technologies, Inc., San Diego, Calif.) and washed twice in PBS. Caspase activity was assayed using the FLICA kit (Immunochemistry Technologies LLC, Bloomington, Minn.) According to the manufacturer's recommendation, cells were resuspended (approx. $5 \times 10^6$ cells/ml) in PBS and labeled with pan-caspase inhibitor FAM-VAD-FMK for 1 h at 37° C. under 5% $CO_2$ and protected from the light. Cells were then rinsed to remove the unbound reagent and fixed. Fluorescence intensity in the cells was measured by a laser scanning cytometer (Beckman-Coulter XL, Beckman Coulter, Inc., Fullerton, Calif.) using the standard emission filters for green (FL1). For each run, 10,000 individual events were collected and stored in list-mode files for off-line analysis.

Caspase activation is the initiating trigger of the apoptotic cascade, and our results showed a significant increase in caspase activity after incubation of SH-SY5Y cells with 50 mM t-BHP for 12 h which was dose-dependently inhibited by increasing concentrations of SS-31.

Example 11

Figure 9:
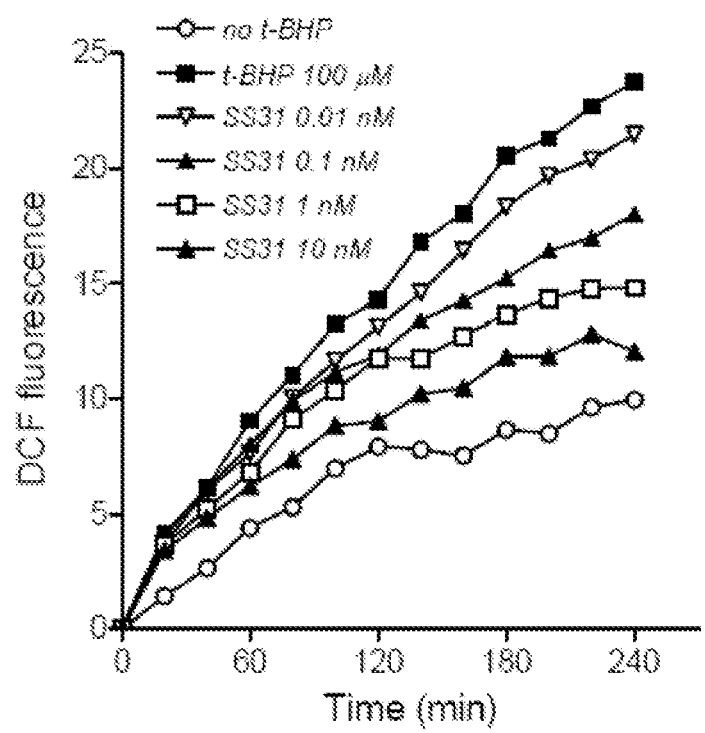
FIG. 9. SS-31 dose-dependently reduced the rate of ROS accumulation in $N_2A$ cells with 0.1 mM t-BHP over a 4 h period.

SS-31 Reduced Rate of ROS Accumulation (FIG. 9)

Intracellular ROS was evaluated using the fluorescent probe DCFH-DA (5-(and-6)-carboxy-2',7'-dichlorodihydrofluorescein diacetate). DCFH-DA enters cells passively and is then deacetylated to nonfluorescent DCFH. DCFH reacts with ROS to form DCF, the fluorescent product. $N_2A$ cells in 96 sell plates were washed with HBSS and loaded with 10 µM of DCFDA for 30 min. for 30 min. at 37° C. Cells were washed 3 times with BSS and exposed to 0.1 mM of t-BHP, alone or with SS-31. The oxidation of DCF was monitored in real time by a fluorescence microplate reader (Molecular Devices) using 485 nm for excitation and 530 nm for emission.

The rate of ROS accumulation in $N_2A$ cells treated with 0.1 mM t-BHP was dose-dependently inhibited by the addition of SS-31.

Example 12

Figure 10:
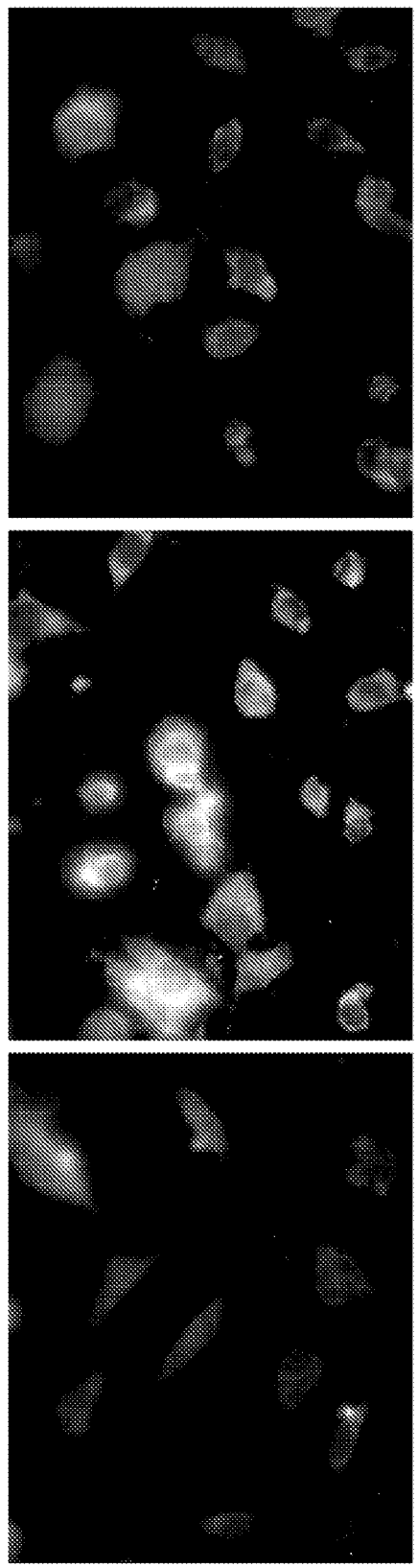
FIG. 10. SS-31 inhibited lipid peroxidation caused by exposure of $N_2A$ cells to 1 mM t-BHP for 1 h. (A) untreated cells; (B) cells treated with 1 mM t-BHP for 3 h; (C) cells treated with 1 mM t-BHP and 10 nM SS-31 for 3 h.

SS-31 Inhibited Lipid Peroxidation in Cells Exposed to Oxidative Damage (FIG. 10)

SS-31 inhibited lipid peroxidation in $N_2A$ cells treated with t-BHP. Lipid peroxidation was evaluated by measuring FINE Michael adducts. 4-HNE is one of the major aldehydic products of the peroxidation of membrane polyunsaturated fatty acids. $N_2A$ cells were seeded on glass bottom dish 1 day before t-BHP treatment (1 mM, 3 h, 37° C., 5% $CO_2$) in the presence of absence of SS-31 ($10^{-8}$ to $10^{-10}$ M). Cells were then washed twice with PBS and fixed 30 min with 4% paraformaldehyde in PBS at RT and then washed 3 times with PBS. Cells were then permeabilized, treated with rabbit-anti-HNE antibody followed by the secondary antibody (goat anti-rabbit IgG conjugated to biotin). Cells were mounted in Vectashield and imaged using a Zeiss fluorescence microscope using an excitation wavelength of 460±20 nm and a longpass filter of 505 nm for emission.

(A) Untreated cells (B) cells treated with 1 mM t-BHP for 3 h; (C) cells treated with 1 mM t-BHP and 10 nM SS-31 for 3 h.

Example 13

SS-02 Inhibits Loss of Mitochondrial Potential in Cells Exposed to Hydrogen Peroxide Caco-2 cells were treated with tBHP (1 mM) in the absence or presence of SS-02 (0.1 µM) for 4 h, and then incubated with TMRM and examined under LSCM. In control cells, the mitochondria are clearly visualized as fine streaks throughout the cytoplasm. In cells treated with tBHP, the TMRM fluorescence is much reduced, suggesting generalized depolarization. In contrast, concurrent treatment with SS-02 protected against mitochondrial depolarization caused by tBHP.

Example 14

Figure 11:
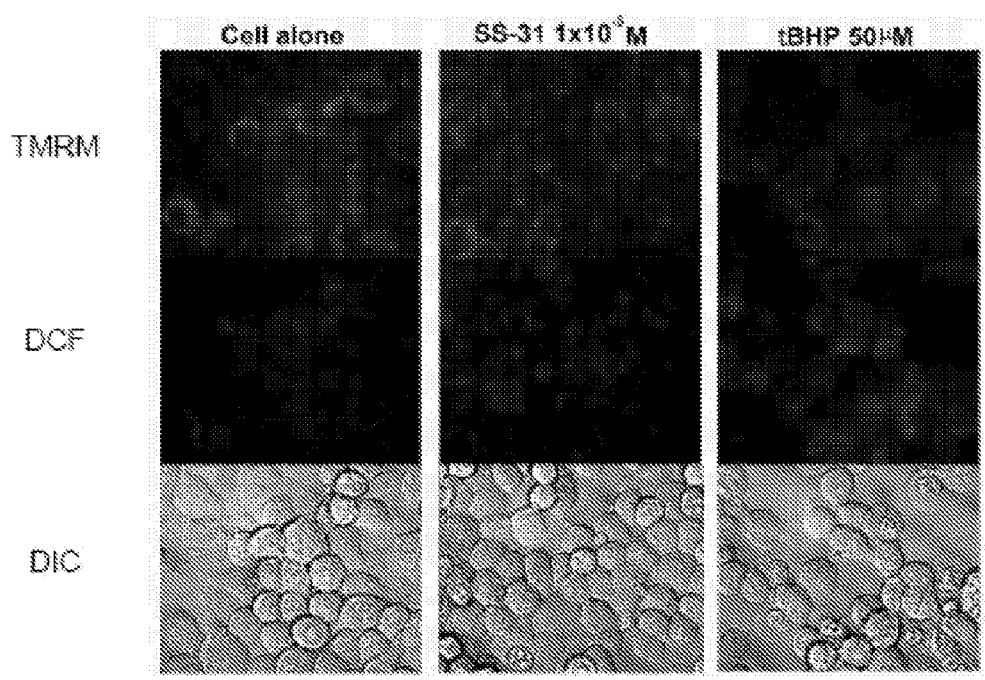
FIG. 11. SS-31 prevented mitochondrial depolarization and ROS accumulation in $N_2A$ cells exposed to t-BHP.

SS-31 Prevents Loss of Mitochondrial Potential and Increased ROS Accumulation in $N_2A$ Cells Caused by Exposure to t-BHP (FIG. 11)

$N_2A$ cells in glass bottom dish were treated with 0.1 mM t-BHP, alone or with 1 nM SS-31, for 6 h. Cells were then loaded with 10 µm of dichlorofluorescin (ex/em=485/530) for 30 min at 37° C., 5% $CO_2$. Then cells were subjected 3 times wash with HBSS and stained with 20 nM of Mitotracker TMRM (ex/em=550/575 nm) for 15 min at 37° C. and examined by confocal laser scanning microscopy.

Treatment of NA cells with t-BHP resulted in loss of TMRM fluorescence indicating mitochondrial depolarization. There was also a concomitant increase in DCF fluorescence indicating increase in intracellular ROS. Concurrent treatment with 1 nM SS-31 prevented mitochondrial depolarization and reduced ROS accumulation.

Example 15

Figure 12D:
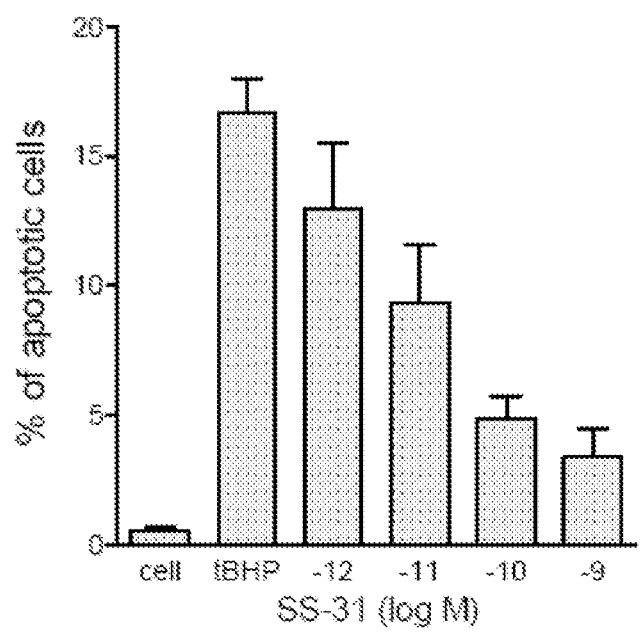
FIG. 12. SS-31 prevents apoptosis induced by a low dose of t-BHP. Apoptosis was evaluated by confocal microscopy with the fluorescent probe Hoechst 33342. (A1) a representative field of cells not treated with t-BHP. (A2) Fluorescent image showing a few cells with dense, fragmented chromatin indicative of apoptotic nuclei. (B1) A representative field of cells treated with 0.025 mM t-BHP for 24 h. (B2) Fluorescent image showing an increased number of cells with apoptotic nuclei. (C1) A representative field of cells treated with 0.025 mM t-BHP and 1 nM SS-31 for 24 h. (C2) Fluorescent image showing a reduced number of cells with apoptotic nuclei. (D) SS-31 dose-dependently reduced the percent of apoptotic cells caused by 24 h treatment with a low dose of T-BHP (0.05 mM).

SS-31 Prevents Apoptosis Caused by Oxidative Stress (FIG. 12)

SH-SY5Y cells were grown on 96-well plates, treated with t-BHP (0.025 mM) in the absence or presence of SS-31 ($10^{-12}$ M-$10^{-9}$ M) at 37° C. for 24 h. All treatments were carried out in quadriplicates. Cells were then stained with 2 mg/ml Hoechst 33342 for 20 min, fixed with 4% paraformaldehyde, and imaged using a Zeiss fluorescent microscope (Axiovert 200M) equipped with the Zeiss Acroplan x20 objective. Nuclear morphology was evaluated using an excitation wavelength of 350±10 nm and a longpass filter of 400 nm for emission. All images were processed and analyzed using the MetaMorph software (Universal Imaging Corp., West Chester, Pa.). Uniformly stained nuclei were scored as healthy, viable neurons, while condensed or fragmented nuclei were scored as apoptotic.

SS-31 prevents apoptosis induced by a low dose of t-BHP. Apoptosis was evaluated by confocal microscopy with the fluorescent probe Hoechst 33342 (A1) a representative field of cells not treated with t-BHP. (A2) Fluorescent image showing a few cells with dense, fragmented chromatin indicative of apoptotic nuclei. (A3) A representative field of cells treated with 0.025 mM t-BHP for 24 h. (A4) Fluorescent image showing an increased number of cells with apoptotic nuclei. (A5) A representative field of cells treated with 0.025 mM t-BHP and 1 nM SS-31 for 24 h. (A6) Fluorescent image showing a reduced number of cells with apoptotic nuclei.

(B) SS-31 dose-dependently reduced the percent of apoptotic cells caused by 24 h treatment with a low dose of t-BHP (0.05 mM).

Example 16

Figure 13A:
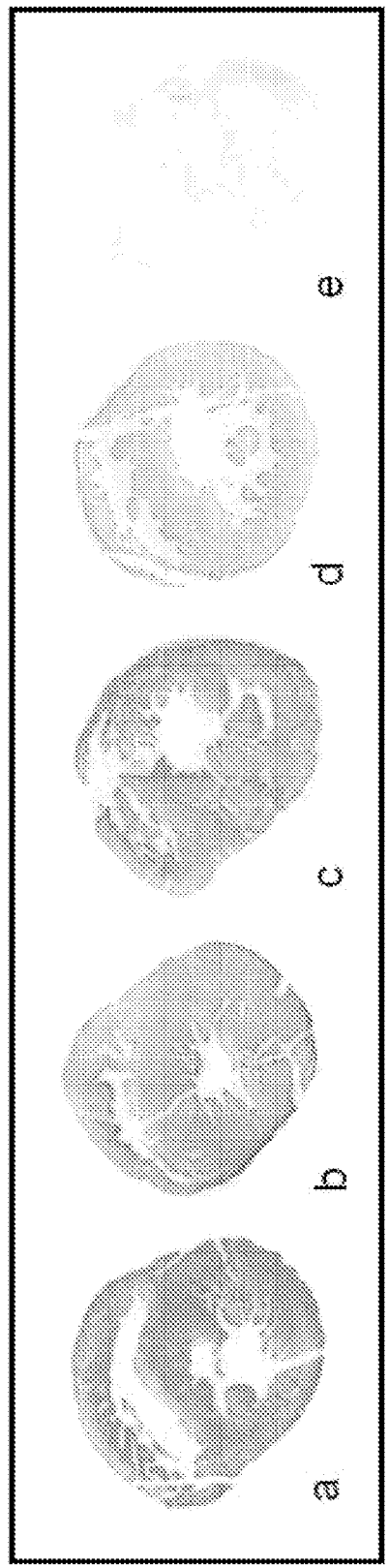
FIG. 13A. SS-02 and SS-31 reduced lipid peroxidation in isolated guinea pig hearts subjected to warm reperfusion after a brief period of ischemia. Immunohistochemical analysis of 4-hydroxy-2-nonenol (HNE)-modified proteins in paraffin sections from guinea pig hearts aerobically perfused 30 min with (a) buffer; (b) 100 nM SS-02; (c) 100 nM SS-20 and (d) 1 nM SS-31, then subjected to 30 min ischemia and reperfused for 90 min with corresponding peptides. Tissue slices were incubated with anti-HNE antibody. (e) Background control: staining without primary antibody.
Figure 13B:
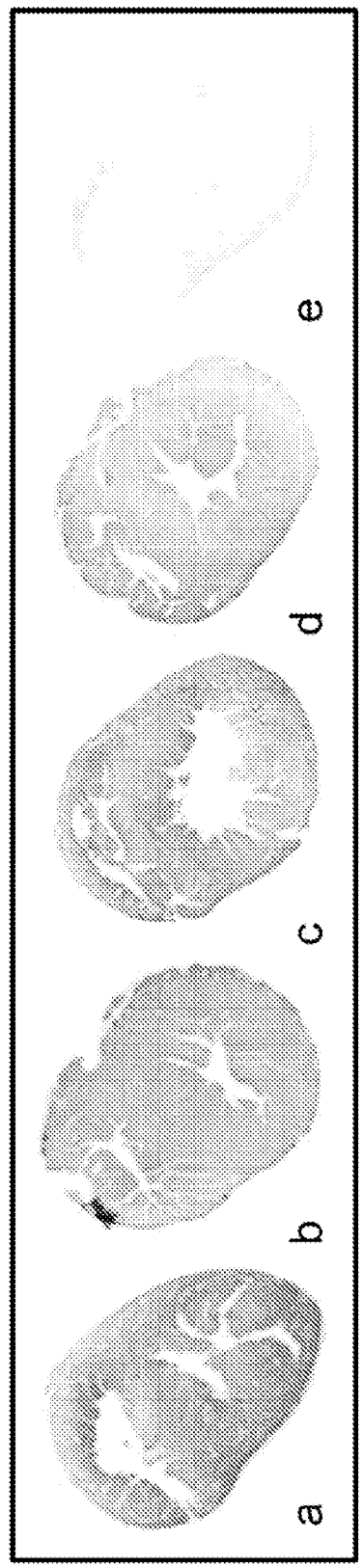
FIG. 13B. SS-02 and SS-31 reduced lipid peroxidation in isolated guinea pig hearts subjected to warm reperfusion after a brief period of ischemia. Immunohistochemical analysis of 4-hydroxynonenol (HNE)-modified proteins in paraffin sections from guinea pig hearts aerobically perfused 30 min with buffer, then subjected to 30 min ischemia and reperfused with (a) buffer; (b) 100 nM SS-02; (c) 100 nM SS-20 and (d) 1 nM SS-31 for 90 min. Tissue slices were incubated with anti-HNE antibody. (e) Background control: staining without primary antibody.

SS-31 Prevents Lipid Peroxidation in Hearts Subjected to Brief Intervals of Ischemia-Reperfusion. (FIG. 13)

Isolated guinea pig hearts were perfused in a retrograde manner in a Langendorff apparatus and subjected to various intervals of ischemia-reperfusion. Hearts were then fixed immediately and embedded in paraffin. Immunohistochemical analysis of 4-hydroxy-2-nonenol (HNE)-modified proteins in the paraffin sections was carried out using an anti-HNE antibody.

(A) Immunohistochemical analysis of 4-hydroxy-2-nonenol (HNE)-modified proteins in paraffin sections from guinea pig hearts aerobically perfused 30 min with (a) buffer; (b) 100 nM SS-02; (c) 100 nM SS-20 and (d) 1 nM SS-31, then subjected to 30 min ischemia and reperfused for 90 min with same peptides. Tissue slices were incubated with anti-HNE antibody. (e) Background control: staining without primary antibody.

(B) Immunohistochemical analysis of HNE-modified proteins in paraffin sections from guinea pig hearts aerobically perfused 30 min with buffer; then subjected to 30 min ischemia and reperfused with (a) buffer; (b) 100 nM SS-02; (c) 100 nM SS-20 and (d) 1 nM SS-31 for 90 min with same peptides. Tissue slices were incubated with anti-HNE antibody. (e) Background control staining without primary antibody.

Example 17

Figure 14A:
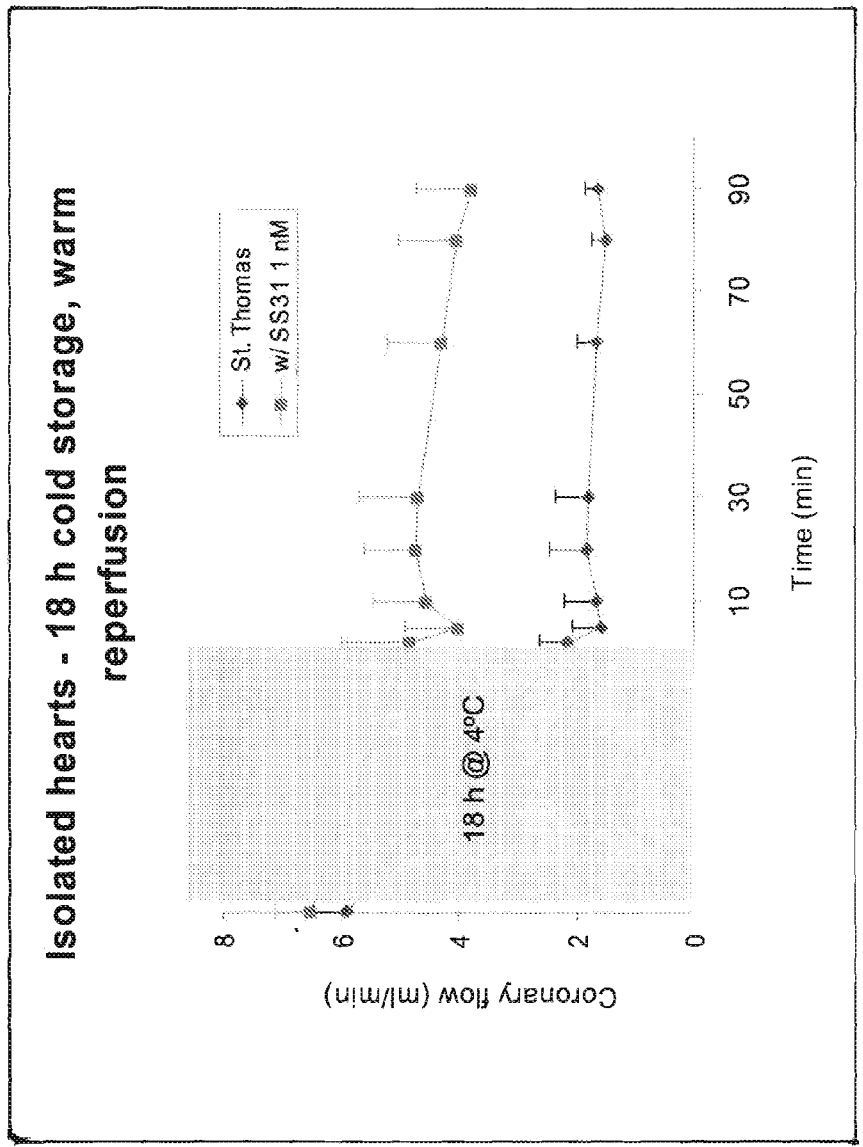
FIG. 14A. SS-31 significantly improved coronary flow in isolated guinea pig hearts subjected to warm reperfusion after prolonged (18 h) cold ischemia. The shaded area represents 18 h of ischemia at 4° C.
Figure 14B:
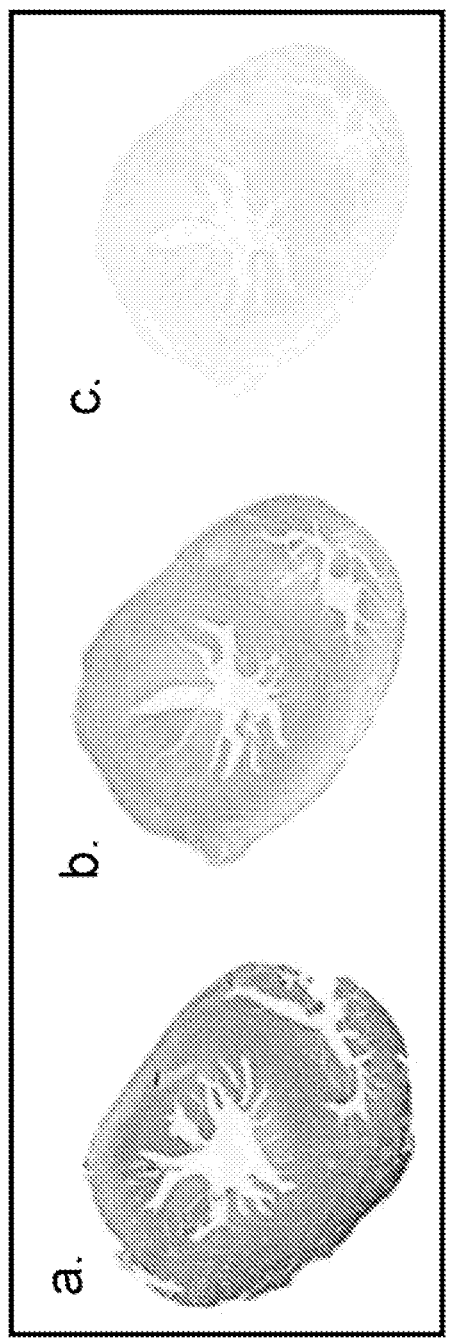
FIG. 14B. Guinea pig hearts perfused with a cardioplegic solution (St. Thomas solution) without (a) or with (b) 1 nM SS-31 for 3 min and then subjected to 18 h of cold ischemia (4° C.), (c) background staining with primary antibody. The hearts were then reperfused with buffer at 34° C. for 90 min.
Figure 14C:
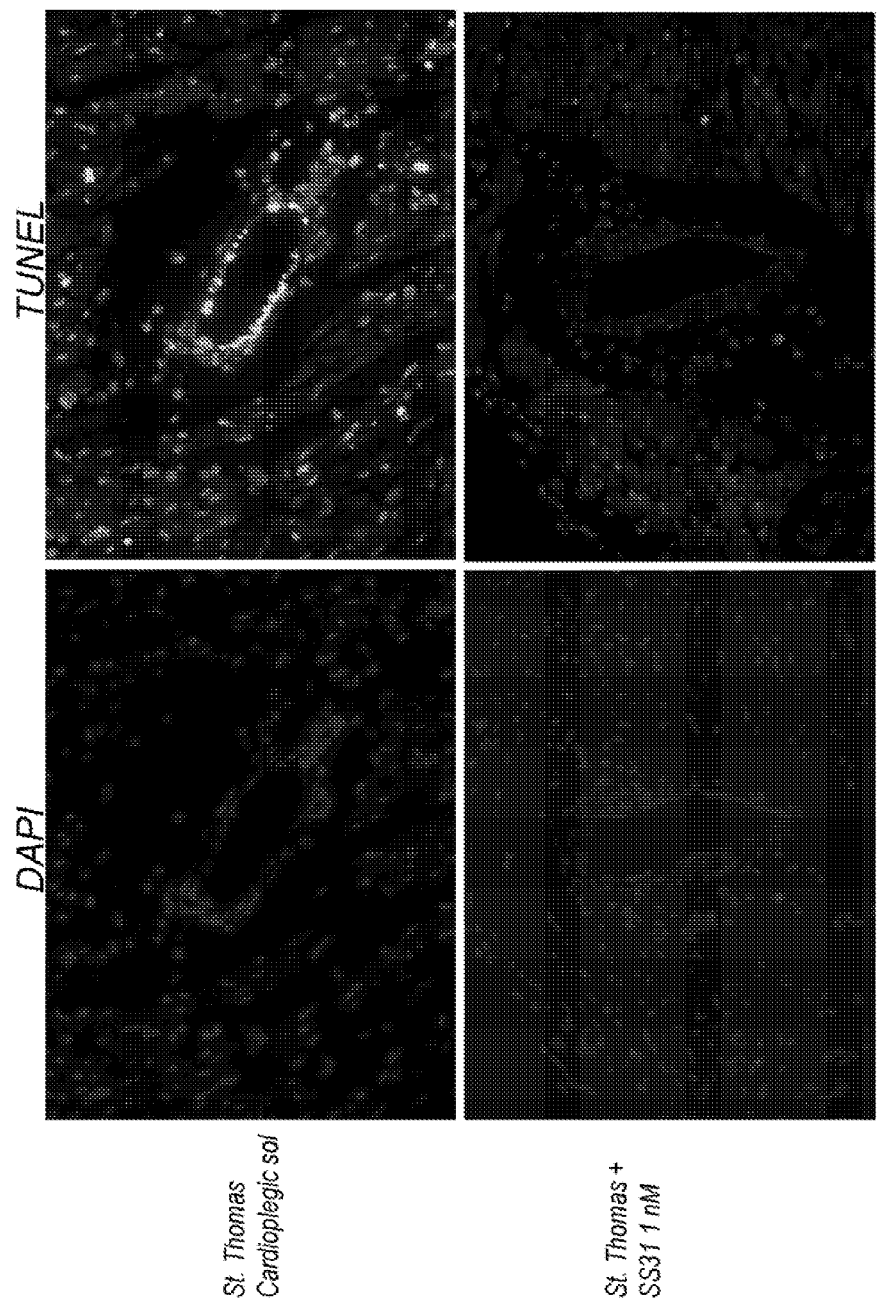
FIG. 14C. SS-31 prevents apoptosis in endothelial cells and myocytes in isolated guinea pig hearts subjected to warm reperfusion after prolonged (18 h) cold ischemia. Guinea pig hearts perfused with a cardioplegic solution (St. Thomas solution) without or with nM SS-31 for 3 min and then subjected to 18 h of cold ischemia (4° C.). The hearts were then reperused with buffer at 34° C. for 90 min. Apoptosis was assessed by the TUNEL stain (green) and nuclei are visualized by DAPI (blue).

SS-31 Increases Coronary Flow and Reduces Lipid Peroxidation and Apoptosis in Hearts Subjected to Prolonged Cold Ischemia Followed by Warm Reperfusion (FIG. 14)

Isolated guinea pig hearts were perfused in a retrograde manner in a Langendorff apparatus with a cardioplegic solution (St. Thomas solution) without or with SS-31 (1 nM) for 3 min. and then clamped and stored at 4° C. for 18 h. Subsequently, the hearts were remounted in the Langendorff apparatus and reperfused with Krebs-Henseleit solution at 34° C. for 90 min. Hearts were then rapidly fixed and paraffin-embedded.

(A) SS-31 significantly improved coronary flow in hearts after 18 h cold ischemic storage. The shaded area represents 18 h of cold ischemia.

(B) Immunohistochemical analysis of HNE-modified proteins in paraffin sections from guinea pig hearts stored without (a) or with (b) SS-31 (1 nM). (c) Background staining without primary antibody.

(C) SS-31 prevents apoptosis in endothelial cells and myocytes in isolated guinea pig hearts subjected to warm reperfusion after prolonged (18 h) cold ischemia. Apoptosis was assessed by the TUNEL stain (green) and nuclei are visualized by DAPI (blue).

Example 18

Figure 15A:
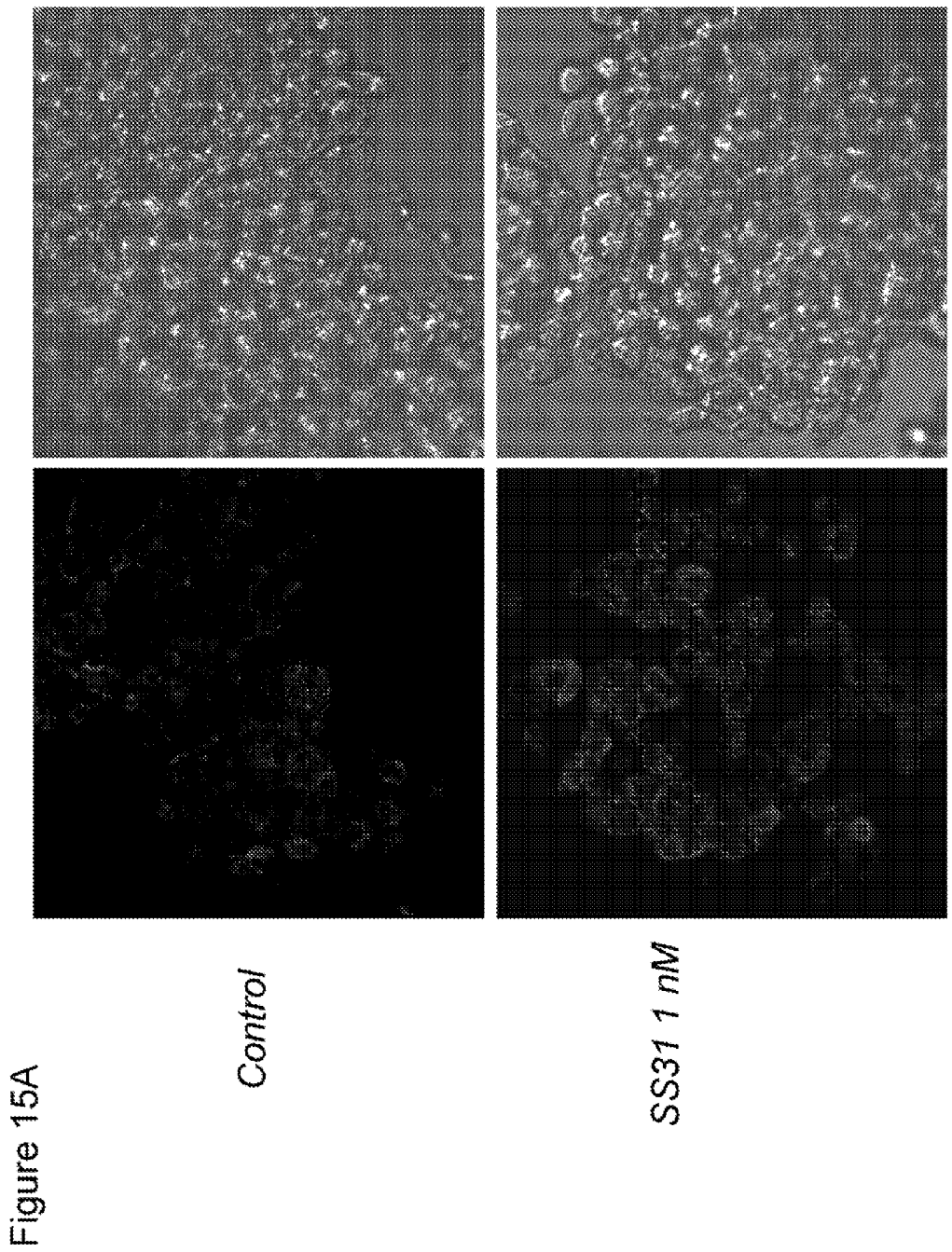
FIG. 15A. SS-31 improves survival of islet cells isolated from mouse pancreas as measured by mitochondrial potential. SS-31 (nM) was added to all isolation buffers used throughout the isolation procedure. Mitochondrial potential was measured using TMRM (red) with confocal microscopy.
Figure 15B:
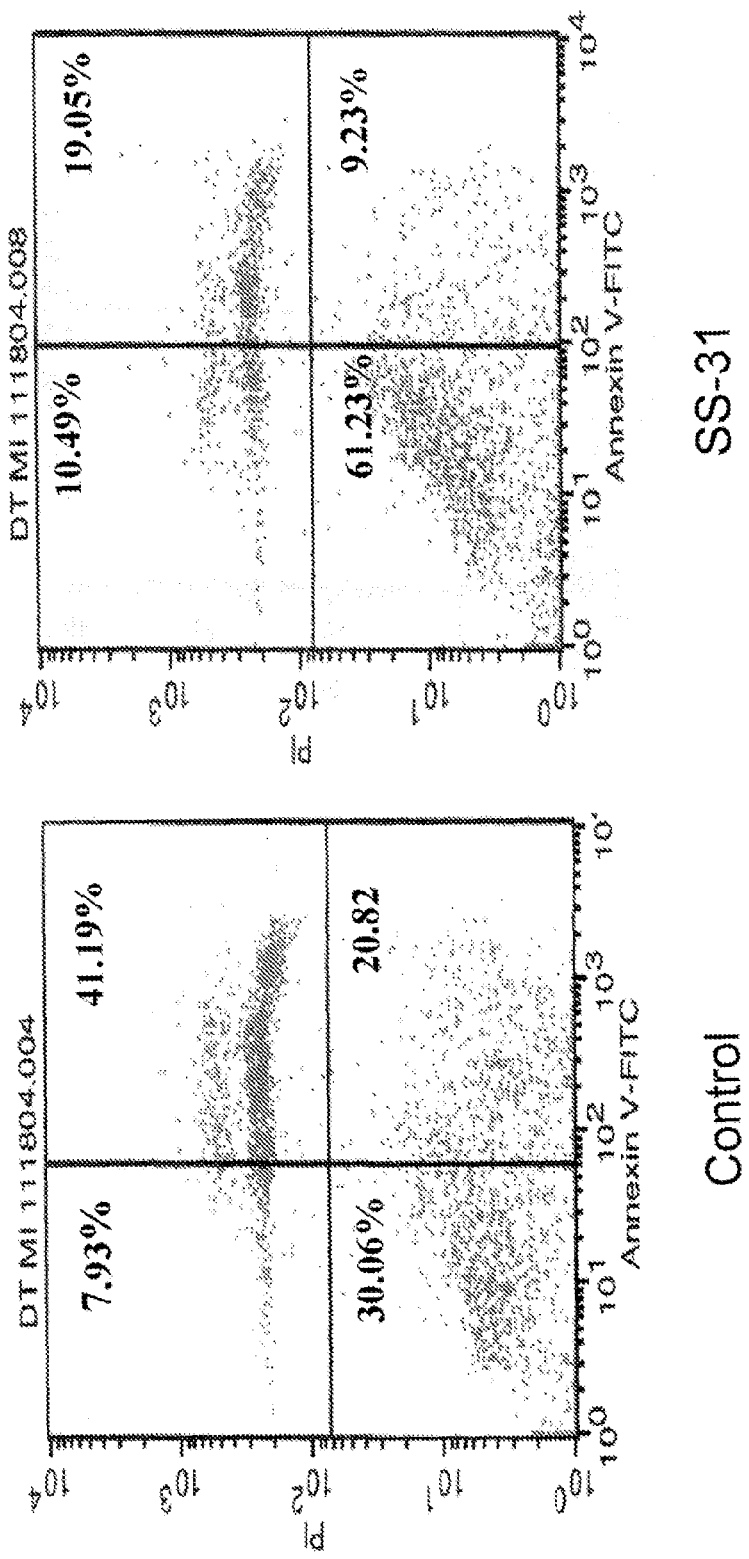
FIG. 15B. SS-31 reduces apoptosis and increases viability in islet cells isolated from mouse pancreas as measured by flow cytometry. SS-31 (1 nM) was added to all isolation buffers used throughout the isolation procedure. Apoptosis was ascertained using annexin V and necrosis by propidium iodide (PI).

SS-31 Improves Survival of Islet Cells Isolated from Mouse Pancreas (FIG. 15)

(A) SS-31 improves mitochondrial potential in islet cells isolated from mouse pancreas. Pancreas was harvested from mice and islet cells were prepared according standard procedures. In some studies, SS-31 (1 nM) was added to all isolation buffers used throughout the isolation procedure. Mitochondrial potential was measured using TMRM (red) and visualized by confocal microscopy.

(B) SS-31 reduces apoptosis and increases viability in islet cells isolated from mouse pancreas. Pancreas was harvested from mice and islet cells were prepared according standard procedures. In some studies, SS-31 (1 nM) was added to all isolation buffers used throughout the isolation procedure. Apoptosis was ascertained by flow cytometry using annexin V and necrosis by propidium iodide.

Example 19

Figure 16:
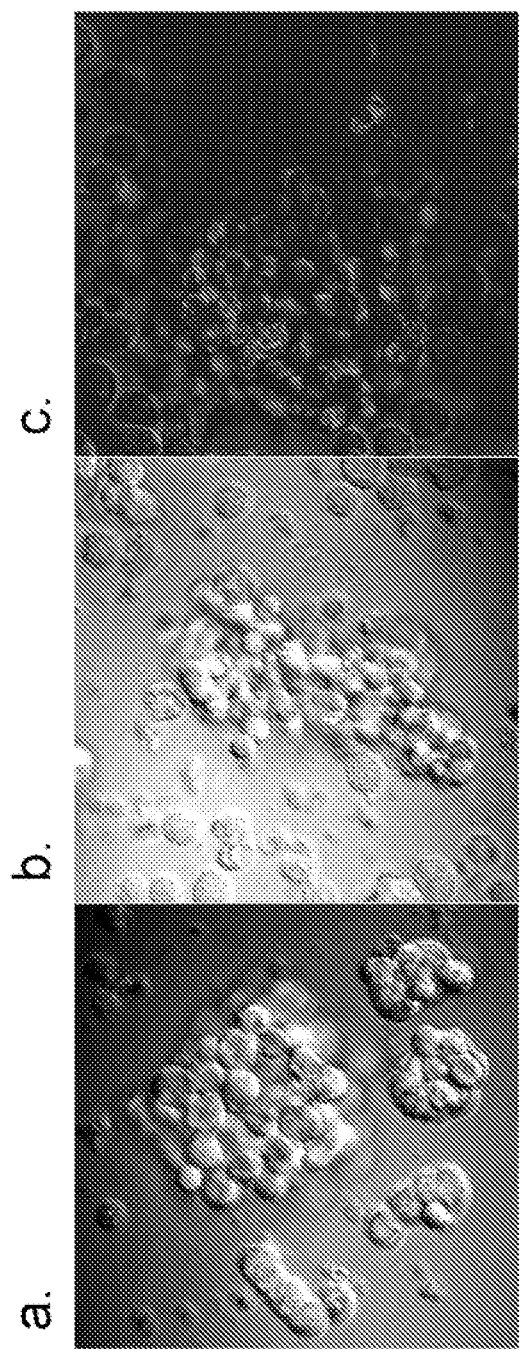
FIG. 16. SS-31 reduces oxidative damage in pancreatic islet cells caused by t-butylhydroperoxide (tBHP). Mouse pancreatic islet cells were untreated (a), or treated with 25 μM tBHP without (b) or with 1 nM SS-31 (c). Mitochondrial potential was measured by TMRM (red) and reactive oxygen species were measured by DCF (green) using confocal microscopy.

SS-31 Protects Against Oxidative Damage in Pancreatic Islet Cells (FIG. 16)

Mouse pancreatic islet cells were untreated (a), or treated with 25 µM tBHP without (b) or with 1 nM SS-31 (c). Mitochondrial potential was measured by TMRM (red) and reactive oxygen species were measured by DCF (green) using confocal microscopy.

Example 20

Figure 17A:
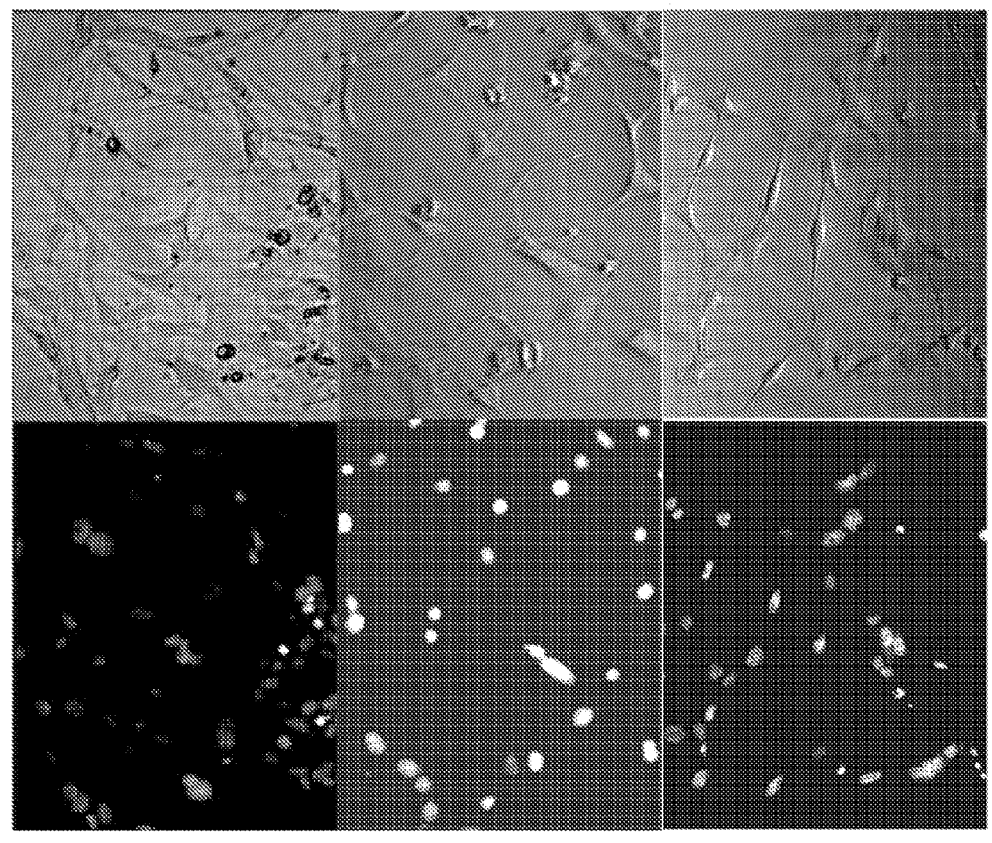
FIG. 17A. SS-31 protects dopamine cells against MPP* toxicity. SN-4741 cells were treated with buffer, 50 μM MPP* or 50 μM MPP* and 1 nM SS-31, for 48 h, and the incidence of apoptosis was determined by fluorescent microscopy with Hoechst 33342. The number of condensed fragmented nuclei was significantly increased by MPP* treatment. Concurrent treatment with SS-31 reduced the number of apoptotic cells.
Figure 17B:
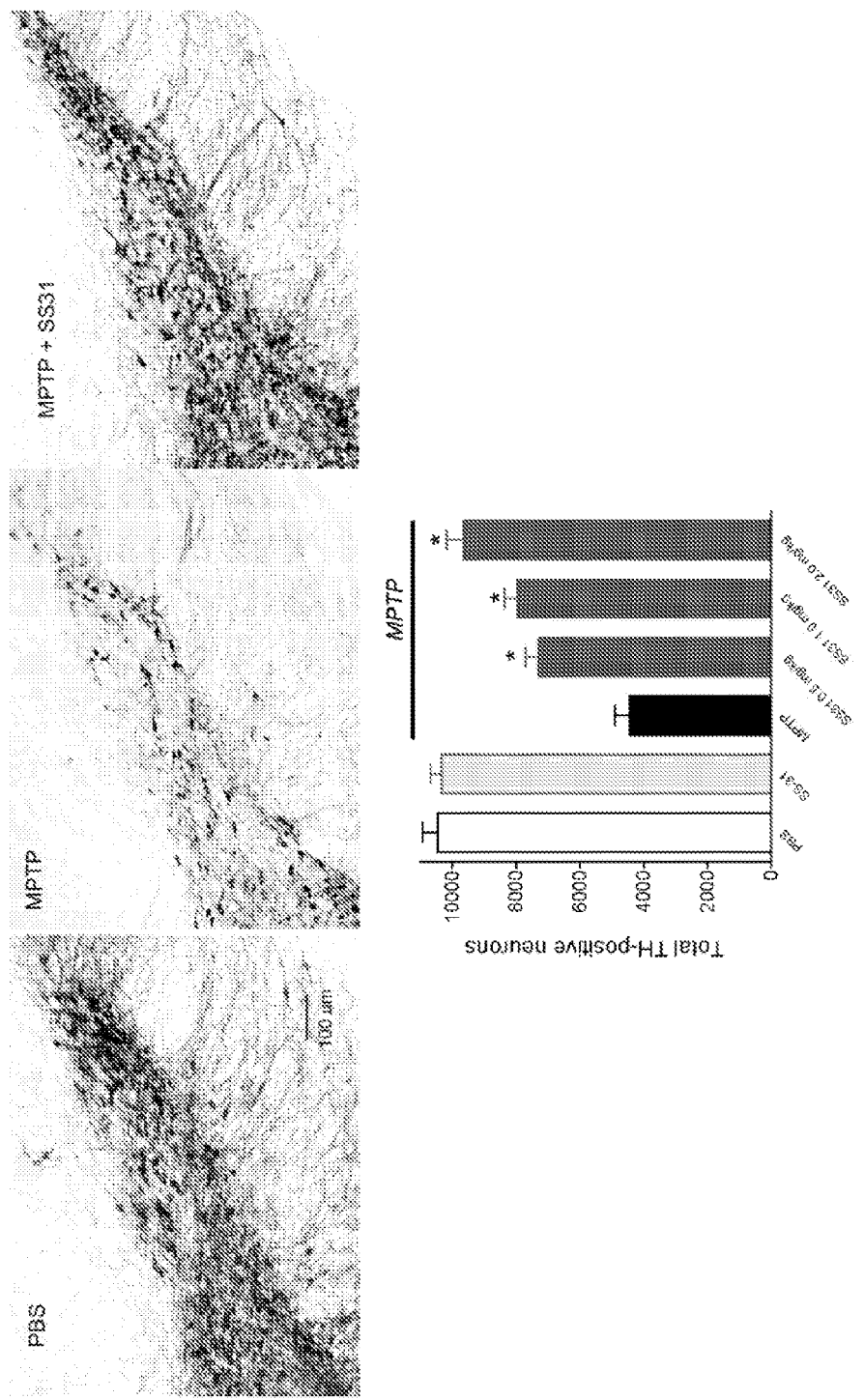
FIG. 17B. SS-31 dose-dependently prevented loss of dopamine neurons in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and striatal brain reactions were immunostained for tyrosine hydroxylase activity (shown in black).
Figure 17C:
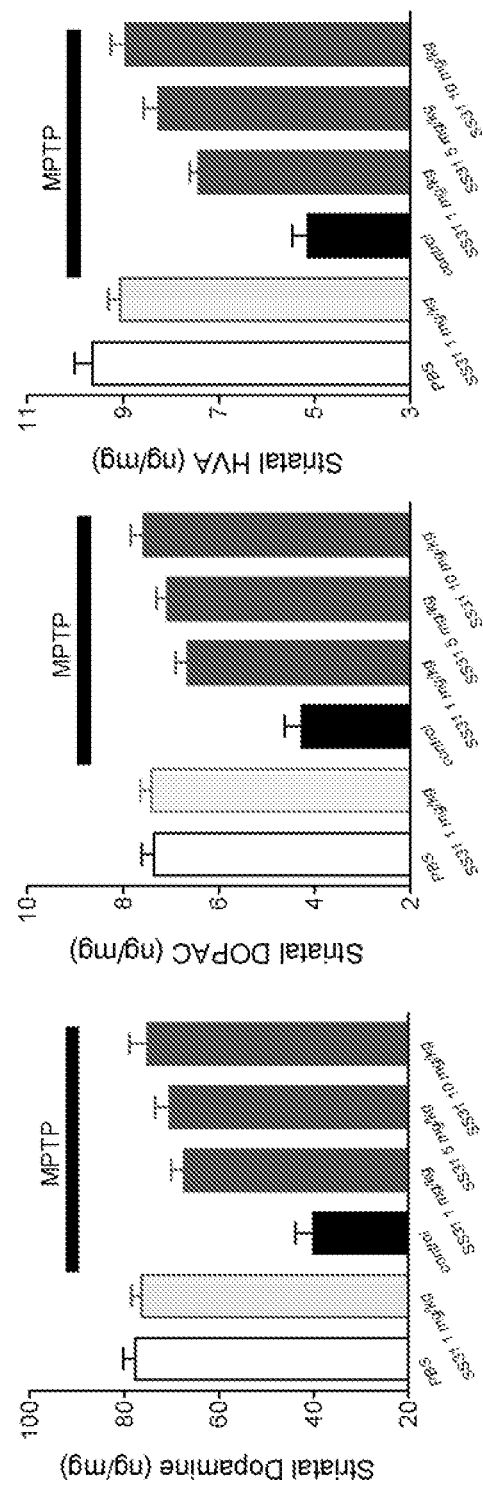
FIG. 17C. SS-31 dose-dependently increased striatal dopamine, DOPAC (3,4-dihydroxyphenylacetic acid) and HVA (homovanillic acid) levels in mice treated with MPTP. Three doses of MPTP (10 mg/kg) was given to mice (n=12) 2 h apart. SS-31 was administered 30 min before each MPTP injection, and at 1 h and 12 h after the last injection. Animals were sacrificed one week later and dopamine, DOPAC and HVA levels were quantified by high pressure liquid chromatography.

SS-31 Protects Against Parkinson's Disease (FIG. 17)

MPTP is a neurotoxin that selectively destroys striatal dopamine neurons and can be used as an animal model of Parkinson's Disease. MPP$^+$, a metabolite of MPTP, targets mitochondria, inhibits complex I of the electron transport chain and increases ROS production. MPP$^+$ is used in cell culture studied because cells are unable to metabolize MPTP to the active metabolite. MPTP is used for animal studies.

(A) SS-31 protects dopamine cells against MPP$^+$ toxicity. SN-4741 cells were treated with buffer, 50 µM MPP$^+$ or 50 µM MPP$^+$ and 1 nM SS-31, for 48 h, and the incidence of apoptosis was determined by fluorescent microscopy with Hoechst 33342. The number of condensed fragmented nuclei was significantly increased by MPP+ treatment. Concurrent treatment with SS-31 reduced the number of apoptotic cells.

(B) SS-31 dose-dependently prevented loss of dopamine neurons in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and striatal brain regions were immunostained for tyrosine hydroxylase activity.

(C) SS-31 dose-dependently increased striatal dopamine DOPAC (3,4-dihydroxyphenylacetic acid) and HVA (homovanillic acid) levels in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and dopamine, DOPAC and HVA levels were quantified by high pressure liquid chromatography.

Example 21

Figure 18:
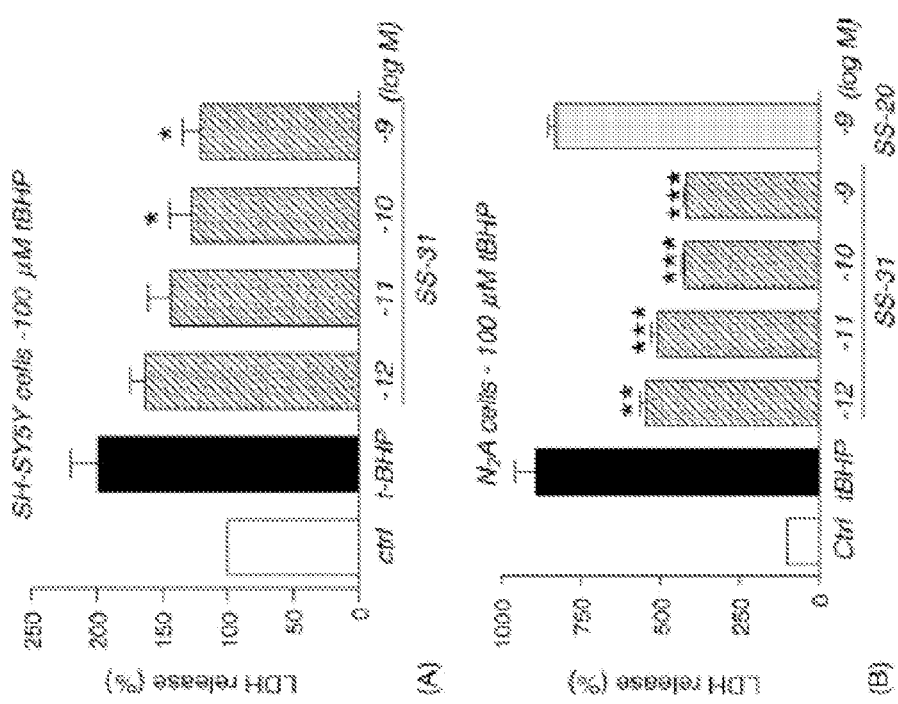
FIG. 18. SS-31 reduced tBHP-induced LDH release in SH-SY5Y (A) and $N_2A$ (B) cells. Cells were treated with 100 μM tBHP alone, or with SS-31, for 24 h. *$P<0.05$, $P<0.01$, *$P<0.001$, compared to tBHP alone.

SS-31 Protected SH-SY5Y and N₂A Cells Against tBHP Induced Cytotoxicity (FIG. 18)

The loss of cell viability induced by 100 μM tBHP was accompanied by a significant increase in LDH release in SH-SY5Y (FIG. 18A) and N₂A cell (FIG. 18B). (Concurrent treatment of cells with SS-31 resulted in dose-dependent decrease in LDH release in both SH-SY5Y ($P<0.01$) and N₂A cells ($P<0.0001$). LDH release was reduced significantly by 0.1 and 1 nM of SS-31 in both cell lines ($P<0.05$). SS-20, the control non-scavenging peptide, did not protect against tBHP-induced cytotoxicity in N2A cells (FIG. 18B).

Example 22

Figure 19:
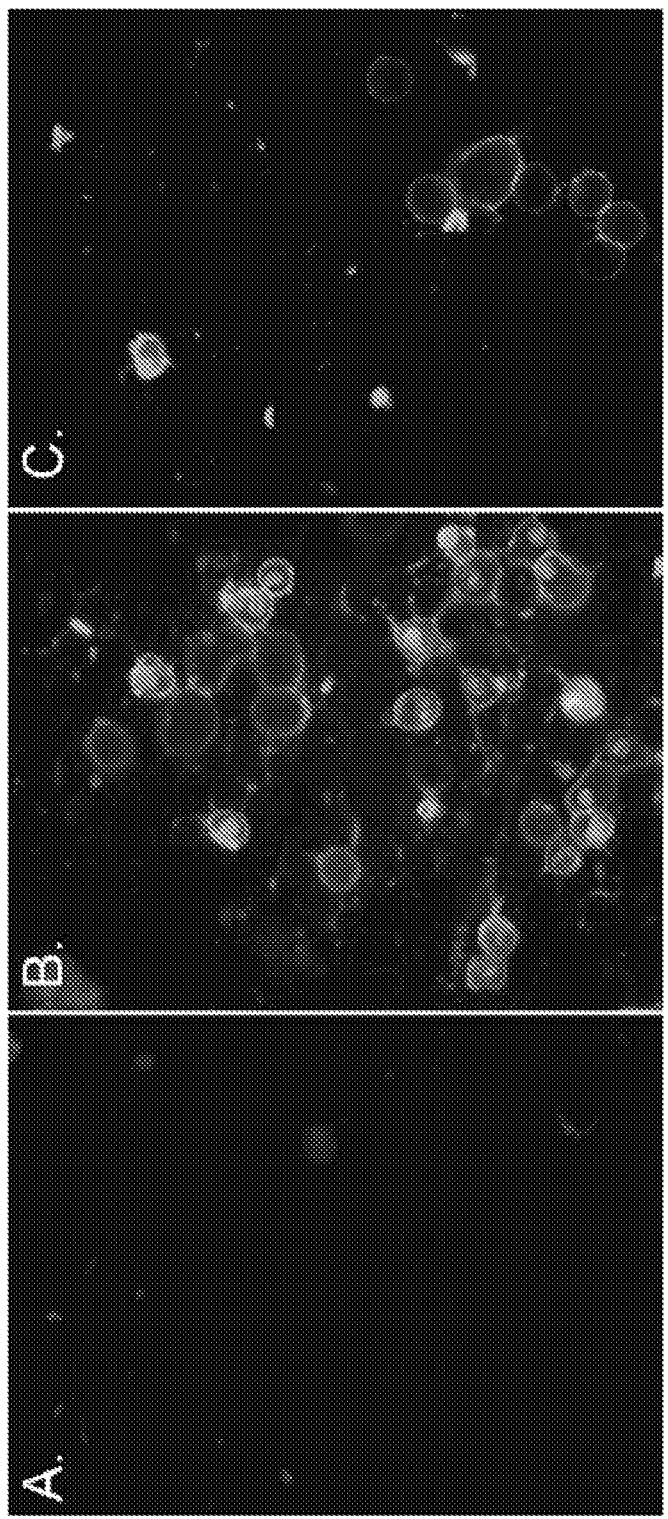
FIG. 19. SS-31 reduced tBHP-induced apoptosis as demonstrated by phosphatidylserine translocation. $N_2A$ cells were incubated with 50 μM tBHP for 6 h and stained with Annexin V and propidium iodide (PI). (A) Untreated cells showed little Annexin V stain and no PI stain. (B) Cells treated with tBHP showed intense Annexin V staining (green) in most cells. Combined staining with Annexin V and PI (red) indicate late apoptotic cells. (C) Concurrent treatment with 1 nM SS-31 resulted in a reduction in Annexin V-positive cells and no PI staining.

SS-31 Protected Against tBHP-Induced Apoptosis. (FIGS. 19 and 20)

The translocation of phosphatidylserine from the inner leaflet of the plasma membrane to the outer leaflet is observed early in the initiation of apoptosis. This can be observed with Annexin V, a phospholipid binding protein with high affinity for phosphatidylserine. FIG. 19A shows that untreated N2A cells showed little to no Annexin V staining (green). Incubation of N2A cells with 50 mM tBHP for 6 h resulted in Annexin V staining on the membranes of most cells (FIG. 19B). Combined staining with Annexin V and propidium iodide (red) showed many late apoptotic cells (FIG. 19B). Concurrent treatment of N2A cells with 1 nM SS-31 and 50 μM tBHP resulted in a reduction in Annexin V-positive cells and no propidium iodide staining (FIG. 19C), suggesting that SS-31 protected against tBHP-induced apoptosis.

Figure 20A:
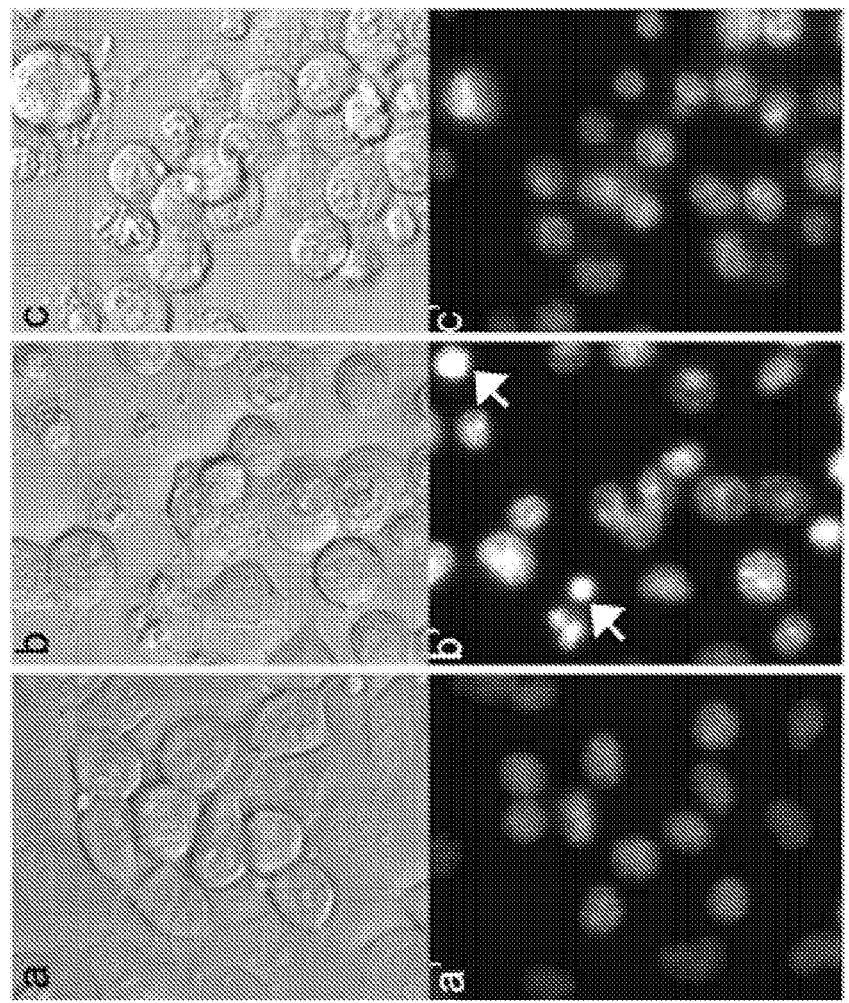
FIG. 20. SS-31 reduced tBHP-induced apoptosis as demonstrated by nuclear condensation. (A) $N_2A$ cells were treated with 50 μM tBHP alone or with SS-31 for 12 h. Cells were stained with Hoechst 33342 for 20 min., fixed, and imaged by fluorescent microscopy. (a) Untreated cells show uniformly stained nuclei (a'). (b) Cells treated with tBHP were smaller and showed nuclear fragmentation and condensation (b'). (c) Cells treated with tBHP and 1 nM SS-31 had less nuclear changes (c'). (B) SS-31 dose-dependently reduced percent of apoptotic cells in $N_2A$ cells. Apoptotic cells were counted using MetaMorph software. *$P<0.01$ compared to untreated cells; *$P<0.01$ compared to tBHP alone. (C) SS-31 dose-dependently reduced percent of apoptotic cells in SH-SY5Y cells. SH-SY5Y cells were treated with 25 μM tBHP for 24 h. *$P<0.01$ compared to untreated cells; *$P<0.01$ compared to tBHP alone.
Figure 20B:
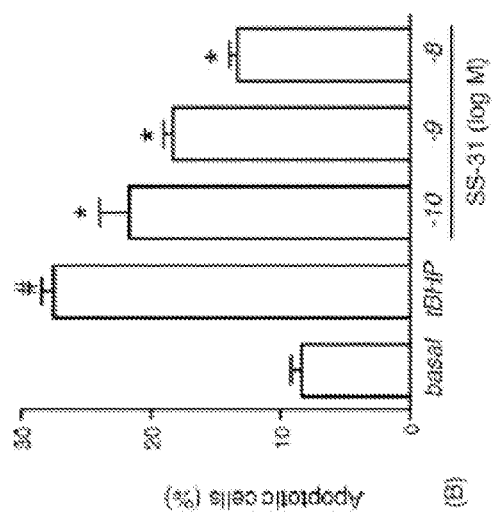

The morphological appearance of cells treated with tBHP was also consistent with apoptosis. N2A cells incubated with 50 μM tBHP for 12 h became rounded and shrunken (FIG. 20A, panel b). Staining with Hoechst 33324 showed increased number of cells with nuclear fragmentation and condensation (FIG. 20A, panel b). These nuclear changes were abolished by concurrent treatment with 1 nM SS-31 (FIG. 20A, panel c'). The number of apoptotic cells was dose-dependently reduced by concurrent treatment with SS-31 ($P<0.0001$) (FIG. 20B).

Figure 20C:
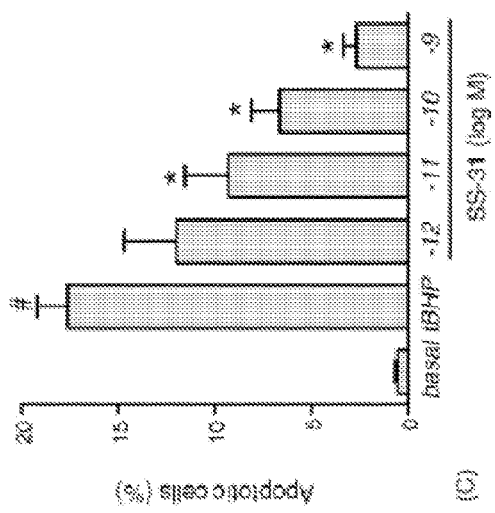

An increased number of cells with condensed nuclei was also observed when SH-SY5Y cells were treated with 25 μM tBHP for 24 h, and the number of apoptotic cells was dose-dependently reduced by concurrent treatment with SS-31 ($P<0.0001$) (FIG. 20C).

Example 23

SS-31 Protected Against tBHP-Induced Caspase Activation (FIG. 21)

Figure 21A:
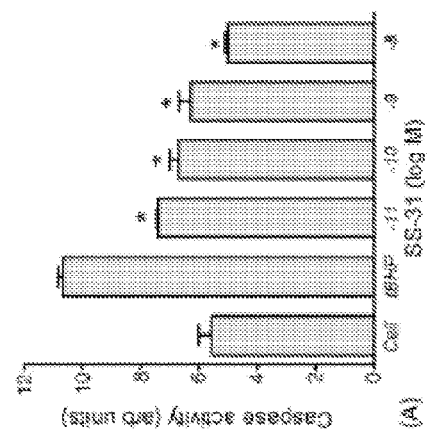
FIG. 21. SS-31 prevented caspase activation in $N_2A$ cells treated with tBHP. (A) incubation of $N_2A$ cells with 100 μM tBHP for 24 h resulted in a significant increase in pancaspase activity that was dose-dependently prevented by co-incubation with SS-31 (*$P<0.01$ compared to tBHP alone). (B) $N_2A$ cells were treated with 50 μM tBHP for 12 h and stained with caspase-9 FLICA™ kit containing red fluorescent inhibitor SR-LEHD-FMK and Hoechst 33342. (Panel a) Untreated cells showed no caspase-9 stain and uniformly stained nuclei. (Panel b) cells treated with tBHP showed intense caspase-9 activity (red) in cells that also show condensed nuclei. (Panel c) Cells treated with tBHP and 1 nM SS-31 showed fewer caspase-9 positive cells and fewer condensed nuclei.
Figure 21B:
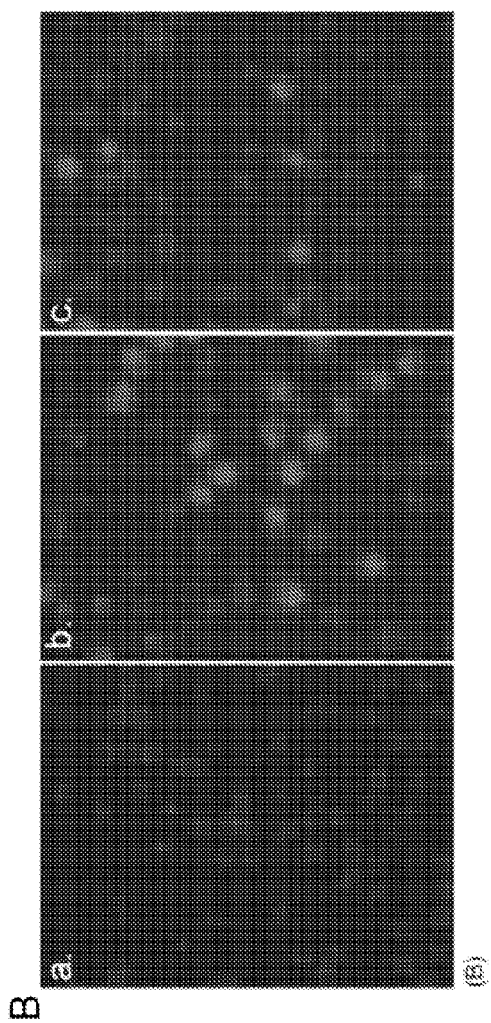

Incubation of N₂A cells with 100 μM tBHP for 24 h resulted in a significant increase in pan-caspase activity that was dose-dependently prevented by co-incubation with SS-31 ($P<0.0001$ (FIG. 21A). A N₂A cells treated with 50 μM tBHP for 12 h showed intense staining (red) for caspase-9 activity (FIG. 21B, panel b). Note that cells that show nuclear condensation all showed caspase-9 staining Concurrent incubation with 1 nM SS-31 reduced the number of cells showing caspase-9 staining (FIG. 21B, panel c).

Example 24

SS-31 Inhibited tBHP-Induced Increase in Intracellular ROS (FIG. 22)

Figure 22A:
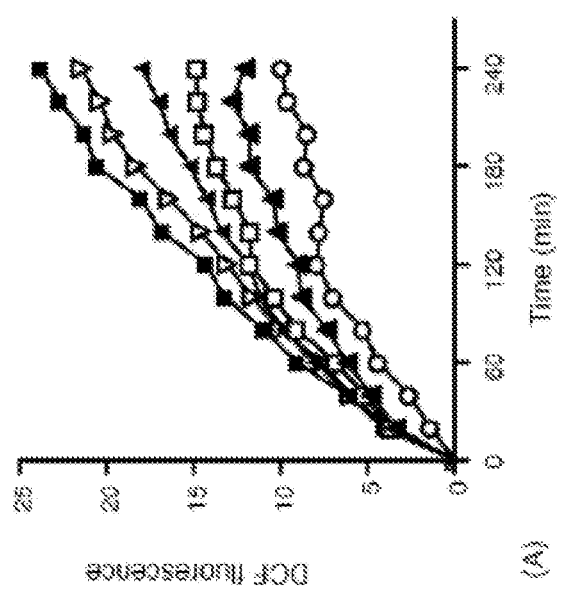
FIG. 22. SS-31 dose-dependently reduced intracellular ROS production in $N_2A$ cells treated with tBHP. (A) $N_2A$ cells were loaded with DCFDA, and then exposed to 100 μM tBHP alone, or with SS-31. Intracellular ROS was quantified by the formation of fluorescent DCF. Results shown are mean values (n=3). (B) $N_2A$ cells were plated in glass bottom dishes and treated with 50 μM tBHP, alone or with 1 nM SS-31, for 6 h. Cells were loaded with DCFDA (10 μM) and imaged by confocal laser scanning microscopy using ex/em of 495/525 nm. (C) Effect of 1 nM SS-31 in reducing intracellular ROS induced by 50 μM tBHP (*$P<0.001$ compared to untreated cells; *$P<0.05$ compared to tBHP alone).
Figure 22B:
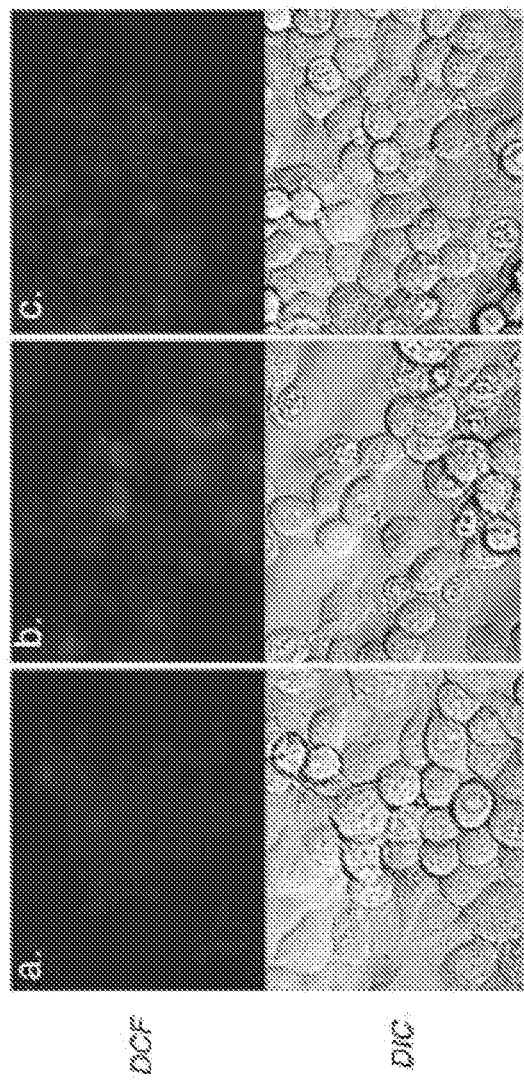
Figure 22C:
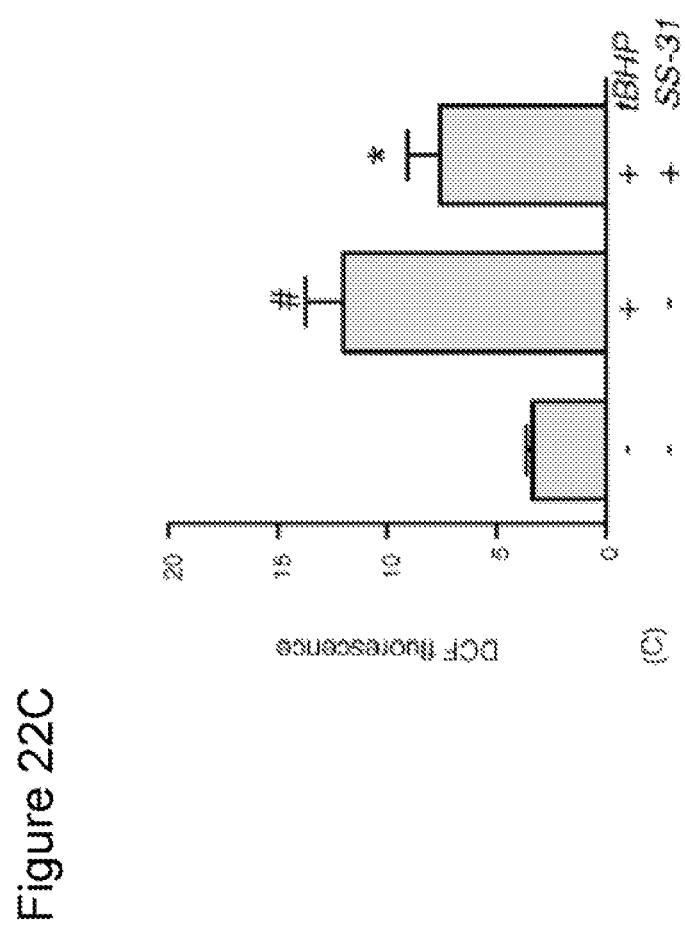

Intracellular ROS production is an early and critical event in oxidant-induced cytotoxicity. Treatment of N₂A cells with 100 μM tBHP resulted in rapid increase in intracellular ROS, as measured by DCF fluorescence, over 4 h at 37° C. (FIG. 22A). Concurrent treatment with SS-31 dose-dependently reduced the rate of ROS production, with 1 nM SS-31 effectively reducing ROS production by >50%. The reduction in intracellular ROS was confirmed by fluorescent microscopy with DCF (FIG. 22B). Treatment with N₂A cells with 50 μM tBHP caused significant increase in DCF fluorescence (green), and this was significantly reduced by co-incubation with 1 nM SS-31 (FIG. 22C).

Example 25

SS-31 Prevented Loss of Mitochondrial Function Caused by tBHP (FIG. 23)

Figure 23A:
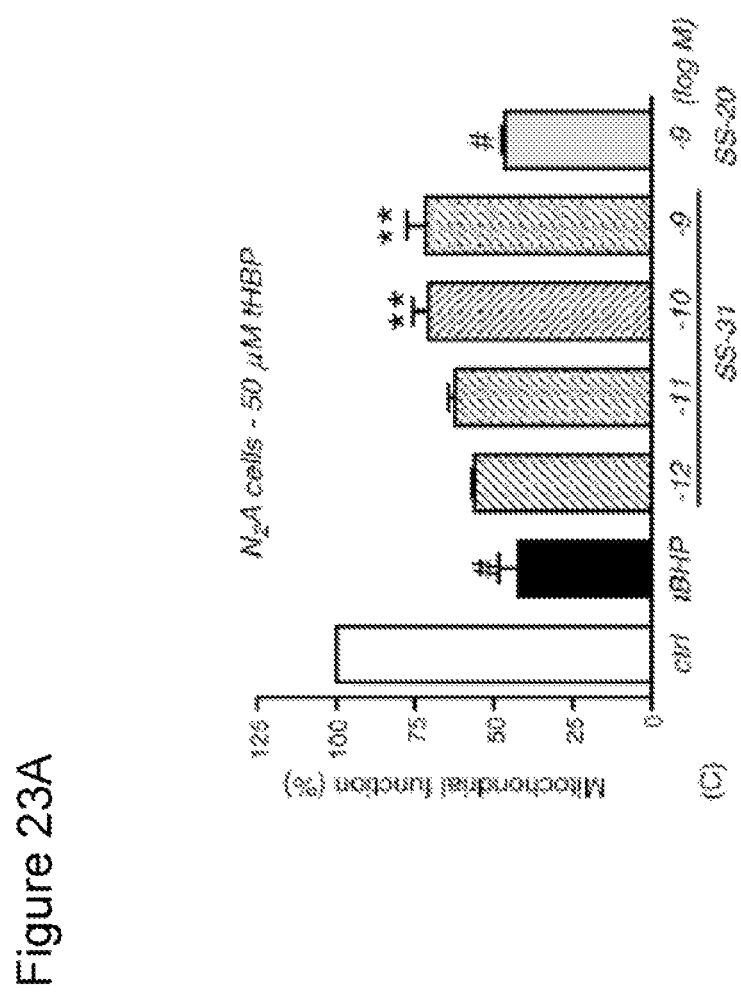
FIG. 23. SS-31 protected against tBHP-induced mitochondrial viability. (A) SS-31 protected mitochondrial viability in $N_2A$ cells treated with tBHP for 24 h. Mitochondrial viability was evaluated using the MTT assay (*$P<0.01$ compared to untreated cells, *$P<0.05$, $P<0.01$ compared to tBHP alone). (B) SS-31 protected mitochondrial viability in SH-SY5Y cells treated with tBHP for 25 h (*$P<0.01$ compared to untreated cells; **$P<0.01$ compared to tBHP alone).
Figure 23B:
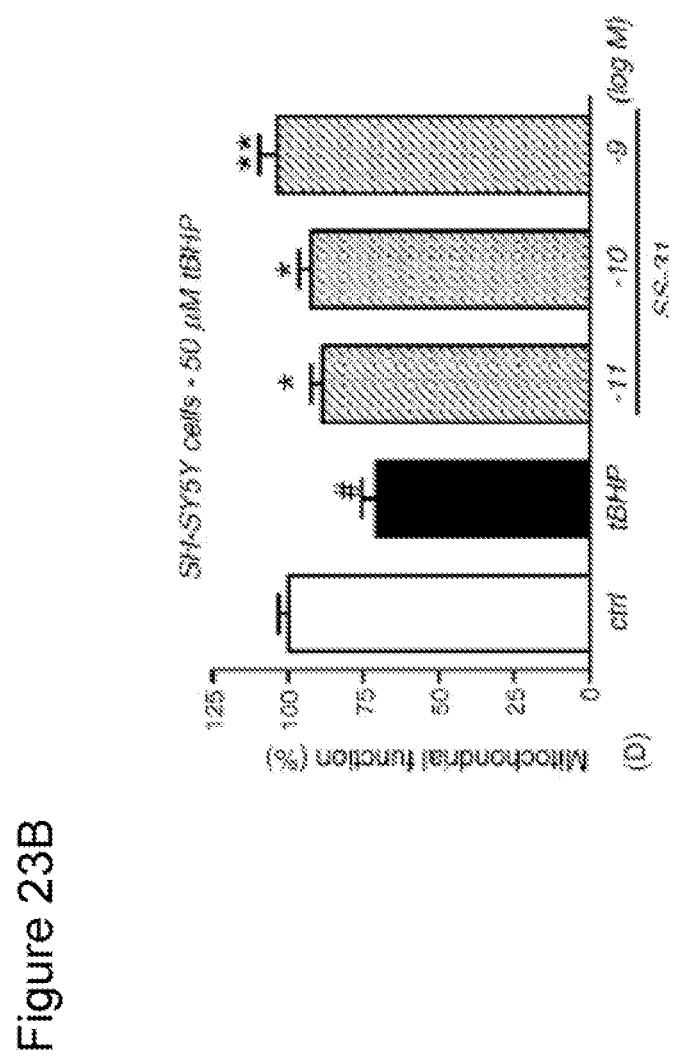

Treatment with low doses of tBHP (50-100 μM) for 24 h resulted in a significant decrease in mitochondrial function as measured by the MTT assay in both cell lines. Only viable mitochondria containing NADPH dehydrogenase activity are capable of cleaving MTT to the formazan. A 50 μM tBHP induced 50% loss of mitochondrial function in N₂A cells (FIG. 23A, $P<-0.01$) and 30% loss of mitochondrial function in SH-SY5Y cells (FIG. 23B, $P<0.01$). Concurrent treatment with SS-31 dose-dependently reduced tBHP-induced mitochondrial toxicity in both N₂A (FIG. 23A; $P<0.0001$) and SHSY5Y cells (FIG. 23B; $P<0.0001$). The non-scavenging peptide, SS-20, did not protect against tBHP-induced mitochondrial dysfunction in N₂A cells (FIG. 23A). Treatment of N₂A cells with SS-31 alone had no effect on mitochondrial function.

Example 26

Figure 24:
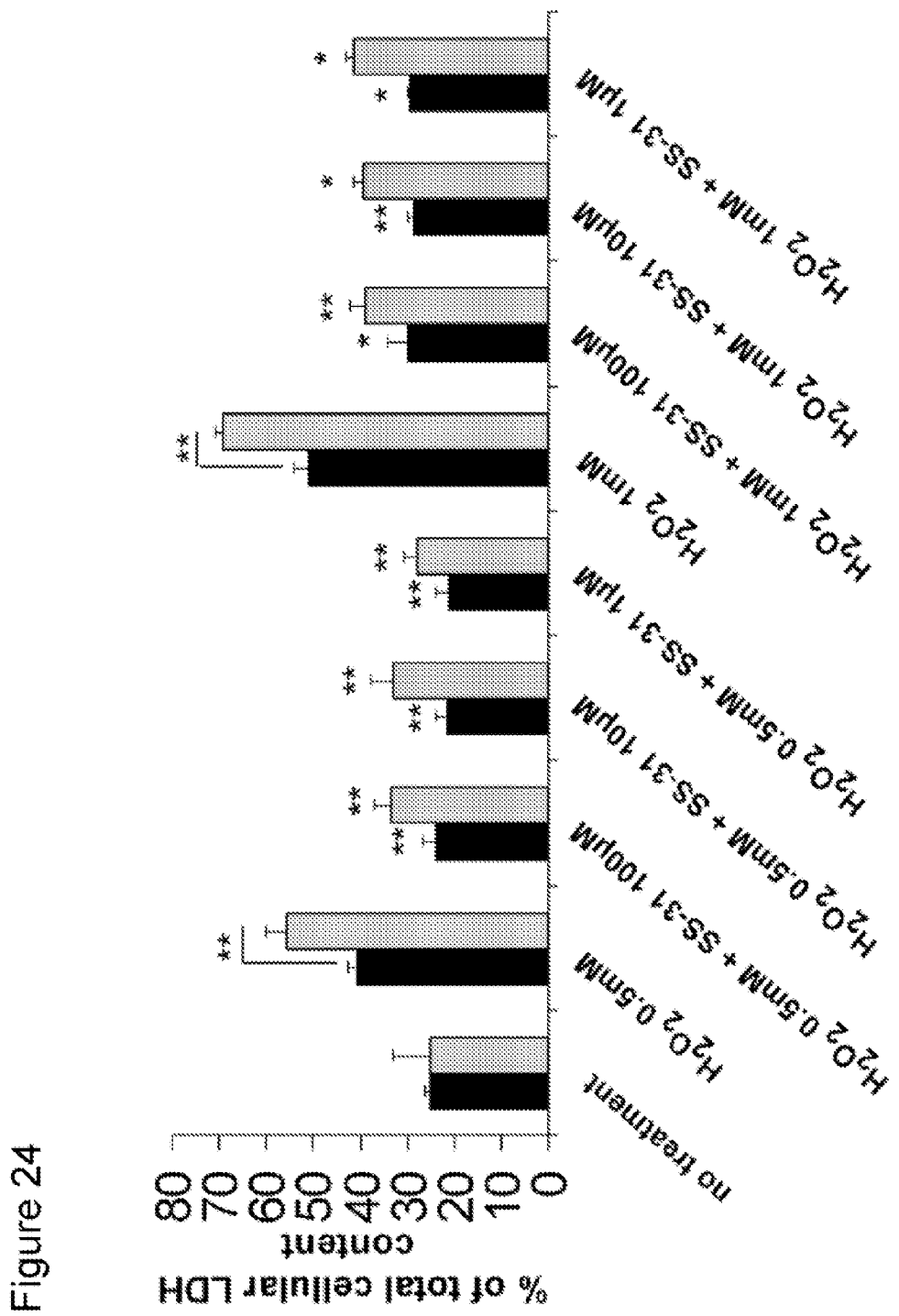
FIG. 24. Increased hydrogen peroxide ($H_2O_2$) sensitivity of G93A-SOD transfected murine neuroblastoma ($N_2A$) cells as compared to wildtype SOD-transfected $N_2A$ cells after addition of 0.5 or 1 mM $H_2O_2$ for 1 h. Cell death was quantified by measurement of the percentage of $H_2O_2$-induced LDH release of total cellular LDH-content. $H_2O_2$-induced LDH release was significantly reduced by treatment of the cells with 1 to 100 μM SS-31 after incubation with $H_2O_2$. Values are means+S.D., n=4-5, *$p<0.1$, **$p<0.05$, Student's t-test. Black columns wildtype-SOD1-transfected cells, grey columns: G93A-SOD1 transfected $N_2A$ cells.

Increased Hydrogen Peroxide ($H_2O_2$) Sensitivity of G93A-SOD Transfected Murine Neuroblastoma (N2a) Cells (FIG. 24)

In a cell culture model of N₂A cells overexpressing either wild type or mutant (69A-SOD1, the mutant cells were significantly more sensitive to $H_2O_2$-induced cell death both at 0.04 mM and 1 mM concentrations. This cell-death was significantly reduced by addition of SS-31 in concentration between 1 and 100 μM to the medium 1 h after exposure to $H_2O_2$ (FIG. 24).

Example 27

Figure 25A:
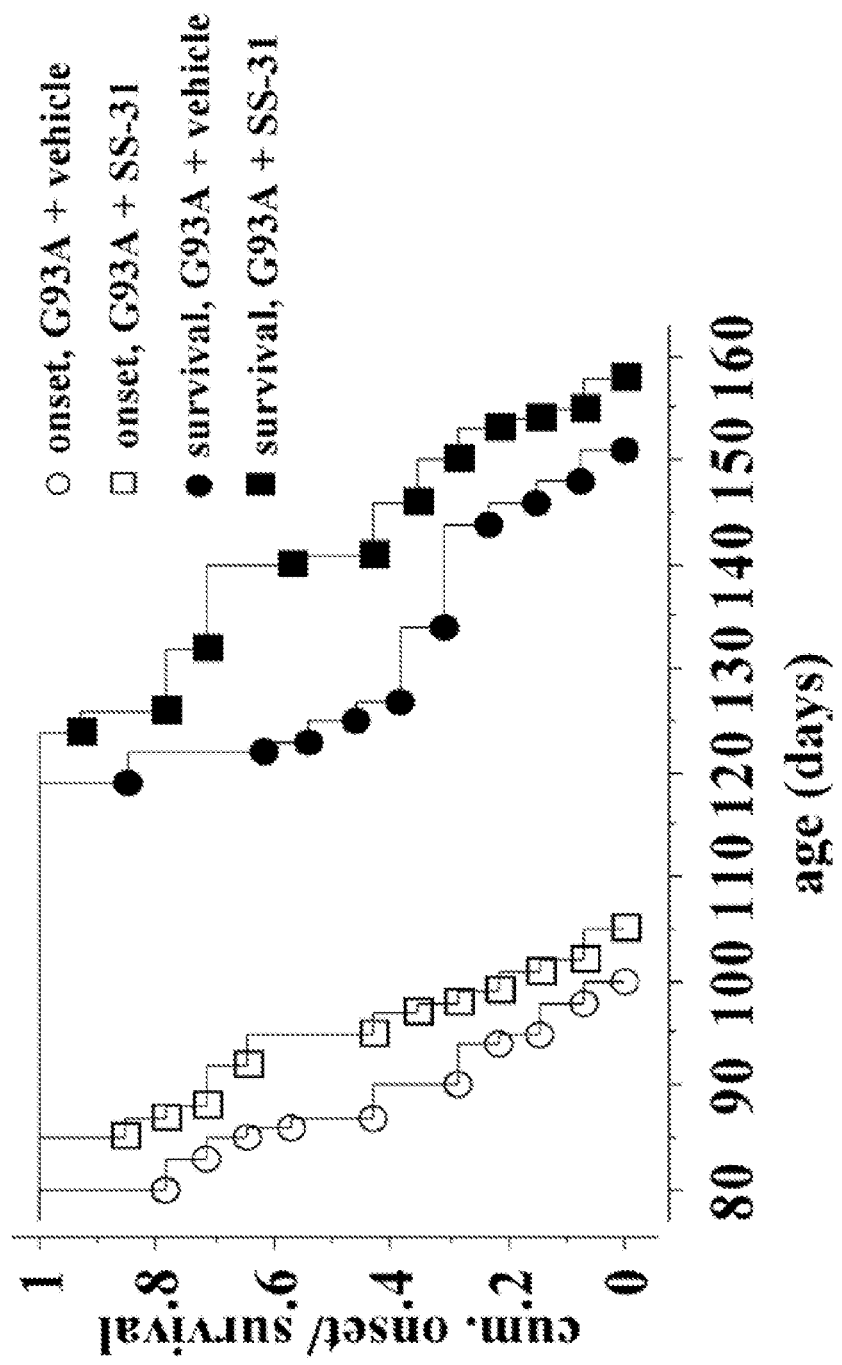
FIG. 25. (A) Cumulative probability of disease on set and survival with SS-31 5 mg/kg/day treatment (n=14) started at symptom onset as compared to vehicle treatment (n=14). Survival was significantly improved by SS-31 ($p<0.05$, Mantel-Cox log-rank test). (B) Mean survival (days) of G93A mice treated with vehicle or SS-31 5 mg/kg/day. (Data are mean±SD, $p<0.05$, Student's t-test).
Figure 25B:
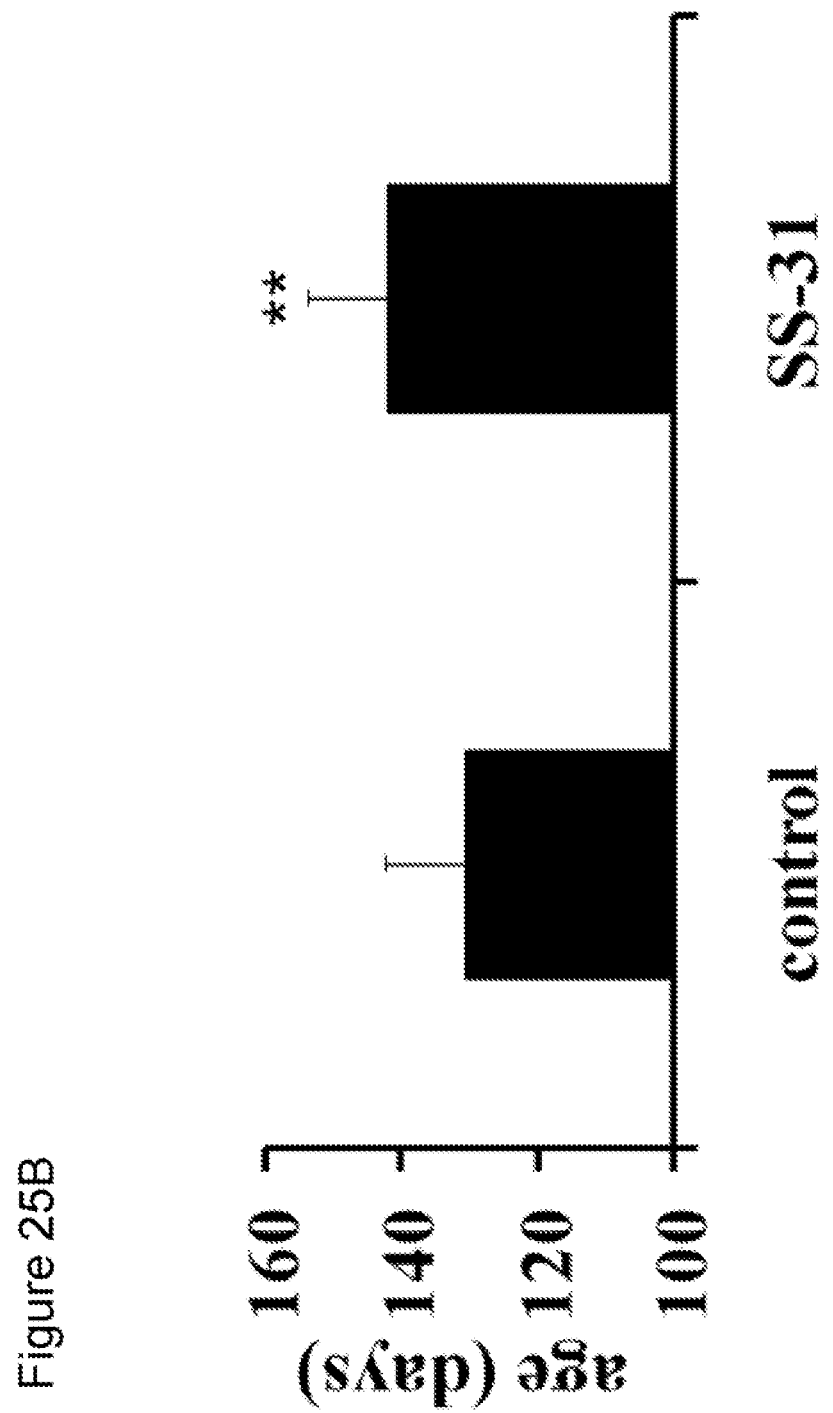

SS-31 Increased Survival of G93A Transgenic Familial ALS Mice (FIG. 25)

Treatment with 5 mg-kg SS-31 i.p. started at 30 days of age of G93A transgenic familial amyotrophic lateral sclerosis (ALS) mice (high copy number, B6SJL-Tg(SOD1-G93A) 1Gur/J) led to a significant delay of disease onset as defined by the appearance of tremor and hind limb clasping as well as deterioration in the rotarod performance, the average age of onset in the control group was 88+7 days, in the SS-31 treated group 95+6 days (p<0.05, Logrank (Mantel-Cox)). Survival was significantly increased by SS-31 treatment from 130±12 to 142+12 day (i.e., 9%) (p<0.05, Logrank (Mantel-Cox)) (FIG. 25). Treatment was well tolerated and no side effects were observed. There was a gender effect on survival which has been observed in previous studies with this model as well in G93A mice in this background with males having a shorter life span than females (average of 5 days). This gender difference was seen in both groups and not modified by the treatment.

Example 28

Figure 26:
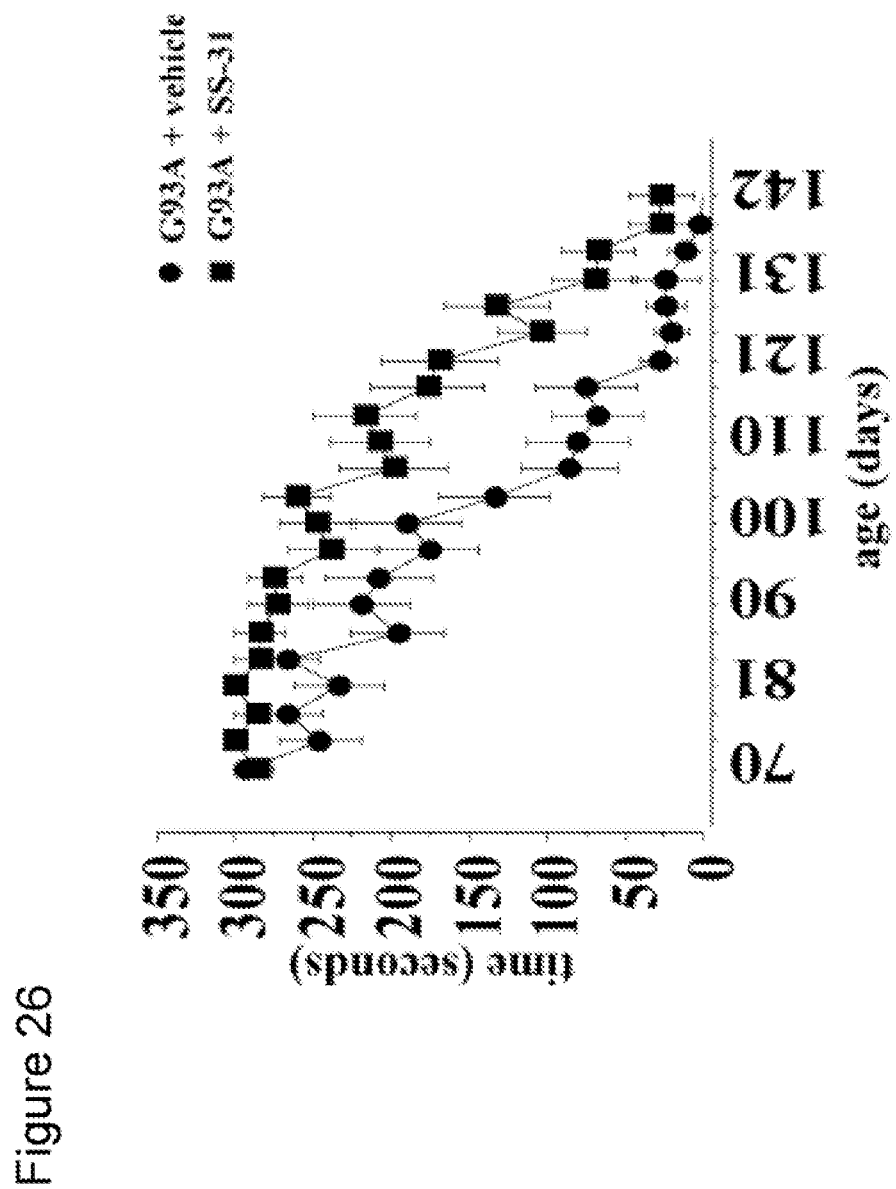
FIG. 26. Effect of SS-31 mg/kg/day on motor performance (seconds) tested by rotarod (Values are mean±standard error of means of the mice still alive at the respective time point): it was significantly improved between day (d) 110 and day 130 in SS-31-treated animals as compared to the vehicle-treated group ($p<0.005$, Repeated Measures ANOVA followed by Fisher's PLSD).

Effect of SS-31 on Motor Performance of G93A Transgenic Familial ALS Mice (FIG. 26)

Motor performance was significantly improved in the SS-31 treated mice between day 100 and 130 (p<0005, Repeated measures ANOVA followed by Fisher's PLSD) (FIG. 26).

Example 29

Figure 27:
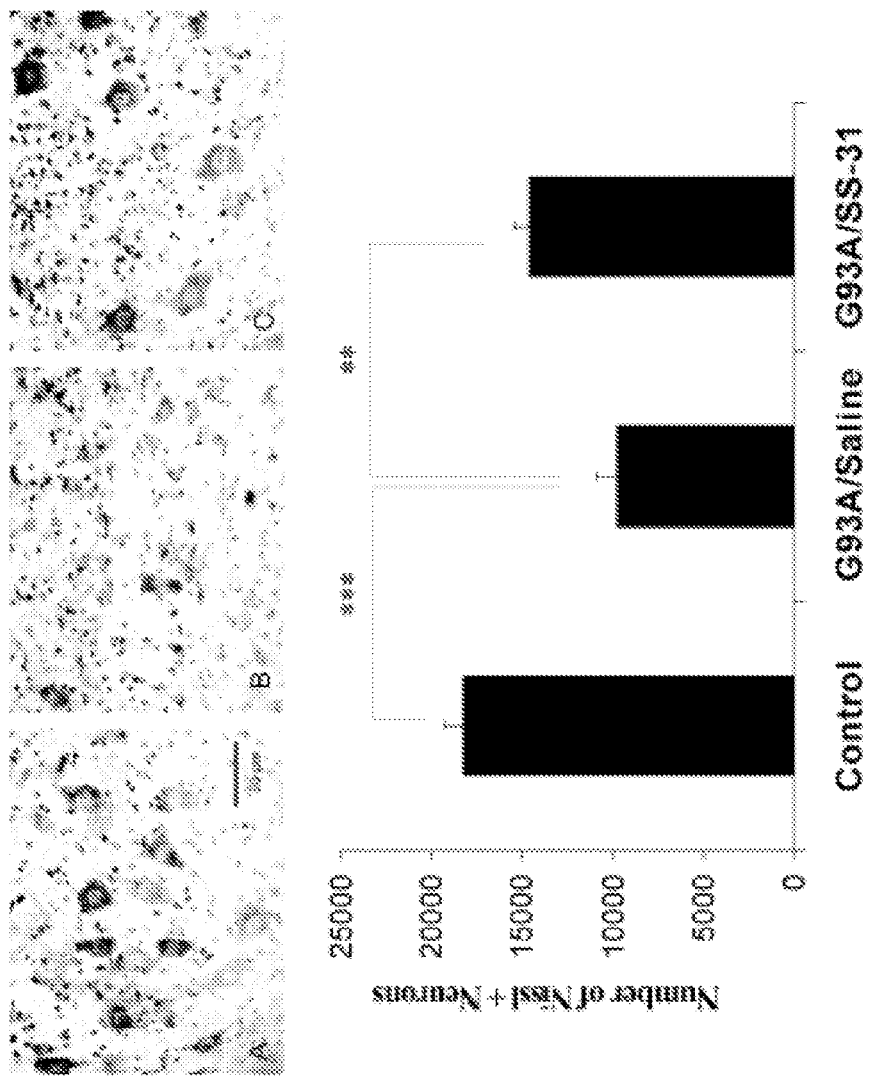
FIG. 27. Attenuation of motor neuron loss by SS-31 in the ventral horn of the lumbar spinal cord of G93A mice. Photomicrographs show cresyl violet stained sections through the ventral horn of the lumbar spinal cord from non-transgenic control (A) and G93A mice treated with vehicle (PBS) (B) or SS-31 (C) at 110 days of age. Stereological analysis revealed significantly reduced numbers of surviving neurons in G93A mice treated with vehicle as compared to non-transgenic controls (*, $p<0.001$). This cell loss was significantly ameliorated by treatment with SS-31 (, $p<0.01$). Values are mean±standard error of means. Differences among means were analyzed using ANOVA followed by Newman-Keuls post hoc test.
Figure 28:
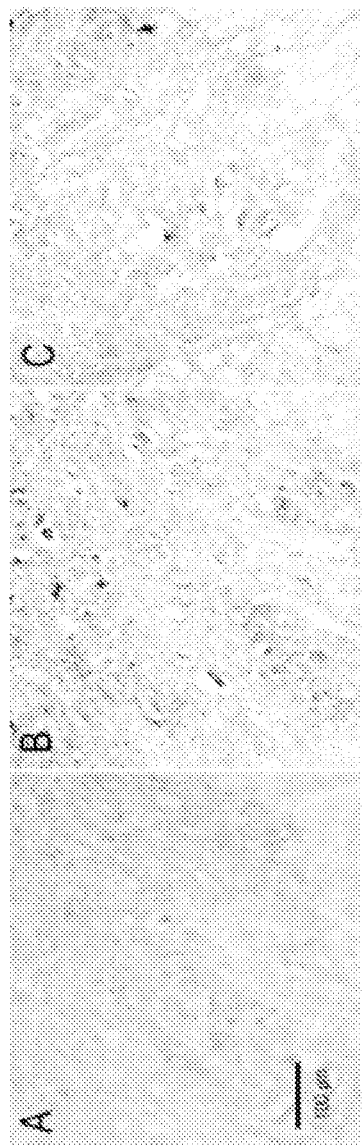
FIG. 28. 4-hydroxynonenol immunostaining Photomicrographs of representative sections through the ventral horn of the lumbar spinal cord of wild-type control (A), and G93A mice treated with vehicle (B) or SS-31 (C) show generalized reduction of 4-hydroxynonenal staining in neurons and neurophils in drug-treated mice.
Figure 29:
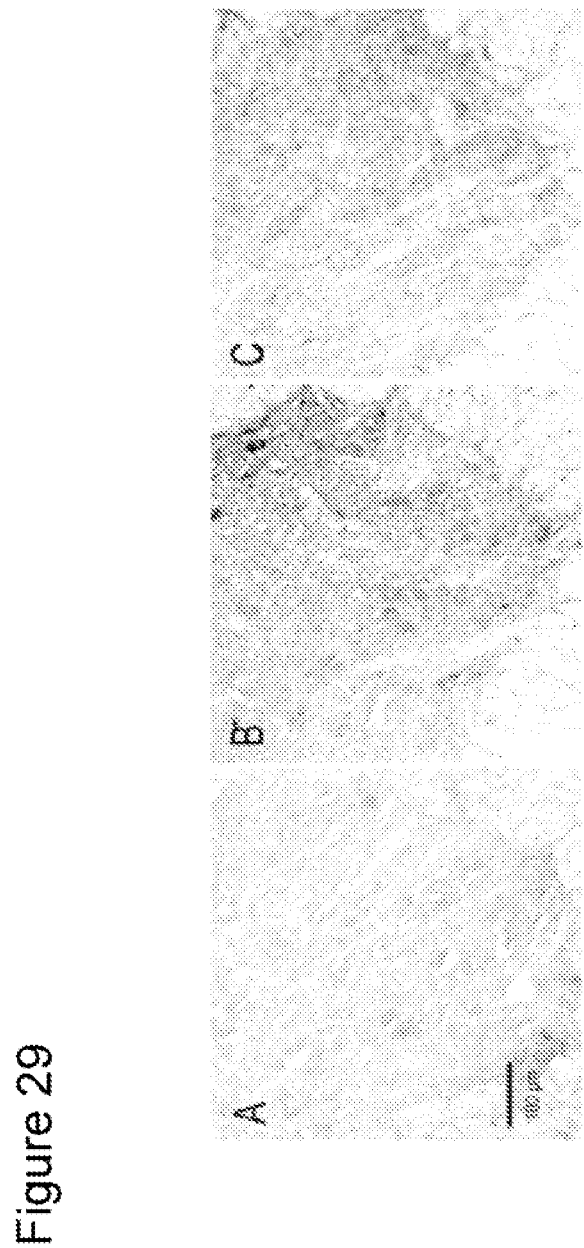
FIG. 29. Nitrotyrosine immunostaining. Photomicrographs of representative sections through the ventral horn of the lumbar spinal cord of wild-type control (A), and G93A mice treated with vehicle (B) or SS-31 (C) show generalized reduction of nitrotyrosine staining in neurons and neurophils in drug-treated mice.

Attenuation of Motor Neuron Loss by SS-31 in the Ventral Horn of the Lumbar Spinal Cord of G93A Mice. (FIGS. 27, 28 and 29)

Stereological cell counts in the lumbar spinal cord revealed a significant cell loss in the vehicle treated G93A mice as compared to non-transgenic littermate control animals. The cell loss was significantly ameliorated by administration of SS-31 (FIG. 27). Immunostaining for markers of oxidative and nitrosative stress (4-hydroxynonenenal, 3-nitrotyrosine) showed increased levels of lipid peroxidation and protein nitration in the spinal cord of G93A as compared to control mice. This was markedly reduced in the SS-31 treated mice (FIG. 28, 4-hydroxynonenenal; FIG. 29, 3-nitrotyrosine).

Example 30

Figure 30:
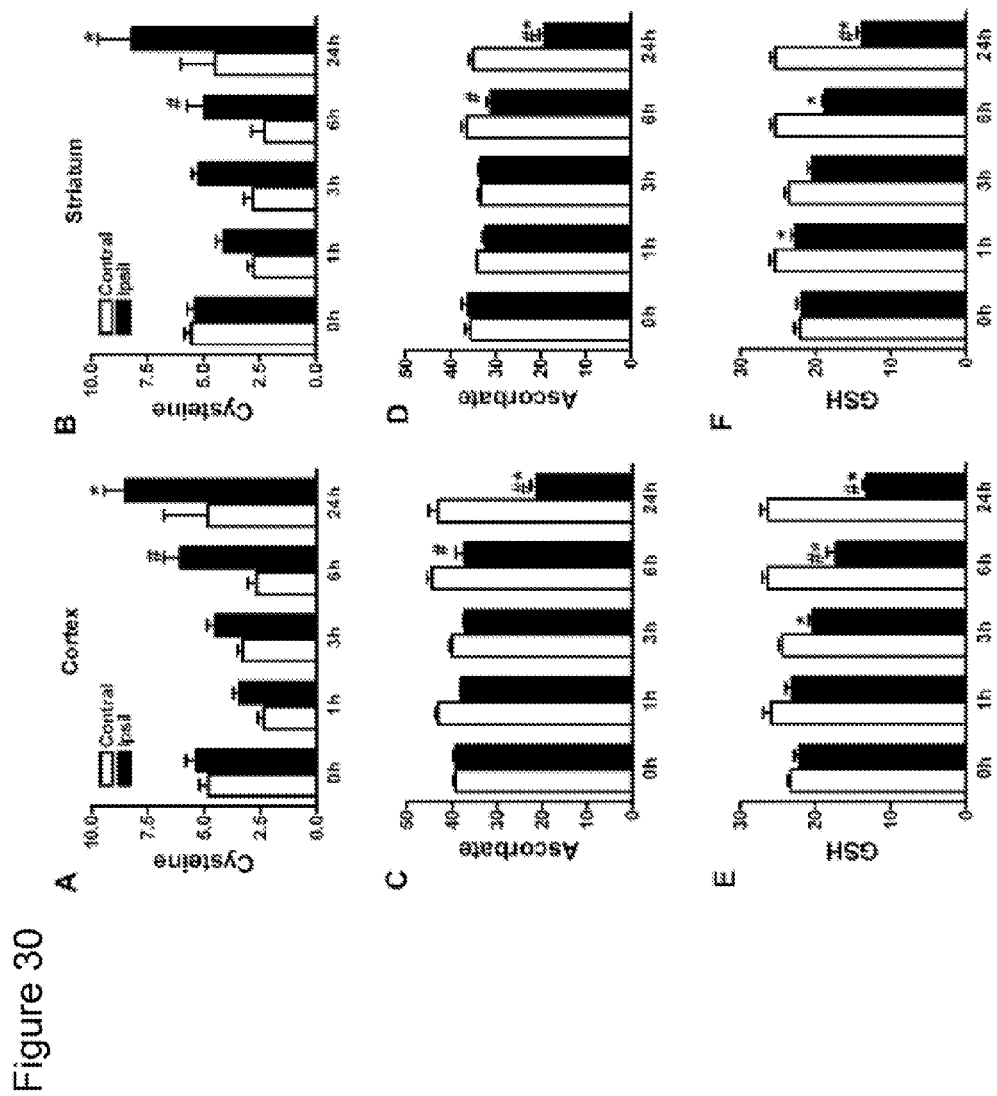
FIG. 30. Temporal changes of cysteine (A, B), ascorbate (C, D) and GSH (E, F) levels in post-ischemic brain. C57BL/6 mice were subjected to 30 min MCAO. Values are expressed as nmol/mg protein in cortex (A, C, E) and striatum (B, D, F). Error bars indicate SEM (n=4 animals per group). #<0.05 vs 0 h Contral, *p<0.05 vs corresponding Contral, one-way ANOVA with post hoc Fisher's PLSD test. Contral, contralateral side; Ipsil, ipsilateral side; 0 h, sham non-ischemic animal.

Reduced Ascorbate and GSH Levels in Post-Ischemic Brain (FIG. 30)

Ascorbate and GSH, in addition to cysteine were determined in the postischemic cortex and striatum. While cysteine levels were generally decreased in both hemispheres after ischemia, they were significantly higher in the ipsilateral side compared to the contralateral side (FIGS. 30A and B). By contrast, the levels of ascorbate and GSH, the major water-soluble intracellular antioxidants in brain, were progressively decreased in the ipsilateral side within a few hours of reperfusion (FIGS. 30C-F). Antioxidant reduction was significant in both cortex and striatum at 6 h and was further reduced at 24 h, at a time when the infarct is visible.

Example 31

Figure 31:
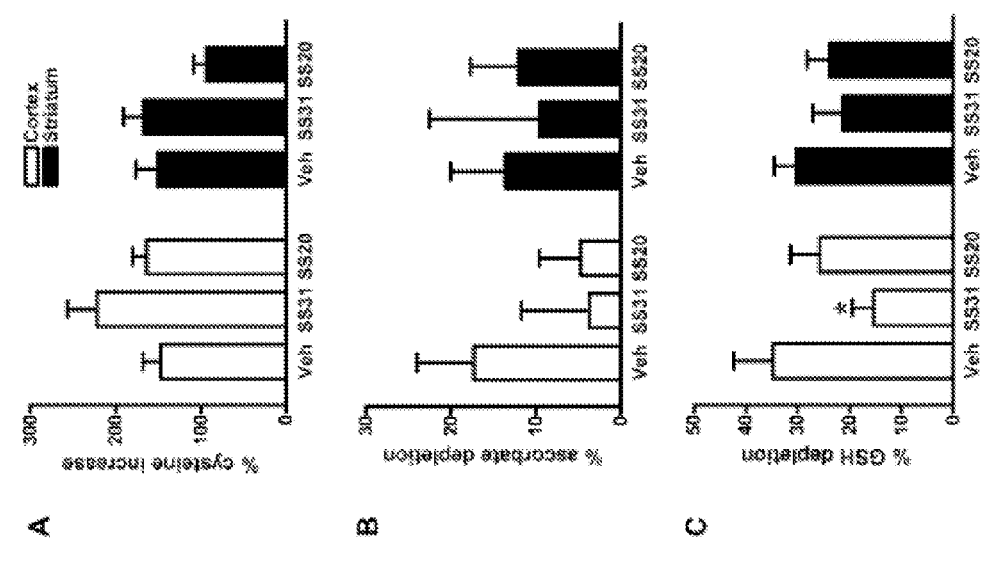
FIG. 31. Effect of SS-31 peptide on ischemia-induced changes in cysteine (A) ascorbate (B), and GSH (C) levels, C57BL/6 mice were subjected to 30 min MCAO and treated with vehicle, SS-31 (2 mg/kg body weight) or SS-20 (2 mg/kg body eight) peptide immediately after reperfusion. Mice were sacrificed at 6 h postischemia. Values are expressed as percent increase (cysteine) or percent depletion (ascorbate and GSH) in ipsilateral side versus contralateral side. Error bars indicate SEM (n=4-6 animals per group). Note that a difference was observed in percent GSH depletion SS-31-treated cortex. *p<0.05 vs vehicle treated group (Veh), one-way ANOVA with post hoc Fisher's PLSD test.

Treatment with SS-31, But Not SS-20, Attenuates GSH Depletion in Post-Ischemic Cortex (FIG. 31)

To test the efficacy of SS-3 Ion redox status, cysteine, ascorbate and GSH levels were determined 6 h after 30 min transient middle cerebral artery occlusion (MCAO) in mice treated intraperitoneally (i.p.) with saline (vehicle), SS-31 (2 mg/kg) or SS-20 (2 mg/kg) upon reperfusion. Values in FIG. 31 are expressed as percent increase (cysteine) and percent depletion (ascorbate and GSH) in the ipsilateral side compared to the contralateral side. Absolute values were originally expressed as nmoles/mg protein as shown in FIG. 30 and converted to percent difference. The percent ipsilateral cysteine increase was similar among vehicle-, SS-31-, and SS-20-treated groups (FIG. 31A). Percent ipsilateral depletion of ascorbate was marginally but not significantly affected in both SS-31 and SS-20-treated animals (FIG. 31B). In contrast, ischemia-induced GSH depletion in the cortex was significantly attenuated in SS-31-treated animals compared to the vehicle-treated group (FIG. 31C).

The degree of ipsilateral GSH depletion in SS-20-treated mice was not significantly different from that of vehicle-treated mice (FIG. 31C). The data show that SS-31 assists in maintaining antioxidant status and protects against ischemia-induced depletion of GSH in the cortex.

Example 32

Treatment with SS-31 Peptide Reduces Infarct Size and Swelling (FIG. 32)

To address whether SS-31-induced attenuation in GSH depletion is associated with neuroprotection, mice were subjected to 30 or 20 min MCAO and then treated with vehicle or SS-31 (2 mg/kg, i.p.) upon reperfusion) and at 6 h, 24 h, 48 h after MCAO. Infarct volumes and hemispheric swelling were determined at 3 days after ischemia. SS-31 treatment resulted in moderate but significant reduction in infarct volume following both 30 min (24% reduction) and 20 min (30% reduction) ischemia, (FIGS. 32A-C). Treatment with SS-31 also significantly attenuated hemispheric swelling in both 30 and 20 min ischemic paradigms (FIG. 32D). There was no difference in cerebral blood flow (CBF) reduction during MCAO (FIG. 32E) and reperfusion at 10 min (FIG. 32F) between vehicle- and SS-31-treated groups, indicating that the neuroprotective effect by SS-31 occurs via mechanisms other than altered CBF during and after the ischemic insult.

Example 33

Islet Cell Uptake of SS-31 (FIG. 33)

Figure 33A:
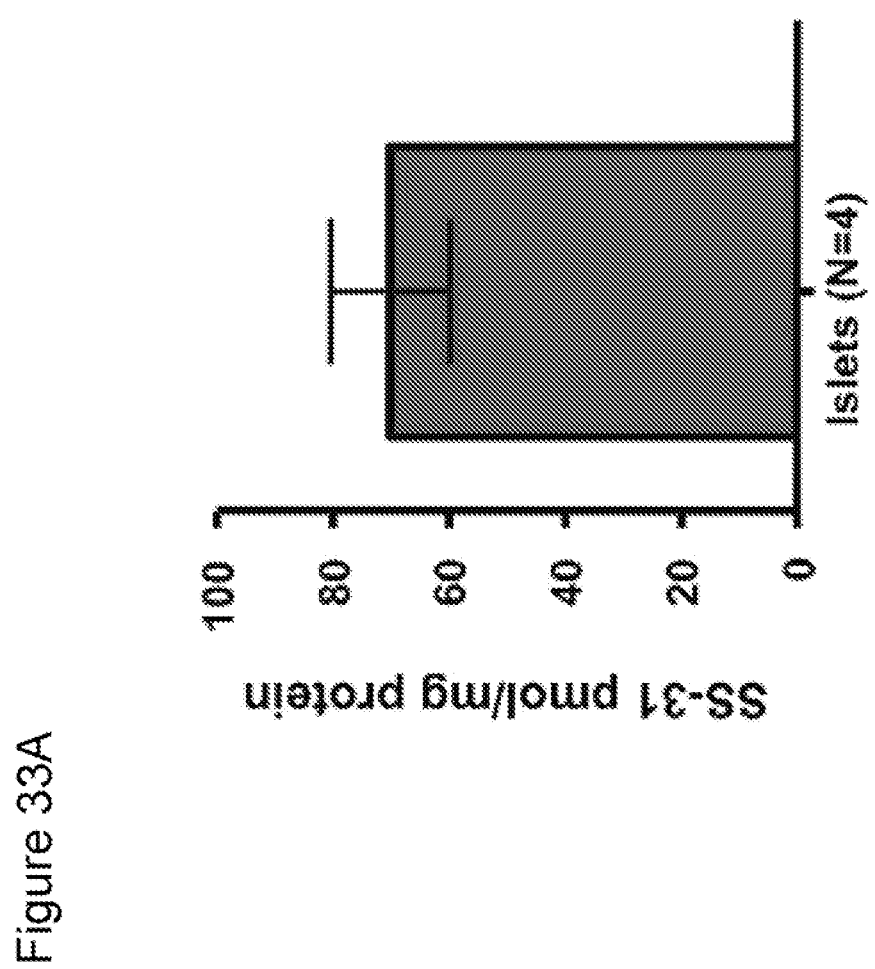
FIG. 33. SS peptides penetrate islet cells, co-localize with mitochondria and preserve islet mitochondrial membrane potential. (A) Islet cell uptake of SS-31. DBA/2 islet cells were incubated with 1 nM of tritium labeled SS-31 and 1 μM unlabeled SS-31 at 37° C. for 1 h. Following incubation, radioactivity was measured in the medium and in cell lysates and the radioactive counts in the medium were subtracted from radioactive counts in the cell lysate and normalized to protein content. In four consecutive experiments, the mean± (SE) [$^3$H]SS-31 uptake was 70.2+/31 10.3 μmol/mg, of proteins (B) SS-31 preserves islet mitochondrial potential. DBA/2 mice were treated with SS-31 (3 mg/kg s.c. BID) or vehicle control 24 hours prior to pancreas harvest for islet isolation. SS-31 treated groups had 1 nM SS-31 added to the islet isolation reagents. Following isolation, TMRM uptake was evaluated using confocal laser scanning microscopy. Fluorescent (i) and phase (ii) images of TMRM uptake in control mice demonstrate reduced fluorescent uptake indicating mitochondrial depolarization. In sharp contrast, fluorescent (iii) and phase (iv) images of TMRM uptake in SS-31 treated mice demonstrate increased uptake and preserved mitochondrial potential indicative of SS-31 protective effect.

Islets are tightly adherent cell clusters and entry of peptides/proteins may be impaired given their architecture. FIG. 33A shows that SS-31 readily penetrates intact mouse islets; in four consecutive experiments, the mean (±SE) of [$^3$H]SS-31 uptake was 70.2±10.3 pmol/mg of protein.

Example 34

SS-31 Prevents Mitochondrial Depolarization (FIG. 33)

Figure 33B:
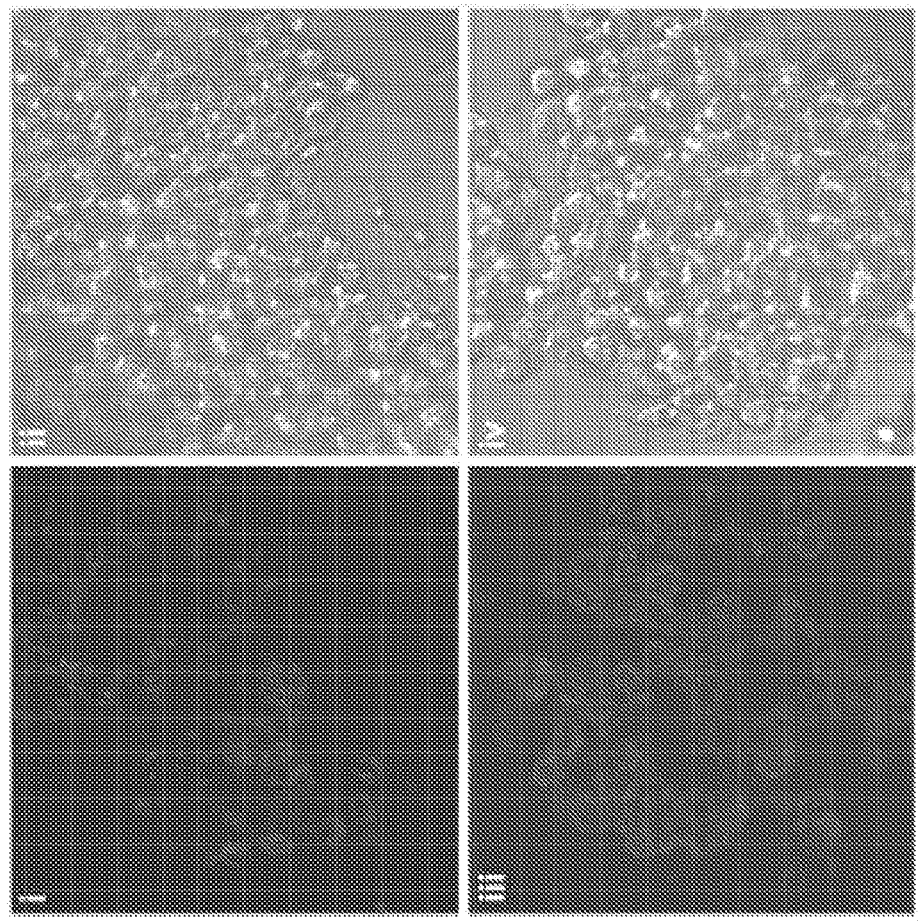

Mitochondrial depolarization and the release of cytochrome c into the cytoplasm are critical antecedent events to cell death. TMRM, a fluorescent cationic indicator is taken up into mitochondria in a potential dependent manner. FIG. 33B confocal laser scanning microscopic imaging of TMRM treated islets shows that the islets from mice treated with SS-31 exhibit greater uptake of TMRM compared to islets from mice not treated with SS-31.

Example 35

Optimization of Islet Isolation with SS-31

To investigate whether the SS-31 optimizes islet isolation and results in increased islet yield, islet donor mice were pre-treated with SS-31. SS-31 resulted in a significantly higher islet cell yield compared to untreated mice the mean± (SE) islet yield from the pancreata harvested from SS-31 pre-treated mice was 291±60 islets per pancreas (N=6 separate islet isolations from 28 pancreata) compared to 242±53 islets per pancreas retrieved from the control mice (N=6 separate islet isolations from 30 pancreata) (P=0.03, Two-tailed Pvalue calculated with Mann-Whitney test).

Example 36

Figure 34C:
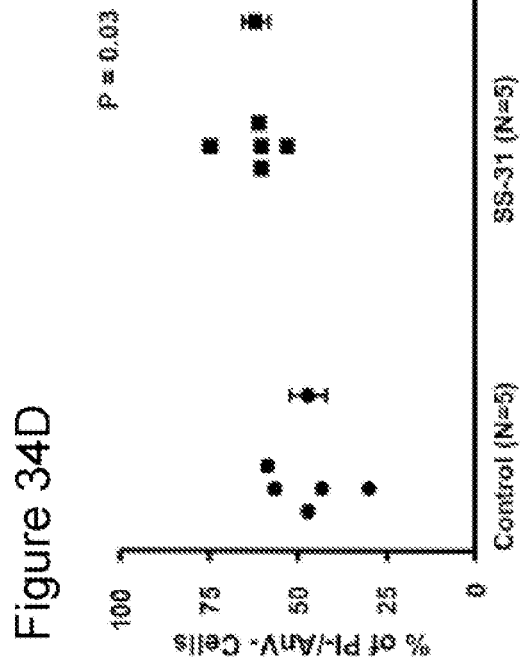
FIG. 34. SS-31 reduces islet cell apoptosis. DBA/2 mice were pre-treated (24 and 12-hours hours prior to pancreas harvest and islet isolation) with SS-31 (3 mg/kg, s.c., BID) or vehicle control. SS-31 (1 nM was added to reagents used for the isolation of islets from SS-31-treated mice. The islets were dissociated in to single cells with trypsin/EDTA and were stained with Annexin V-FITC (AnV) and propidium iodide (PI) and analyzed with the use of dual parameter low cytometry. (A) Percentage of cell undergoing early apoptosis (AnV+cells); P=0.03. (B) Percentage of cells undergoing late apoptosis/early necrosis (AnV+/PI+cells); P=0.03. (C) Percentage of necrotic cells (PI+cells); P=1.0 (D) Percentage of viable cells (AnV−/PI−cells); P=0.03. Data from individual pancreatic islet isolations and mean±SE are shown, N=number of separate islet isolations. Two-tailed P-values were calculated using Mann-Whitney t-test.
Figure 34D:
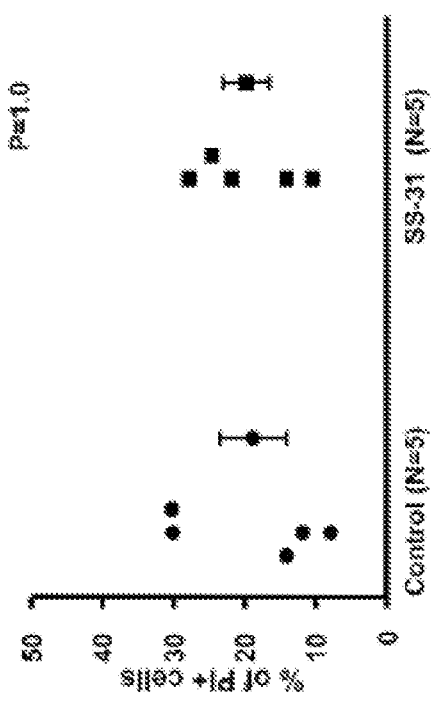

SS-31 Reduces Islet Cell Apoptosis (FIG. 34)

SS-31 treatment, in addition to enhancing islet yield resulted in a significant decrease in early as well as late, islet cell apoptosis. Dual parameter flow cytometry analyses of islet cells stained with both Annexin V and propidium iodide demonstrated that the treatment of islet donor mice with SS-31 reduced the percentage of early apoptotic cells (Annexin V alone positive cells) from 11.4±2.4% to 5.5±1.0% (FIG. 34A, P=0.03). SS-31 treatment reduced late apoptosis/early necrosis (Annexin V+/PI+cells) from 22.7±4.7% to 12.6±1.8 (FIG. 34B, P=0.03) and increased islet cell viability (Annexin V−/PI−cells) from 47±5.1% to 62±3.5% (FIG. 34D, P=0.03)). SS-31 treatment of islet donor mice, however, did not reduce the percentage of necrotic cells (PI+cells: 20±3.2% vs. 19±4.7%, P=1.0).

Example 37

Figure 35A:
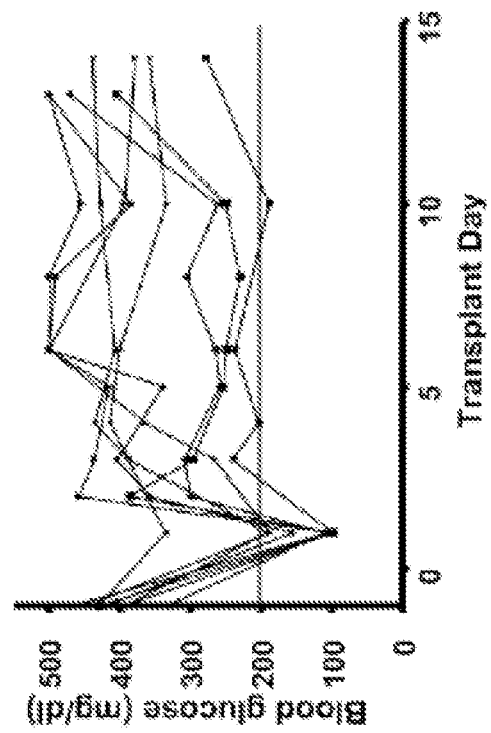
FIG. 35. Reversal of diabetes following transplantation of a marginal mass of syngeneic islets. Diabetic DBA/2 mice received 200 syngeneic islet cells under the right kidney capsule. Reversal of diabetes was defined as random nonfasting blood glucose levels below 200 mg/dl on 3-consecutive days. (A) Blood glucose levels of each individual control mouse following transplantation of 200 syngeneic islets. (B) Blood glucose levels of each individual SS-31 treated mouse following transplantation of 200 syngeneic islets. (C) Reversal of diabetes following transplantation of a marginal islet cell mass in SS-31 treatment vs. control. Number of normoglycemic mice by day 1, 3, 5, 10 and 14 post transplantation and two-tailed P-valued calculated using chi-squared bivariate analysis are shown.
Figure 35B:
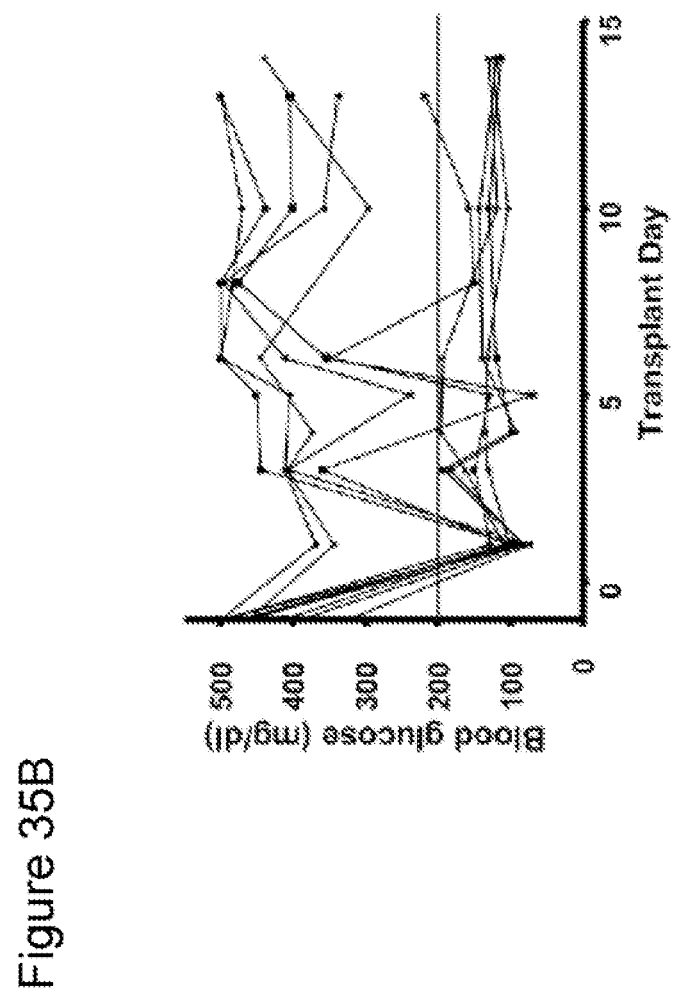

SS-31 Improves Post-Transplant Islet Graft Function (FIG. 35)

The SS-31 treatment associated decrease in islet cell apoptosis and enhanced viability had a beneficial functional consequence. In a marginal islet cell mass transplantation model, 0 of 8 recipients of islets isolated from pancreas harvested from the control mice had successful reversal of hyperglycemia (defined as three consecutive blood glucose levels<200 mg/dl), whereas sustained normoglycemia occurred in 5 of ten recipients of islets isolated from pancreas from the SS-31 treated donor mice (FIG. 35). It is worth noting that reversal of hyperglycemia was prompt (by day 1 post transplant) and discontinuation SS-31 treatment of the islet graft recipient on day 10 did not result in return of hyperglycemia demonstrating a sustained effect of SS-31 treatment on islet cell function.

What is claimed is:

1. A method for reducing loss of dopamine-producing neurons in a mammal having or suspected of having Parkinson's disease, the method comprising administering to the mammal an effective amount of a peptide having the formula D-Arg-2'6'Dmt-Lys-Phe-NH$_2$.

2. The method according to claim 1, wherein the mammal is a human.

3. The method according to claim 1, wherein the peptide is administered orally, topically, intranasally, systemically, intravenously, subcutaneously, intramuscularly, intracerebroventricularly, intrathecally, or transdermally.

4. The method of claim 1, wherein the peptide is mixed with a pharmaceutically acceptable carrier.

5. A method for reducing motor neuron loss caused by or resulting from amyotrophic lateral sclerosis (ALS) in a mammal in need thereof, the method comprising administering to the mammal an effective amount of a peptide having the formula D-Arg-2'6'Dmt-Lys-Phe-NH$_2$.

6. The method according to claim 5, wherein the mammal is a human.

7. The method according to claim 5, wherein the peptide is administered orally, topically, intranasally, systemically, intravenously, subcutaneously, intramuscularly, intracerebroventricularly, intrathecally, or transdermally.

8. The method of claim 5, wherein the peptide is mixed with a pharmaceutically acceptable carrier.

* * * * *